US012171794B2

(12) United States Patent
Beales et al.

(10) Patent No.: US 12,171,794 B2
(45) Date of Patent: Dec. 24, 2024

(54) GENE THERAPY FOR CILIOPATHIES

(71) Applicant: UCL BUSINESS LTD, London (GB)

(72) Inventors: Philip Beales, London (GB); Victor Hernandez, London (GB)

(73) Assignee: UCL BUSINESS LTD, London (GB)

( * ) Notice: Subject to any disclaimer, the term of this patent is extended or adjusted under 35 U.S.C. 154(b) by 913 days.

(21) Appl. No.: 16/610,883

(22) PCT Filed: May 4, 2018

(86) PCT No.: PCT/GB2018/051219

§ 371 (c)(1),
(2) Date: Nov. 4, 2019

(87) PCT Pub. No.: WO2018/203092

PCT Pub. Date: Nov. 8, 2018

(65) Prior Publication Data

US 2020/0069753 A1 Mar. 5, 2020

(30) Foreign Application Priority Data

May 5, 2017 (GB) ..................................... 1707212

(51) Int. Cl.

| | |
|---|---|
| ***C12N 15/864*** | (2006.01) |
| ***A61K 35/761*** | (2015.01) |
| ***A61K 48/00*** | (2006.01) |
| ***C07K 14/47*** | (2006.01) |
| ***C12N 15/113*** | (2010.01) |
| ***C12N 15/12*** | (2006.01) |
| ***C12N 15/86*** | (2006.01) |

(52) U.S. Cl.

CPC ........ *A61K 35/761* (2013.01); *A61K 48/0066* (2013.01); *A61K 48/0083* (2013.01); *C07K 14/4702* (2013.01); *C12N 15/86* (2013.01); *C12N 2750/14143* (2013.01); *C12N 2800/22* (2013.01)

(58) Field of Classification Search

None
See application file for complete search history.

(56) References Cited

U.S. PATENT DOCUMENTS

| | | | | |
|---|---|---|---|---|
| 6,962,788 | B2 * | 11/2005 | Sheffield | C12Q 1/6883 435/7.1 |
| 2003/0232375 | A1 | 12/2003 | Sheffield et al. | |
| 2010/0130429 | A1 * | 5/2010 | Katsanis | C12Q 1/6883 435/6.15 |
| 2013/0158104 | A1 | 6/2013 | Tubert et al. | |
| 2016/0022836 | A1 * | 1/2016 | Banfi | A61P 27/02 514/44 R |
| 2020/0069753 | A1 | 3/2020 | Beales et al. | |

FOREIGN PATENT DOCUMENTS

| | | | |
|---|---|---|---|
| AU | 2018262427 | B2 | 6/2024 |
| CA | 3060187 | A1 | 11/2018 |
| CN | 110753559 | A | 2/2020 |
| EP | 3628011 | A1 | 4/2020 |
| JP | 2013531490 | A | 8/2013 |
| WO | WO 03102141 | * | 12/2003 |
| WO | 2007101094 | A2 | 9/2007 |
| WO | 2018203092 | A1 | 11/2018 |

OTHER PUBLICATIONS

Wang et al, Enhancing Transgene Expression from Recombinant AAV8 Vectors in Different Tissues Using Woodchuck Hepatitis Virus Post-Transcriptional Regulatory Element, Int J. Med. Sci, 2016, pp. 286-291).*

Seo et al, "Subretinal Gene Therapy of Mice with Bardet-Biedl Syndrome Type 1," Investigative Opthalmology & Visual Science, vol. 54, No. 9, Sep. 11, 2013, pp. 6118-6132.

Williams et al., "Gene Therapeutic Reversal of Peripheral Olfactory Impairment in Bardet-Biedl Syndrome," Molecular Therapy: The Journal of the American Society of Gene Therapy, vol. 25, No. 4, Apr. 1, 2017, pp. 904-916.

Testa et al., "Evaluation of Italian Patients with Leber Congenital Amaurosis Due to AIPL1 Mutations Highlights the Potential Applicability of Gene Therapy," Investigative Opthalmology & Visual Science, vol. 52, No. 8, Jul. 27, 2011, pp. 5618-5624.

Li et al., "Gene Therapy Following Subretinal AAV5 Vector Delivery is not Affected by a Previous Intravitreal AAV5 Vector Administration in the Partner Eye," Molecular Vision, Jan. 1, 2009, pp. 267-275.

Burnight et al., "CEP290 Gene Transfer Rescues Leber Congenital Amaurosis Cellular Phenotype," Gene Therapy, vol. 21, No. 7, May 8, 2014, pp. 662-672.

Waters et al., "Ciliopathies: An Expanding Disease Spectrum," Pediatric Nephrology; Journal of the International Pediatric Nephrology Associate, vol. 26, No. 7, Jan. 6, 2011, pp. 1039-1056.

Seo et al., "BBS6, BBS10, and BBS12 Form a Complex with CCT/TRiC Family Chaperonins and Mediate BBSome Assembly," Proceedings of the National Academy of Sciences, vol. 107, No. 4, Jan. 4, 2010, pp. 1488-1493.

Addgene, "Adeno-Associated Virus (AAV) Guide," XP002782703, Retrieved on Jun. 29, 2018.

* cited by examiner

*Primary Examiner* — Maria Marvich
(74) *Attorney, Agent, or Firm* — Snell & Wilmer, L.L.P.; April Wurster

(57) ABSTRACT

There is described a vector for treating a ciliopathy such as Bardet-Biedl syndrome, wherein the vector comprises a promoter operably linked to a ciliopathy gene, wherein the vector can provide transduction of the ciliopathy gene into multiple organs, wherein the promoter is a ubiquitous promoter which can provide expression of the ciliopathy gene in the transduced organs, and wherein the ciliopathy gene encodes a functional protein corresponding to the protein that is mutated in the ciliopathy. Also described is the use of the above vector in a method of treating a ciliopathy, the method comprising administering a therapeutically effective amount of the vector to a patient suffering from a ciliopathy.

9 Claims, 20 Drawing Sheets

Specification includes a Sequence Listing.

A

B

| | Mean | SEM |
|---|---|---|
| EFS_WTBBS1 | 1.00 | 0 |
| EFS_COSEQ1_BBS1 | 1.62 | 0.1519 |
| EFS_COSEQ2_BBS1 | 0.57 | 1.0081 |
| UBC_WTBBS1 | 0.42 | 7.61E-03 |
| UBC_COSEQ1_BBS1 | 0.85 | 0.0636 |
| UBC_COSEQ2_BBS1 | 0.38 | 0.0717 |
| CMV_WTBBS1 | 10.37 | 1.5636 |
| CMV_COSEQ1_BBS1 | 19.32 | 1.9475 |
| CMV_COSEQ2_BBS1 | 5.53 | 1.3437 |
| CAG_WTBBS1 | 0.18 | 3.58E-03 |
| CAG_COSEQ1_BBS1 | 7.41 | 6.39E-03 |
| CAG_COSEQ2_BBS1 | 2.20 | 0.1069 |
| CBA_WTBBS1 | 1.22 | 0.0971 |
| CBA_COSEQ1_BBS1 | 0.22 | 0.0256 |
| CBA_COSEQ2_BBS1 | 0.16 | 8.88E-03 |

| | Mean | SEM |
|---|---|---|
| Untransfected | 1.00 | 0.00 |
| EFS_WTBBS10 | 296.84 | 23.46 |
| EFS_COSEQ1_BBS10 | 91.68 | 16.95 |
| EFS_COSEQ2_BBS10 | 126.99 | 29.61 |
| UBC_WTBBS10 | 37.94 | 0.78 |
| UBC_COSEQ1_BBS10 | 59.05 | 10.40 |
| UBC_COSEQ2_BBS10 | 43.52 | 9.70 |
| CMV_WTBBS10 | 69.50 | 6.01 |
| CMV_COSEQ1_BBS10 | 405.91 | 40.51 |
| CMV_COSEQ2_BBS10 | 230.74 | 32.99 |
| CAG_WTBBS10 | 34.92 | 5.77 |
| CAG_COSEQ1_BBS10 | 147.97 | 17.61 |
| CAG_COSEQ2_BBS10 | 168.65 | 44.14 |
| CBA_WTBBS10 | 15.66 | 0.35 |
| CBA_COSEQ1_BBS10 | 60.67 | 7.31 |
| CBA_COSEQ2_BBS10 | 67.18 | 9.93 |

| Sample | Mean | SEM |
|---|---|---|
| EFS_WTBBS1 | 1.00 | 0.00 |
| EFS_COSEQ1_BBS1 | 14.63 | 4.76 |
| EF1a_COSEQ2_BBS1 | 11.36 | 0.92 |
| CMV_WTBBS1 | 17.64 | 4.63 |
| CMV_COSEQ1_BBS1 | 33.88 | 14.23 |
| CMV_COSEQ2_BBS1 | 22.63 | 7.33 |
| CAG_WTBBS1 | 10.81 | 4.97 |
| CAG_COSEQ1_BBS1 | 24.58 | 7.40 |
| CAG_COSEQ2_BBS1 | 25.94 | 9.37 |

| Sample | Mean | SEM |
|---|---|---|
| EFS_WTBBS1 | 1.00 | 0.00 |
| EFS_COSEQ1_BBS1 | 14.63 | 4.76 |
| EF1a_COSEQ2_BBS1 | 11.36 | 0.92 |
| CMV_WTBBS1 | 17.64 | 4.63 |
| CMV_COSEQ1_BBS1 | 33.88 | 14.23 |
| CMV_COSEQ2_BBS1 | 22.63 | 7.33 |
| CAG_WTBBS1 | 10.81 | 4.97 |
| CAG_COSEQ1_BBS1 | 24.58 | 7.40 |
| CAG_COSEQ2_BBS1 | 25.94 | 9.37 |

GENE THERAPY FOR CILIOPATHIES

FIELD OF THE INVENTION

The present invention relates to gene therapy vectors for the treatment of ciliopathies, including Bardet-Biedl Syndrome.

BACKGROUND TO THE INVENTION

The ciliopathies have recently emerged as a medically important category of disease which are caused by dysfunction of non-motile cilia found on most cells in the body (Waters & Beales, Pediatr Nephrol (2011) 26:1039-1056). Most ciliopathies share common phenotypes, including retinal degeneration. It has been predicted that there are over 100 diseases that probably arise from dysfunction of cilia whereupon more than 30 conditions have now been proven. All of these conditions are debilitating and often life-limiting and, as they are nearly all loss of function, most would benefit from gene therapy approaches to treatment. Ciliopathies have a collective prevalence of around 1 in 500 of the general population. All ciliopathies have disturbed cilia function, hence the overlap in organ involvement.

The autosomal recessive Bardet-Biedl Syndrome (BBS) is one of the best characterised ciliopathies and is associated with early onset blindness, severe obesity, complex endocrine dysfunction, cognitive impairment and renal failure. Patients born with the inherited Bardet-Biedl syndrome will experience a range of debilitating medical problems, some of which are life-limiting. Affected children will eventually go blind usually beginning in their first decade owing to a failure of the light-sensitive cells at the back of the eye (the retina). Within the first year of life they will gain an extraordinary amount of body weight which if unchecked will progress to life-threatening obesity, diabetes and high blood pressure. Many patients will also develop kidney failure (that may require dialysis treatment and/or kidney transplant) at some point in their lives and most will have some form of learning difficulties. Together these problems will impact adult patients' ability to live independently and most are unemployed. Even when diagnosed early, symptom-based treatments will only manage unpreventable complications such as retinal degeneration and obesity refractory to dietary measures.

BBS, like many ciliopathies, is an autosomal recessive genetic disorder. So far 21 genes have been found to be causative. Many of these gene products interact in multi-subunit complexes. For example, a number of these proteins form a complex called the BBSome. The BBSome is believed to mediate protein trafficking to the primary cilium. Another complex, the BBS/CCT chaperonin complex, facilitates the BBSome assembly and is composed of several BBS proteins and a number of CCT chaperonin proteins. As a result of the protein products of BBS genes physically interacting to perform a common function, mutation of many different genes cause the same unusual combination of phenotypic findings. The most common genes that are mutated in BBS patients are BBS1 (42%) and BBS10 (22%). More than 30 mutations in the BBS1 gene have been identified in people with Bardet-Biedl syndrome. The human BBS1 gene is located on the long (q) arm of chromosome 11 at position 13. Mutations in the BBS1 gene likely affect the normal formation and function of cilia. Defects in these cell structures disrupt important chemical signalling pathways during development and lead to abnormalities of sensory perception. The human BBS1 gene contains 17 exons and spans approximately 23 kb. Most BBS1 gene mutations are missense or stop mutations and the most common mutation replaces the amino acid methionine with the amino acid arginine at protein position 390 (Met390Arg or M390R). The M390R mutation accounts for approximately 80% of all BBS1 mutations. The human BBS10 gene sits on chromosome 12 and the BBS10 transcript contains only 2 exons encoding for a 723 amino acid protein. The mutations found in BBS10 patients are a mix of missense, non-sense and frameshift mutations. The most common change is C91fs with nearly 50% frequency.

So far, all current gene therapies for ciliopathies are targeted to treat a single damaged organ. For example, a number of groups have attempted to treat retinopathy of the eye using subretinal injection of gene therapy vectors (e.g. Seo et al., *Invest Ophthalmol Vis Sci.* 54(9):6118-32 (2013)). However, using such an approach which directly targets a single organ would mean that a different vector would need to be custom designed for each individual target organ for multi-system disorders such as ciliopathies. If many vectors need to be used, the costs could be prohibitive and the regulatory processes cumbersome. The use of a single injection rather than multi-organ injection will be highly desirable for patients; it will be less invasive, reduce visits to the clinic and reduce the risks due to multiple treatments. Therefore, there is a need to use approaches which can address the deficiencies in some or all affected organs rather than individual organs.

Williams C L et al. (Mol Ther. 25(4):904-916 (2017)) describes the reversal of peripheral olfactory impairment in Bardet-Biedl syndrome. As with the work discussed above, Williams describes the targeting of a single organ and does not contemplate treating multiple organs. Williams targets the olfactory sensory neurons (OSNs) in the nasal tissue of mice through the intranasal administration of a gene therapy vector containing a mouse BBS gene tagged with a fluorescent protein (GFP or mCherry). Crucially, in the mouse model used by Williams, BBS protein function is only missing in mature olfactory neurons (OSNs), so this mouse model can only show recovery in the OSN cells. This means the experiments described in Williams cannot provide any information on BBS gene expression in other cell types or tissues due to the mouse model used and cannot show multiple organ recovery.

WO 03/102141 describes the identification of a mutated BBS1 gene and various uses thereof.

SUMMARY OF THE INVENTION

In a first aspect of the invention, there is provided a vector for treating a ciliopathy, wherein the vector comprises a promoter operably linked to a ciliopathy gene, wherein the vector can provide transduction of the ciliopathy gene into multiple organs, wherein the promoter is a ubiquitous promoter which can provide expression of the ciliopathy gene in the transduced organs, and wherein the ciliopathy gene encodes a functional protein corresponding to the protein that is mutated in the ciliopathy.

Ciliopathies are generally caused by a mutation to a single gene which results in dysfunction of non-motile cilia found on most cells in the body. Therefore, the introduction of a correct gene which expresses the functional protein compensates for the mutated gene and ameliorates the effects of the ciliopathy. The vector defined above provides transduction in multiple organs. Therefore, administration of the vector by one route of administration can be used to provide gene expression in multiple organs to ameliorate the pathologies associated with the ciliopathy. This means that it is not necessary to treat each affected organ or tissue individually as has been done before. This approach targeting multiple organs at once has not been used previously in ciliopathies and it was not contemplated that such an approach would work.

Ciliopathies are a group of disorders associated with genetic mutations encoding defective proteins, which result in abnormal formation or function of cilia. Therefore, a ciliopathy is defined as "a disorder associated with a genetic mutation encoding no protein or a defective protein, which results in abnormal formation or function of cilia". As cilia are a component of almost all vertebrate cells, cilia dysfunction can manifest as a constellation of features that include characteristically, retinal degeneration, renal disease and cerebral anomalies. Additional manifestations include congenital fibrocystic diseases of the liver, diabetes, obesity and skeletal dysplasias. Ciliopathic features have been associated with mutations in over 40 genes.

The ciliopathy that can be treated using the vector described above can be any ciliopathy which can be treated by the expression of a functional protein corresponding to the protein that is mutated in the ciliopathy. Primarily, this is ciliopathies which result from mutations which cause loss of protein function. Expression of the functional protein restores the protein function which ameliorates the abnormal formation or function of cilia. Such ciliopathies are known to those skilled in the art. The ciliopathy that can be treated may be selected from Bardet-Biedl syndrome, Meckel-Gruber syndrome, Nephronophthisis, Senior-Loken syndrome, McKusick-Kaufman syndrome, Leber's congenital amaurosis and Joubert Syndrome. In some embodiments, the ciliopathy that is treated with the vector is selected from Bardet-Biedl syndrome, Nephronophthisis, Senior-Loken syndrome, McKusick-Kaufman syndrome and Leber's congenital amaurosis. In other embodiments, the ciliopathy that is treated with the vector is selected from Bardet-Biedl syndrome, Senior-Loken syndrome, McKusick-Kaufman syndrome and Leber's congenital amaurosis. In various embodiments, the ciliopathy that is treated with the vector is selected from Bardet-Biedl syndrome and McKusick-Kaufman syndrome. In particular embodiments, the ciliopathy that is treated with the vector is Bardet-Biedl syndrome.

The vector comprises a ciliopathy gene which encodes a functional protein corresponding to the protein that is mutated in the ciliopathy. Put another way, the ciliopathy gene encodes a functional protein corresponding to the mutated protein that causes the ciliopathy. The ciliopathy gene preferably encodes the human protein, e.g. the wild type human protein. The precise ciliopathy gene will depend on the ciliopathy to be treated and the gene which is mutated and causes the pathologies of the ciliopathy. So, for example, if a patient has a ciliopathy which is caused by a mutation in the BBS1 gene, the vector for treating this patient will comprise a ciliopathy gene which encodes a functional BBS1 protein.

In some embodiments, the ciliopathy gene encodes a functional protein selected from the BBS1, BBS2, BBS3/ARL6, BBS4, BBS5, BBS6/MKKS, BBS7, BBS8, BBS9, BBS10, BBS11/TRIM32, BBS12, BBS13/MKS1, BBS14/CEP290, BBS15/C2ORF86, BBS16/SDCCAG8, BBS17/LZTFL1, BBS18/BBIP1, BBS19/IFT27, BBS20/IFT74 and BBS21/C8ORF37 protein.

In other embodiments, the ciliopathy gene encodes a functional protein selected from the BBS1, BBS2, BBS3/ARL6, BBS4, BBS5, BBS6/MKKS, BBS7, BBS8, BBS9, BBS10, BBS11/TRIM32, BBS12, BBS14/CEP290, BBS15/C2ORF86, BBS16/SDCCAG8, BBS17/LZTFL1, BBS18/BBIP1, BBS19/IFT27 and BBS20/IFT74 protein.

In various embodiments, the ciliopathy gene encodes a functional protein selected from the BBS1, BBS2, BBS3/ARL6, BBS4, BBS5, BBS6/MKKS, BBS7, BBS8, BBS9, BBS10, BBS11/TRIM32, BBS12, BBS15/C2ORF86, BBS16/SDCCAG8, BBS17/LZTFL1, BBS18/BBIP1, BBS19/IFT27 and BBS20/IFT74 protein.

In several embodiments, the ciliopathy gene encodes a functional protein selected from the BBS1, BBS2, BBS3/ARL6, BBS4, BBS5, BBS6/MKKS, BBS7, BBS8, BBS9, BBS10, BBS12 and BBS18/BBIP1 protein.

In particular embodiments, the ciliopathy gene encodes a functional protein selected from the BBS1, BBS2, BBS3/ARL6, BBS4, BBS5, BBS6/MKKS, BBS7, BBS8, BBS9, BBS10 andBBS12 protein.

In specific embodiments, the ciliopathy gene encodes a functional protein selected from the BBS1 and BBS10 protein.

In some embodiments, the ciliopathy gene encodes a functional BBS1 protein.

In other embodiments, the ciliopathy gene encodes a functional BBS10 protein.

In some embodiments, the ciliopathy that is to be treated is Bardet-Biedl syndrome and the ciliopathy gene encodes a functional protein selected from the BBS1, BBS2, BBS3/ARL6, BBS4, BBS5, BBS6/MKKS, BBS7, BBS8, BBS9, BBS10, BBS11/TRIM32, BBS12, BBS13/MKS1, BBS14/CEP290, BBS15/C2ORF86, BBS16/SDCCAG8, BBS17/LZTFL1, BBS18/BBIP1, BBS19/IFT27, BBS20/IFT74 and BBS21/C8ORF37 protein.

In other embodiments, the ciliopathy that is to be treated is Meckel-Gruber syndrome and the ciliopathy gene encodes a functional BBS13/MKS1 protein.

In various embodiments, the ciliopathy that is to be treated is Nephronophthisis and the ciliopathy gene encodes a functional BBS14/CEP290 protein.

In particular embodiments, the ciliopathy that is to be treated is Senior-Loken syndrome and the ciliopathy gene encodes a functional BBS14/CEP290 protein.

In some embodiments, the ciliopathy that is to be treated is McKusick-Kaufman syndrome and the ciliopathy gene encodes a functional BBS6/MKKS protein.

In other embodiments, the ciliopathy that is to be treated is Leber's congenital amaurosis and the ciliopathy gene encodes a functional BBS14/CEP290 protein.

In various embodiments, the ciliopathy that is to be treated is Joubert Syndrome and the ciliopathy gene encodes a functional BBS14/CEP290 protein.

The functional protein encoded by the ciliopathy gene preferably does not contain additional amino acids that are not found in the wild type protein. Any additional amino acids could interfere in the normal functioning of the protein. For example, it is preferred that the functional protein does not comprise a fluorescent protein such as green fluorescent protein (GFP) or mCherry, or tags such such as a FLAG-tag or a polyhistidine-tag.

In particular embodiments, the ciliopathy gene has the nucleotide sequence of SEQ ID NO. 1 or has at least 70% sequence identity thereto, and encodes a functional BBS1 protein. In some embodiments, the ciliopathy gene has the nucleotide sequence of SEQ ID NO. 1 or has at least 72% sequence identity thereto, and encodes a functional BBS1 protein. In a number of embodiments, the ciliopathy gene has the nucleotide sequence of SEQ ID NO. 1 or has at least 74% sequence identity thereto, and encodes a functional BBS1 protein. In other embodiments, the ciliopathy gene has the nucleotide sequence of SEQ ID NO. 1 or has at least 76% sequence identity thereto, and encodes a functional BBS1 protein. In various embodiments, the ciliopathy gene has the nucleotide sequence of SEQ ID NO. 1 or has at least 78% sequence identity thereto, and encodes a functional BBS1 protein. In particular embodiments, the ciliopathy gene has the nucleotide sequence of SEQ ID NO. 1 or has at least 80% sequence identity thereto, and encodes a functional BBS1 protein. In certain embodiments, the ciliopathy gene has the nucleotide sequence of SEQ ID NO. 1 or has at least 82% sequence identity thereto, and encodes a functional BBS1 protein. In various embodiments, the ciliopathy gene has the nucleotide sequence of SEQ ID NO. 1 or has at least 84% sequence identity thereto, and encodes a functional BBS1 protein. In some embodiments, the ciliopathy gene has the nucleotide sequence of SEQ ID NO. 1 or has at least 85% sequence identity thereto, and encodes a functional BBS1 protein. In certain embodiments, the ciliopathy gene has the nucleotide sequence of SEQ ID NO. 1 or has at least 86% sequence identity thereto, and encodes a functional BBS1 protein. In a number of embodiments, the ciliopathy gene has the nucleotide sequence of SEQ ID NO. 1 or has at least 88% sequence identity thereto, and encodes a functional BBS1 protein. In other embodiments, the ciliopathy gene has the nucleotide sequence of SEQ ID NO. 1 or has at least 90% sequence identity thereto, and encodes a functional BBS1 protein. In certain embodiments, the ciliopathy gene has the nucleotide sequence of SEQ ID NO. 1 or has at least 92% sequence identity thereto, and encodes a functional BBS1 protein. In a number of embodiments, the ciliopathy gene has the nucleotide sequence of SEQ ID NO. 1 or has at least 94% sequence identity thereto, and encodes a functional BBS1 protein. In various embodiments, the ciliopathy gene has the nucleotide sequence of SEQ ID NO. 1 or has at least 95% sequence identity thereto, and encodes a functional BBS1 protein. In certain embodiments, the ciliopathy gene has the nucleotide sequence of SEQ ID NO. 1 or has at least 96% sequence identity thereto, and encodes a functional BBS1 protein. In some embodiments, the ciliopathy gene has the nucleotide sequence of SEQ ID NO. 1 or has at least 97% sequence identity thereto, and encodes a functional BBS1 protein. In a number of embodiments, the ciliopathy gene has the nucleotide sequence of SEQ ID NO. 1 or has at least 98% sequence identity thereto, and encodes a functional BBS1 protein. In some embodiments, the ciliopathy gene has the nucleotide sequence of SEQ ID NO. 1 or has at least 99% sequence identity thereto, and encodes a functional BBS1 protein. In particular embodiments, the ciliopathy gene has the nucleotide sequence of SEQ ID NO. 1.

In particular embodiments, the ciliopathy gene has the nucleotide sequence of SEQ ID NO. 2 or has at least 70% sequence identity thereto, and encodes a functional BBS10 protein. In some embodiments, the ciliopathy gene has the nucleotide sequence of SEQ ID NO. 2 or has at least 72% sequence identity thereto, and encodes a functional BBS10 protein. In a number of embodiments, the ciliopathy gene has the nucleotide sequence of SEQ ID NO. 2 or has at least 74% sequence identity thereto, and encodes a functional BBS10 protein. In other embodiments, the ciliopathy gene has the nucleotide sequence of SEQ ID NO. 2 or has at least 76% sequence identity thereto, and encodes a functional BBS10 protein. In various embodiments, the ciliopathy gene has the nucleotide sequence of SEQ ID NO. 2 or has at least 78% sequence identity thereto, and encodes a functional BBS10 protein. In particular embodiments, the ciliopathy gene has the nucleotide sequence of SEQ ID NO. 2 or has at least 80% sequence identity thereto, and encodes a functional BBS10 protein. In certain embodiments, the ciliopathy gene has the nucleotide sequence of SEQ ID NO. 2 or has at least 82% sequence identity thereto, and encodes a functional BBS10 protein. In various embodiments, the ciliopathy gene has the nucleotide sequence of SEQ ID NO. 2 or has at least 84% sequence identity thereto, and encodes a functional BBS10 protein. In some embodiments, the ciliopathy gene has the nucleotide sequence of SEQ ID NO. 2 or has at least 85% sequence identity thereto, and encodes a functional BBS10 protein. In certain embodiments, the ciliopathy gene has the nucleotide sequence of SEQ ID NO. 2 or has at least 86% sequence identity thereto, and encodes a functional BBS10 protein. In a number of embodiments, the ciliopathy gene has the nucleotide sequence of SEQ ID NO. 2 or has at least 88% sequence identity thereto, and encodes a functional BBS10 protein. In other embodiments, the ciliopathy gene has the nucleotide sequence of SEQ ID NO. 2 or has at least 90% sequence identity thereto, and encodes a functional BBS10 protein. In certain embodiments, the ciliopathy gene has the nucleotide sequence of SEQ ID NO. 2 or has at least 92% sequence identity thereto, and encodes a functional BBS10 protein. In a number of embodiments, the ciliopathy gene has the nucleotide sequence of SEQ ID NO. 2 or has at least 94% sequence identity thereto, and encodes a functional BBS10 protein. In various embodiments, the ciliopathy gene has the nucleotide sequence of SEQ ID NO. 2 or has at least 95% sequence identity thereto, and encodes a functional BBS10 protein. In certain embodiments, the ciliopathy gene has the nucleotide sequence of SEQ ID NO. 2 or has at least 96% sequence identity thereto, and encodes a functional BBS10 protein. In some embodiments, the ciliopathy gene has the nucleotide sequence of SEQ ID NO. 2 or has at least 97% sequence identity thereto, and encodes a functional BBS10 protein. In a number of embodiments, the ciliopathy gene has the nucleotide sequence of SEQ ID NO. 2 or has at least 98% sequence identity thereto, and encodes a functional BBS10 protein. In some embodiments, the ciliopathy gene has the nucleotide sequence of SEQ ID NO. 2 or has at least 99% sequence identity thereto, and encodes a functional BBS10 protein. In particular embodiments, the ciliopathy gene has the nucleotide sequence of SEQ ID NO. 2.

In the embodiments above, the nucleotide sequence of the ciliopathy gene may be codon optimised to maximise expression of the protein. In codon optimisation, the amino acid sequence of the encoded protein remains the same so it will still be functional. It is simply the nucleotide sequence that is modified. SEQ ID NOs. 11 and 12 are codon optimised nucleotide sequences encoding BBS1, and SEQ ID NOs. 13 and 14 are codon optimised nucleotide sequences encoding BBS10. These sequences have been found to give an unexpectedly large increase in gene expression.

In particular embodiments, the ciliopathy gene has the nucleotide sequence of SEQ ID NO. 11 or has at least 70% sequence identity thereto, and encodes a functional BBS1 protein. In some embodiments, the ciliopathy gene has the nucleotide sequence of SEQ ID NO. 11 or has at least 72% sequence identity thereto, and encodes a functional BBS1 protein. In a number of embodiments, the ciliopathy gene has the nucleotide sequence of SEQ ID NO. 11 or has at least 74% sequence identity thereto, and encodes a functional BBS1 protein. In other embodiments, the ciliopathy gene has the nucleotide sequence of SEQ ID NO. 11 or has at least 76% sequence identity thereto, and encodes a functional BBS1 protein. In various embodiments, the ciliopathy gene has the nucleotide sequence of SEQ ID NO. 11 or has at least 78% sequence identity thereto, and encodes a functional BBS1 protein. In particular embodiments, the ciliopathy gene has the nucleotide sequence of SEQ ID NO. 11 or has at least 80% sequence identity thereto, and encodes a functional BBS1 protein. In certain embodiments, the ciliopathy gene has the nucleotide sequence of SEQ ID NO. 11 or has at least 82% sequence identity thereto, and encodes a functional BBS1 protein. In various embodiments, the ciliopathy gene has the nucleotide sequence of SEQ ID NO. 11 or has at least 84% sequence identity thereto, and encodes a functional BBS1 protein. In some embodiments, the ciliopathy gene has the nucleotide sequence of SEQ ID NO. 11 or has at least 85% sequence identity thereto, and encodes a functional BBS1 protein. In certain embodiments, the ciliopathy gene has the nucleotide sequence of SEQ ID NO. 11 or has at least 86% sequence identity thereto, and encodes a functional BBS1 protein. In a number of embodiments, the ciliopathy gene has the nucleotide sequence of SEQ ID NO. 11 or has at least 88% sequence identity thereto, and encodes a functional BBS1 protein. In other embodiments, the ciliopathy gene has the nucleotide sequence of SEQ ID NO. 11 or has at least 90% sequence identity thereto, and encodes a functional BBS1 protein. In certain embodiments, the ciliopathy gene has the nucleotide sequence of SEQ ID NO. 11 or has at least 92% sequence identity thereto, and encodes a functional BBS1 protein. In a number of embodiments, the ciliopathy gene has the nucleotide sequence of SEQ ID NO. 11 or has at least 94% sequence identity thereto, and encodes a functional BBS1 protein. In various embodiments, the ciliopathy gene has the nucleotide sequence of SEQ ID NO. 11 or has at least 95% sequence identity thereto, and encodes a functional BBS1 protein. In certain embodiments, the ciliopathy gene has the nucleotide sequence of SEQ ID NO. 11 or has at least 96% sequence identity thereto, and encodes a functional BBS1 protein. In some embodiments, the ciliopathy gene has the nucleotide sequence of SEQ ID NO. 11 or has at least 97% sequence identity thereto, and encodes a functional BBS1 protein. In a number of embodiments, the ciliopathy gene has the nucleotide sequence of SEQ ID NO. 11 or has at least 98% sequence identity thereto, and encodes a functional BBS1 protein. In some embodiments, the ciliopathy gene has the nucleotide sequence of SEQ ID NO. 11 or has at least 99% sequence identity thereto, and encodes a functional BBS1 protein. In particular embodiments, the ciliopathy gene has the nucleotide sequence of SEQ ID NO. 11.

In particular embodiments, the ciliopathy gene has the nucleotide sequence of SEQ ID NO. 12 or has at least 70% sequence identity thereto, and encodes a functional BBS1 protein. In some embodiments, the ciliopathy gene has the nucleotide sequence of SEQ ID NO. 12 or has at least 72% sequence identity thereto, and encodes a functional BBS1 protein. In a number of embodiments, the ciliopathy gene has the nucleotide sequence of SEQ ID NO. 12 or has at least 74% sequence identity thereto, and encodes a functional BBS1 protein. In other embodiments, the ciliopathy gene has the nucleotide sequence of SEQ ID NO. 12 or has at least 76% sequence identity thereto, and encodes a functional BBS1 protein. In various embodiments, the ciliopathy gene has the nucleotide sequence of SEQ ID NO. 12 or has at least 78% sequence identity thereto, and encodes a functional BBS1 protein. In particular embodiments, the ciliopathy gene has the nucleotide sequence of SEQ ID NO. 12 or has at least 80% sequence identity thereto, and encodes a functional BBS1 protein. In certain embodiments, the ciliopathy gene has the nucleotide sequence of SEQ ID NO. 12 or has at least 82% sequence identity thereto, and encodes a functional BBS1 protein. In various embodiments, the ciliopathy gene has the nucleotide sequence of SEQ ID NO. 12 or has at least 84% sequence identity thereto, and encodes a functional BBS1 protein. In some embodiments, the ciliopathy gene has the nucleotide sequence of SEQ ID NO. 12 or has at least 85% sequence identity thereto, and encodes a functional BBS1 protein. In certain embodiments, the ciliopathy gene has the nucleotide sequence of SEQ ID NO. 12 or has at least 86% sequence identity thereto, and encodes a functional BBS1 protein. In a number of embodiments, the ciliopathy gene has the nucleotide sequence of SEQ ID NO. 12 or has at least 88% sequence identity thereto, and encodes a functional BBS1 protein. In other embodiments, the ciliopathy gene has the nucleotide sequence of SEQ ID NO. 12 or has at least 90% sequence identity thereto, and encodes a functional BBS1 protein. In certain embodiments, the ciliopathy gene has the nucleotide sequence of SEQ ID NO. 12 or has at least 92% sequence identity thereto, and encodes a functional BBS1 protein. In a number of embodiments, the ciliopathy gene has the nucleotide sequence of SEQ ID NO. 12 or has at least 94% sequence identity thereto, and encodes a functional BBS1 protein. In various embodiments, the ciliopathy gene has the nucleotide sequence of SEQ ID NO. 12 or has at least 95% sequence identity thereto, and encodes a functional BBS1 protein. In certain embodiments, the ciliopathy gene has the nucleotide sequence of SEQ ID NO. 12 or has at least 96% sequence identity thereto, and encodes a functional BBS1 protein. In some embodiments, the ciliopathy gene has the nucleotide sequence of SEQ ID NO. 12 or has at least 97% sequence identity thereto, and encodes a functional BBS1 protein. In a number of embodiments, the ciliopathy gene has the nucleotide sequence of SEQ ID NO. 12 or has at least 98% sequence identity thereto, and encodes a functional BBS1 protein. In some embodiments, the ciliopathy gene has the nucleotide sequence of SEQ ID NO. 12 or has at least 99% sequence identity thereto, and encodes a functional BBS1 protein. In particular embodiments, the ciliopathy gene has the nucleotide sequence of SEQ ID NO. 12.

In particular embodiments, the ciliopathy gene has the nucleotide sequence of SEQ ID NO. 13 or has at least 70% sequence identity thereto, and encodes a functional BBS10 protein. In some embodiments, the ciliopathy gene has the nucleotide sequence of SEQ ID NO. 13 or has at least 72% sequence identity thereto, and encodes a functional BBS10 protein. In a number of embodiments, the ciliopathy gene has the nucleotide sequence of SEQ ID NO. 13 or has at least 74% sequence identity thereto, and encodes a functional BBS10 protein. In other embodiments, the ciliopathy gene has the nucleotide sequence of SEQ ID NO. 13 or has at least 76% sequence identity thereto, and encodes a functional BBS10 protein. In various embodiments, the ciliopathy gene has the nucleotide sequence of SEQ ID NO. 13 or has at least 78% sequence identity thereto, and encodes a functional BBS10 protein. In particular embodiments, the ciliopathy gene has the nucleotide sequence of SEQ ID NO. 13 or has at least 80% sequence identity thereto, and encodes a functional BBS10 protein. In certain embodiments, the ciliopathy gene has the nucleotide sequence of SEQ ID NO. 13 or has at least 82% sequence identity thereto, and encodes a functional BBS10 protein. In various embodiments, the ciliopathy gene has the nucleotide sequence of SEQ ID NO. 13 or has at least 84% sequence identity thereto, and encodes a functional BBS10 protein. In some embodiments, the ciliopathy gene has the nucleotide sequence of SEQ ID NO. 13 or has at least 85% sequence identity thereto, and encodes a functional BBS10 protein. In certain embodiments, the ciliopathy gene has the nucleotide sequence of SEQ ID NO. 13 or has at least 86% sequence identity thereto, and encodes a functional BBS10 protein. In a number of embodiments, the ciliopathy gene has the nucleotide sequence of SEQ ID NO. 13 or has at least 88% sequence identity thereto, and encodes a functional BBS10 protein. In other embodiments, the ciliopathy gene has the nucleotide sequence of SEQ ID NO. 13 or has at least 90% sequence identity thereto, and encodes a functional BBS10 protein. In certain embodiments, the ciliopathy gene has the nucleotide sequence of SEQ ID NO. 13 or has at least 92% sequence identity thereto, and encodes a functional BBS10 protein. In a number of embodiments, the ciliopathy gene has the nucleotide sequence of SEQ ID NO. 13 or has at least 94% sequence identity thereto, and encodes a functional BBS10 protein. In various embodiments, the ciliopathy gene has the nucleotide sequence of SEQ ID NO. 13 or has at least 95% sequence identity thereto, and encodes a functional BBS10 protein. In certain embodiments, the ciliopathy gene has the nucleotide sequence of SEQ ID NO. 13 or has at least 96% sequence identity thereto, and encodes a functional BBS10 protein. In some embodiments, the ciliopathy gene has the nucleotide sequence of SEQ ID NO. 13 or has at least 97% sequence identity thereto, and encodes a functional BBS10 protein. In a number of embodiments, the ciliopathy gene has the nucleotide sequence of SEQ ID NO. 13 or has at least 98% sequence identity thereto, and encodes a functional BBS10 protein. In some embodiments, the ciliopathy gene has the nucleotide sequence of SEQ ID NO. 13 or has at least 99% sequence identity thereto, and encodes a functional BBS10 protein. In particular embodiments, the ciliopathy gene has the nucleotide sequence of SEQ ID NO. 13.

In particular embodiments, the ciliopathy gene has the nucleotide sequence of SEQ ID NO. 14 or has at least 70% sequence identity thereto, and encodes a functional BBS10 protein. In some embodiments, the ciliopathy gene has the nucleotide sequence of SEQ ID NO. 14 or has at least 72% sequence identity thereto, and encodes a functional BBS10 protein. In a number of embodiments, the ciliopathy gene has the nucleotide sequence of SEQ ID NO. 14 or has at least 74% sequence identity thereto, and encodes a functional BBS10 protein. In other embodiments, the ciliopathy gene has the nucleotide sequence of SEQ ID NO. 14 or has at least 76% sequence identity thereto, and encodes a functional BBS10 protein. In various embodiments, the ciliopathy gene has the nucleotide sequence of SEQ ID NO. 14 or has at least 78% sequence identity thereto, and encodes a functional BBS10 protein. In particular embodiments, the ciliopathy gene has the nucleotide sequence of SEQ ID NO. 14 or has at least 80% sequence identity thereto, and encodes a functional BBS10 protein. In certain embodiments, the ciliopathy gene has the nucleotide sequence of SEQ ID NO. 14 or has at least 82% sequence identity thereto, and encodes a functional BBS10 protein. In various embodiments, the ciliopathy gene has the nucleotide sequence of SEQ ID NO. 14 or has at least 84% sequence identity thereto, and encodes a functional BBS10 protein. In some embodiments, the ciliopathy gene has the nucleotide sequence of SEQ ID NO. 14 or has at least 85% sequence identity thereto, and encodes a functional BBS10 protein. In certain embodiments, the ciliopathy gene has the nucleotide sequence of SEQ ID NO. 14 or has at least 86% sequence identity thereto, and encodes a functional BBS10 protein. In a number of embodiments, the ciliopathy gene has the nucleotide sequence of SEQ ID NO. 14 or has at least 88% sequence identity thereto, and encodes a functional BBS10 protein. In other embodiments, the ciliopathy gene has the nucleotide sequence of SEQ ID NO. 14 or has at least 90% sequence identity thereto, and encodes a functional BBS10 protein. In certain embodiments, the ciliopathy gene has the nucleotide sequence of SEQ ID NO. 14 or has at least 92% sequence identity thereto, and encodes a functional BBS10 protein. In a number of embodiments, the ciliopathy gene has the nucleotide sequence of SEQ ID NO. 14 or has at least 94% sequence identity thereto, and encodes a functional BBS10 protein. In various embodiments, the ciliopathy gene has the nucleotide sequence of SEQ ID NO. 14 or has at least 95% sequence identity thereto, and encodes a functional BBS10 protein. In certain embodiments, the ciliopathy gene has the nucleotide sequence of SEQ ID NO. 14 or has at least 96% sequence identity thereto, and encodes a functional BBS10 protein. In some embodiments, the ciliopathy gene has the nucleotide sequence of SEQ ID NO. 14 or has at least 97% sequence identity thereto, and encodes a functional BBS10 protein. In a number of embodiments, the ciliopathy gene has the nucleotide sequence of SEQ ID NO. 14 or has at least 98% sequence identity thereto, and encodes a functional BBS10 protein. In some embodiments, the ciliopathy gene has the nucleotide sequence of SEQ ID NO. 14 or has at least 99% sequence identity thereto, and encodes a functional BBS10 protein. In particular embodiments, the ciliopathy gene has the nucleotide sequence of SEQ ID NO. 14.

In various embodiments, the ciliopathy gene encodes a functional BBS1 protein having the protein sequence of SEQ ID NO 9 or at least 80% sequence identity thereto. In some embodiments, the functional BBS1 protein has the protein sequence of SEQ ID NO. 9 or at least 85% sequence identity thereto. In other embodiments, the functional BBS1 protein has the protein sequence of SEQ ID NO. 9 or at least 90% sequence identity thereto. In a number of embodiments, the functional BBS1 protein has the protein sequence of SEQ ID NO. 9 or at least 95% sequence identity thereto. In particular embodiments, the functional BBS1 protein has the protein sequence of SEQ ID NO. 9.

In other embodiments, the ciliopathy gene encodes a functional BBS10 protein having the protein sequence of SEQ ID NO 10 or at least 80% sequence identity thereto. In some embodiments, the functional BBS10 protein has the protein sequence of SEQ ID NO. 10 or at least 85% sequence identity thereto. In various embodiments, the functional BBS10 protein has the protein sequence of SEQ ID NO. 10 or at least 90% sequence identity thereto. In a number of embodiments, the functional BBS10 protein has the protein sequence of SEQ ID NO. 10 or at least 95% sequence identity thereto. In particular embodiments, the functional BBS10 protein has the protein sequence of SEQ ID NO. 10.

In the description above, the term "identity" is used to refer to the similarity of two sequences. For the purpose of this invention, it is defined here that in order to determine the percent identity of two sequences, the sequences are aligned for optimal comparison purposes (e.g., gaps can be introduced in the sequence of a first sequence for optimal alignment with a second amino or nucleic acid sequence). The nucleotide/amino acid residues at each position are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Generally, the two sequences are the same length. A sequence comparison is typically carried out over the entire length of the two sequences being compared.

The skilled person will be aware of the fact that several different computer programs are available to determine the identity between two sequences. For instance, a comparison of sequences and determination of percent identity between two sequences can be accomplished using a mathematical algorithm. In a preferred embodiment, the percent identity between two nucleic acid sequences is determined using the sequence alignment software Clone Manager 9 (Sci-Ed software—scied.com) using global DNA alignment; parameters: both strands; scoring matrix: linear (mismatch 2, OpenGap 4, ExtGap 1).

Alternatively, the percent identity between two amino acid or nucleic acid sequences can be determined using the Needleman and Wunsch (1970) algorithm which has been incorporated into the GAP program in the Accelrys GCG software package (available at accelrys.com/products/gcg/), using either a Blosum 62 matrix or a PAM250 matrix, and a gap weight of 16, 14, 12, 10, 8, 6, or 4 and a length weight of 1, 2, 3, 4, 5, or 6. A further method to assess the percent identity between two amino acid or nucleic acid sequences can be to use the BLAST sequence comparison tool available on the National Center for Biotechnology Information (NCBI) website (blast.ncbi.nlm.nih.gov), for example using BLASTn for nucleotide sequences or BLASTp for amino acid sequences using the default parameters.

The ciliopathy gene encodes a 'functional' protein. This means that the protein, when expressed, has the same function and activity as the wild type human protein. This could easily be determined by one skilled in the art. The protein encoded by the ciliopathy gene may be the wild type human protein. The wild type human sequence of the various proteins discussed above are well known to those skilled in the art. For example, they can be found on the publically accessible databases of the National Center for Biotechnology Information. Further, the nucleotide sequences which encode these proteins (and which would be contained in the vector) could readily be found or determined by a person skilled in the art, for example, using the genetic code which correlates particular nucleotide codons with particular amino acids.

The promoter contained in the vector is a ubiquitous promoter which is operably linked to the ciliopathy gene so that the promoter directs expression of the ciliopathy gene in the transduced organs. A ubiquitous promoter is one which is strongly active in a wide range of cells and tissues and provides constitutive expression. Suitable ubiquitous promoters are well known to those skilled in the art. A ubiquitous promoter is not tissue specific. It provides expression in multiple tissues/organs. The ubiquitous promoter results in expression of the ciliopathy gene in the transduced organs so that the expressed protein ameliorates the pathologies associated with the ciliopathy.

Suitable ubiquitous promoters include short elongation factor promoter (EFS), CAG promoter, cytomegalovirus immediate-early promoter (CMV), Ubiquitin C promoter (UBC), phosphoglycerate kinase promoter (PGK) and beta-actin promoter, e.g. chicken beta-actin promoter (CBA). These promoters are well known to one skilled in the art. Examples of the sequences of these promoters are given as SEQ ID NO. 3, SEQ ID NO. 4, SEQ ID NO. 5, SEQ ID NO. 6, SEQ ID NO. 7, SEQ ID NO. 8 and SEQ ID NO. 45. Therefore, in some embodiments, the promoter has a sequence selected from SEQ ID NO. 3, SEQ ID NO. 4, SEQ ID NO. 5, SEQ ID NO. 6, SEQ ID NO. 7, SEQ ID NO. 8 and SEQ ID NO. 45.

In particular embodiments, the promoter is an EFS promoter which may have the nucleotide sequence of SEQ ID NO. 3 or SEQ ID NO. 46.

In some embodiments, the promoter is a CAG promoter which may have the nucleotide sequence of SEQ ID NO. 4 or SEQ ID NO. 47.

In various embodiments, the promoter is a CMV promoter which may have the nucleotide sequence of SEQ ID NO. 6 or SEQ ID NO. 45.

In certain embodiments, the promoter is a UBC promoter which may have the nucleotide sequence of SEQ ID NO. 5 or SEQ ID NO. 48.

In a number of embodiments, the promoter is a PGK promoter which may have the nucleotide sequence of SEQ ID NO. 7.

In several embodiments, the promoter is a beta-actin promoter which may have the nucleotide sequence of SEQ ID NO. 8 or SEQ ID NO. 49.

In terms of particular combinations of elements, the vector may comprise an EFS promoter operably linked to a BBS1 gene, the vector being for the treatment of Bardet-Biedl syndrome. The BBS1 gene may be selected from SEQ ID NOs. 1, 11 and 12. For example, the vector may comprise the sequence of one of SEQ ID NOs. 15, 16 and 17. Alternatively, the vector may comprise an EFS promoter operably linked to a BBS10 gene, the vector being for the treatment of Bardet-Biedl syndrome. The BBS10 gene may be selected from SEQ ID NOs. 2, 13 and 14. For example, the vector may comprise the sequence of one of SEQ ID NOs. 30, 31 and 32.

The vector may comprise a UBC promoter operably linked to a BBS1 gene, the vector being for the treatment of Bardet-Biedl syndrome. The BBS1 gene may be selected from SEQ ID NOs. 1, 11 and 12. For example, the vector may comprise the sequence of one of SEQ ID NOs. 18, 19 and 20. Alternatively, the vector may comprise a UBC promoter operably linked to a BBS10 gene, the vector being for the treatment of Bardet-Biedl syndrome. The BBS10 gene may be selected from SEQ ID NOs. 2, 13 and 14. For example, the vector may comprise the sequence of one of SEQ ID NOs. 33, 34 and 35.

The vector may comprise a CMV promoter operably linked to a BBS1 gene, the vector being for the treatment of Bardet-Biedl syndrome. The BBS1 gene may be selected from SEQ ID NOs. 1, 11 and 12. For example, the vector may comprise the sequence of one of SEQ ID NOs. 21, 22 and 23. Alternatively, the vector may comprise a CMV promoter operably linked to a BBS10 gene, the vector being for the treatment of Bardet-Biedl syndrome. The BBS10 gene may be selected from SEQ ID NOs. 2, 13 and 14. For example, the vector may comprise the sequence of one of SEQ ID NOs. 36, 37 and 38.

The vector may comprise a CBA promoter operably linked to a BBS1 gene, the vector being for the treatment of Bardet-Biedl syndrome. The BBS1 gene may be selected from SEQ ID NOs. 1, 11 and 12. For example, the vector may comprise the sequence of one of SEQ ID NOs. 24, 25 and 26. Alternatively, the vector may comprise a CBA promoter operably linked to a BBS10 gene, the vector being for the treatment of Bardet-Biedl syndrome. The BBS10 gene may be selected from SEQ ID NOs. 2, 13 and 14. For example, the vector may comprise the sequence of one of SEQ ID NOs. 39, 40 and 41.

The vector may comprise a CAG promoter operably linked to a BBS1 gene, the vector being for the treatment of Bardet-Biedl syndrome. The BBS1 gene may be selected from SEQ ID NOs. 1, 11 and 12. For example, the vector may comprise the sequence of one of SEQ ID NOs. 27, 28 and 29. Alternatively, the vector may comprise a CAG promoter operably linked to a BBS10 gene, the vector being for the treatment of Bardet-Biedl syndrome. The BBS10 gene may be selected from SEQ ID NOs. 2, 13 and 14. For example, the vector may comprise the sequence of one of SEQ ID NOs. 42, 43 and 44.

The vector may comprise a PGK promoter operably linked to a BBS1 gene, the vector being for the treatment of Bardet-Biedl syndrome. The BBS1 gene may be selected from SEQ ID NOs. 1, 11 and 12. Alternatively, the vector may comprise a PGK promoter operably linked to a BBS10 gene, the vector being for the treatment of Bardet-Biedl syndrome. The BBS10 gene may be selected from SEQ ID NOs. 2, 13 and 14.

The vector described above can provide transduction of the ciliopathy gene into multiple organs. This can be any suitable vector and such vectors are well known to those skilled in the art. In particular embodiments, the vector can cross the blood brain barrier. This allows transduction to occur in the brain and nervous system including the eye, and also in the visceral organs and musculature. Therefore, a single vector can be used to provide gene expression in multiple organs to ameliorate the pathologies associated with the ciliopathy. This gene expression may be systemic as it can occur in multiple sites throughout the body. Further, administration of the vector by a limited number of routes can be used to provide systemic gene expression to ameliorate the pathologies associated with the ciliopathy throughout the body. This means that it is not necessary to treat each affected tissue individually. This approach targeting multiple organs at once has not been used previously in ciliopathies and it was not contemplated that such an approach would work.

The organs that can be transduced with the vector described above may be selected from the central nervous system, eye (e.g. retinal photoreceptors and retinal pigmented epithelium), heart, liver, muscle, pancreas, spleen, lung and kidney. Therefore, in some embodiments, the vector provides transduction of the ciliopathy gene into multiple organs selected from the central nervous system, eye, heart, liver, muscle, pancreas, spleen, lung and kidney. In other embodiments, the vector provides transduction of the ciliopathy gene into at least three organs selected from the central nervous system, eye, heart, liver, muscle, pancreas, spleen, lung and kidney. In various embodiments, the vector provides transduction of the ciliopathy gene into at least four of the stated organs. In a number of embodiments, the vector provides transduction of the ciliopathy gene into at least five of the stated organs. In some embodiments, the vector provides transduction of the ciliopathy gene into at least six of the stated organs. In other embodiments, the vector provides transduction of the ciliopathy gene into at least seven of the stated organs. In various embodiments, the vector provides transduction of the ciliopathy gene into at least eight of the stated organs. In particular embodiments, the vector provides transduction of the ciliopathy gene into the central nervous system, eye, heart, liver, muscle, pancreas, spleen, lung and kidney. In certain embodiments, the vector provides transduction of the ciliopathy gene into at least the central nervous system (e.g. the brain) and the eye. In various embodiments, the vector provides transduction of the ciliopathy gene into at least the central nervous system (e.g. the brain), the eye, and one of the liver, kidney and spleen. In some embodiments, the vector provides transduction of the ciliopathy gene into at least the central nervous system (e.g. the brain), the eye and the liver. In particular embodiments, the vector provides transduction of the ciliopathy gene into at least the central nervous system (e.g. the brain), the eye, the liver, the kidney and the spleen.

Suitable vectors include adeno-associated virus-8 (AAV8) and adeno-associated virus-9 (AAV9) and also other AAVs (e.g. AAV2) which have been pseudotyped with the capsid proteins from AAV8 or AAV9. Such vectors are described in WO 2005/033321. Other suitable vectors include AAV-PHP.A and AAVPHP.B (Nature Biotechnology 34, 204-209 (2016)), AAV9.47 (Hum Gene Ther. 2016 July;27(7):497-508), AAV-B1 (Mol. Ther. 24, 1247-1257), AAV8 (Y733F) (Mol Ther 2009; 17: 463-471) and AAV2-TT (described in WO2015/121501). Lentiviral vectors can also be used, for example, as described in Trends in Molecular Medicine, April 2016, Vol. 22, No. 4 and Ther Deliv. 2010 October; 1(4): 517-534.

In some embodiments, the vector is an AAV vector such as AAV8, AAV9, AAV vectors pseudotyped with the capsid proteins from AAV8 or AAV9, AAV-PHP.A, AAV-PHP.B, AAV9.47, AAV-B1, AAV8 (Y733F) or AAV2-TT. In other embodiments, the vector is selected from AAV8, AAV9, AAV vectors pseudotyped with the capsid proteins from AAV8 or AAV9, AAV-PHP.A, AAV-PHP.B, AAV9.47 and AAV-B1. In various embodiments, the vector is selected from AAV8, AAV9, AAV vectors pseudotyped with the capsid proteins from AAV8 or AAV9, AAV-PHP.A and AAV-PHP.B. In a number of embodiments, the vector is selected from AAV8, AAV9, AAV vectors pseudotyped with the capsid proteins from AAV8 or AAV9, and AAV-PHP.B. In particular embodiments, the vector is selected from AAV8, AAV9, and AAV vectors pseudotyped with the capsid proteins from AAV8 or AAV9. In some embodiments, the vector is selected from AAV8 and AAV vectors pseudotyped with the capsid proteins from AAV8 (e.g. AAV2 pseudotyped with the capsid proteins from AAV8 (AAV2/8)). In other embodiments, the vector is selected from AAV9 and AAV vectors pseudotyped with the capsid proteins from AAV9 (e.g. AAV2 pseudotyped with the capsid proteins from AAV9 (AAV2/9)).

The adeno-associated viral vector may be a recombinant adeno-associated viral (rAAV) vector. AAV is a member of the family Parvoviridae which is described in Kenneth I. Berns, "Parvoviridae: The Viruses and Their Replication," Chapter 69 in Fields Virology (3d Ed. 1996).

The genomic organization of all known AAV serotypes is very similar. The genome of AAV is a linear, single-stranded DNA molecule that is less than about 5,000 nucleotides (nt) in length. Inverted terminal repeats (ITRs) flank the unique coding nucleotide sequences for the non-structural replication (Rep) proteins and the structural (VP) proteins. The VP proteins (VP1, -2 and -3) form the capsid. The terminal 145 nt are self-complementary and are organized so that an energetically stable intramolecular duplex forming a T-shaped hairpin may be formed. These hairpin structures function as an origin for viral DNA replication, serving as primers for the cellular DNA polymerase complex. Following wild type (wt) AAV infection in mammalian cells the Rep genes (i.e. encoding Rep78 and Rep52 proteins) are expressed from the P5 promoter and the P19 promoter, respectively, and both Rep proteins have a function in the replication of the viral genome. A splicing event in the Rep ORF results in the expression of actually four Rep proteins (i.e. Rep78, Rep68, Rep52 and Rep40). However, it has been shown that the unspliced mRNA, encoding Rep78 and Rep52 proteins, in mammalian cells are sufficient for AAV vector production. Also in insect cells the Rep78 and Rep52 proteins suffice for AAV vector production.

In an AAV suitable for use as a gene therapy vector, the vector genome typically comprises a nucleic acid (e.g. a ciliopathy gene) to be packaged for delivery to a target cell. According to this particular embodiment, the heterologous nucleotide sequence is located between the viral ITRs at either end of the vector genome. In further preferred embodiments, the parvovirus (e.g. AAV) cap genes and parvovirus (e.g. AAV) rep genes are deleted from the template genome (and thus from the virion DNA produced therefrom). This configuration maximizes the size of the nucleic acid sequence(s) that can be carried by the parvovirus capsid.

According to this particular embodiment, the nucleic acid is located between the viral ITRs at either end of the substrate. It is possible for a parvoviral genome to function with only one ITR. Thus, in a gene therapy vector based on a parvovirus, the vector genome is flanked by at least one ITR, but, more typically, by two AAV ITRs (generally with one either side of the vector genome, i.e. one at the 5' end and one at the 3' end). There may be intervening sequences between the nucleic acid in the vector genome and one or more of the ITRs.

Generally, the ciliopathy gene (i.e. the nucleotide sequence encoding a functional protein corresponding to the protein that is mutated in the ciliopathy (for expression in the mammalian cell)) will be incorporated into a parvoviral genome located between two regular ITRs or located on either side of an ITR engineered with two D regions.

In one aspect, the invention provides a pharmaceutical composition comprising a vector as described above and one or more pharmaceutically acceptable excipients. The one or more excipients include carriers, diluents and/or other medicinal agents, pharmaceutical agents or adjuvants, etc.

The invention also provides a method of treating a ciliopathy comprising administering a therapeutically effective amount of a vector as described above to a patient suffering from a ciliopathy. Preferably, the patient is human.

When the ciliopathy is "treated" in the above method, this means that one or more symptoms of the ciliopathy are ameliorated. It does not mean that the symptoms are completely remedied so that they are no longer present in the patient, although in some methods, this may be the case. The method of treating results in one or more of the symptoms of the ciliopathy being less severe than before treatment. The method of treating may result in a plurality of the symptoms of the ciliopathy being less severe than before treatment. The amelioration of the symptoms occurs in multiple organs due to transduction and gene expression in multiple organs.

A "therapeutically effective amount" refers to an amount effective, at dosages and for periods of time necessary, to achieve the desired therapeutic result, such as raising the level of functional protein in a subject (so as to lead to a level sufficient to ameliorate the symptoms of the ciliopathy).

The method of treatment causes an increase in the level of functional protein in the subject. In some embodiments, the method of treatment causes an increase in the level of functional protein to about a normal level (i.e. the level found in a normal healthy subject). In one embodiment, the method of treatment causes an increase in the level of functional protein to, at most, normal levels.

The vector may be administered in any suitable way so as to allow expression of the ciliopathy gene in multiple organs. In particular embodiments, a single administration of the vector can be used to provide gene expression to ameliorate the pathologies associated with the ciliopathy. Administration of the vector may provide systemic gene expression to ameliorate the pathologies associated with the ciliopathy throughout the body. The vector may be administered intravenously or intracranially. In particular embodiments, the vector is administered intravenously. In some embodiments, the vector is administered intracranially. In various embodiments, the vector is administered intravenously and intracranially.

The vector may be administered intrathecally. This can be alone or in addition to intravenous and/or intracranial administration.

Intracranial administration is the direct delivery of the vector to specific areas of the brain by means of a stereotaxic injection. Intracranial administration does not include subretinal administration, e.g. subretinal injection.

Further, the vector should preferably not be administered intranasally. The nasal route of administration can restrict expression of the vector to a small subset of nasal cells and does not allow the vector to target the main affected tissues in other parts of the body. In addition, the nasal route does not allow long term sustained expression of the transgene due to rapid replacement of the small subset of nasal cells.

If the vector is administered by multiple routes of administration, for example, intravenously and intracranially, the vector is administered at both sites on the same day. In some embodiments, the multiple administrations are given within the space of six hours, within the space of four hours, or even within the space of two hours. In some embodiments, the multiple administrations are given simultaneously.

The vector may be administered at a single point in time. For example, a single injection may be given. If the vector is administered by multiple routes of administration, for example, intravenously and intracranially, the vector is administered at both sites only once (and at least on the same day as described above). No further administrations are given subsequently.

Further, the invention provides the vector described above for use in therapy, for example, in the treatment of a ciliopathy.

In addition, the invention provides the use of the vector as described above in the manufacture of a medicament for treating a ciliopathy.

All patent and literature references cited in the present specification are hereby incorporated by reference in their entirety.

BRIEF DESCRIPTION OF THE DRAWINGS

The invention will now be described in detail by way of example only with reference to the figures which are as follows.

DETAILED DESCRIPTION OF THE INVENTION

Figure 1:
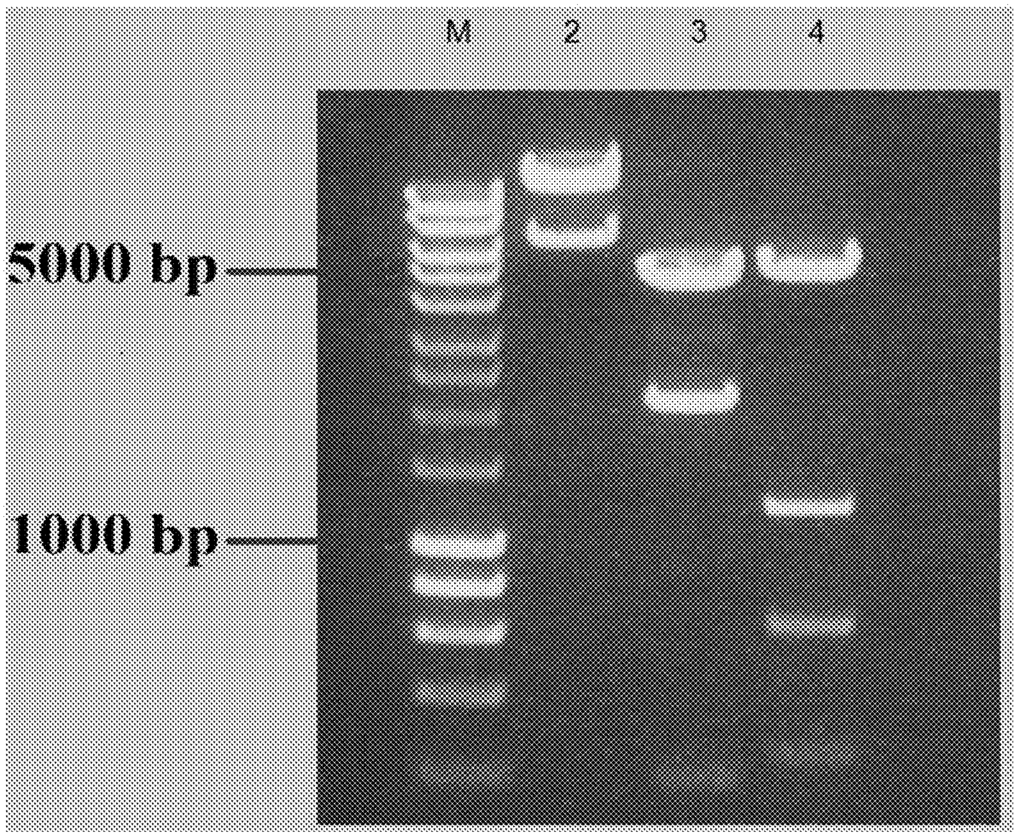
FIG. 1: Restriction digestion. Plasmid DNA of AAV2/8, Helper Virus and BBS1 Digested Using Xho1. Gel electrophoresis showing plasmid DNA of each helper plasmid (pHGTI, lane 2), AAV2/8 plasmid (pLT-AAV2/8, lane 3) and BBS1 plasmid (pAV-EFS-BBS1, lane 4) digested with restriction enzyme Xho1 on 1% agarose gel. HyperLadder is seen in lane 1. Plasmids were used to create hAAV2/8-EFS-BBS1. The band sizes for the helper plasmid were 6318 bp and 11549 bp (lane 2) and for the AAV2/8 plasmid, 186 bp, 2109 bp and 4844 bp (lane 3), respectively. For pAV-EFS-BBS1, the band sizes were 236 bp, 643 bp, 1195 bp and 5078 bp (lane 4).

The inventors have developed a single vector which is administered by a simple injection and which targets multiple organs at once. This approach is simpler and certainly more cost-effective than an alternative multi-vector approach. Restoring function in more than one organ (e.g. vision and weight lowering) would be life-changing by improving the health and quality-of-life of ciliopathy patients.

Given the broad range of organ involvement in ciliopathies, a multi-organ therapy is required that would address both the central nervous system and visceral symptoms. Furthermore, the early appearance of symptoms in patients in infancy would ideally require such therapy to be administered as early as possible. The delivery of a single-therapy during the neonatal period will target multiple organs effectively, prevent irreversible pathology and be cost-effective.

To achieve these aims, the inventors have used a gene therapy based protocol that utilises the adeno-associated virus to achieve multi-organ therapy. Until recently, multi-organ gene delivery had been difficult due to the inability to find viral vectors that can target peripheral organs and cross the blood-brain barrier. However, the discovery that AAV8 and AAV9 can cross the blood-brain barrier and mediate highly efficient gene delivery to the central nervous system of mice (Foust K D et al. Nat Biotechnol. 2009; 27(1):59-65) and non-human primates (Foust K D et al. Nat Biotechnol. 2010; 28(3): 271-4; Bevan A K et al. Mol Ther. 2011; 19(11): 1971-80) has changed the field's perspective. It is now feasible to consider simplifying the administration of vectors so that multiple organs can be treated with fewer routes of administration rather than using a one administration per organ regime. For example, it has been demonstrated that intravenous administration of AAV8 or AAV9 carrying the green fluorescent protein (GFP) gene to newborn mice leads to extensive and global transduction of the brain and nervous system including the eye. Furthermore, the inventors have data showing that this approach also leads to extensive systemic transduction including the visceral organs and musculature (FASEB J. 2015 September;29(9):3876-88).

A multisystem and progressive disorder that presents symptoms in infancy such as Bardet-Biedl Syndrome is an ideal candidate for neonatal therapeutic AAV delivery. As the most common mutations causing BBS are found in BBS1, the inventors have tested an AAV8 and AAV9 vector carrying the human gene BBS1 in one BBS murine model of disease, Bbs1$^{M390R/M390R}$. This model is a "knock-in" of the common mutation and is well validated and characterised to recapitulate the human BBS phenotype (including blindness and obesity). Transcription of the exogenous BBS1 gene is driven by the mammalian ubiquitous EFS promoter, widely expressed in targeted organs. This approach exploits the capability of AAV8 and AAV9 to cross the blood brain barrier, where neuronal defects such as the retina, the hippocampus/dentate gyrus or the hypothalamic appetite centre can then be targeted, hence restoring retinal function and obesity respectively. Successful systemic gene transfer in these disease models provides the necessary proof-of-principle, optimal dosage information, efficacy of restitution, and toxicity and safety profiles of the vectors in advance of clinical trials for patients.

The inventors cloned the human BBS1 cDNA under the control of the short elongation factor promoter (EFS) into an AAV-2 vector pseudotyped with the capsid proteins from adeno-associated virus-8 (AAV2/8). These data demonstrate the EFS-BBS1 construct efficiently transfects and expresses human BBS1 in HEK293T cells. After viral production and infection via intracranial delivery or systemic (IV) delivery of P0 pups, good transduction was shown in the retina and brain. No toxicological effect in treated mice were observed. The inventors were able to demonstrate the obesity and retinal phenotype can be rescued to a high degree when mutant Bbs1$^{M390R/M390R}$ animals were treated.

The BBS1 nucleotide and amino acid sequence is highly conserved between human and mouse (92.2%). A knock-in mouse was produced carrying the M390R mutation in the Bbs1 gene—the most common mutation in patients (Proc Natl Acad Sci USA. 2007 Dec. 4; 104(49): 19422-19427). Sequential histology of the Bbs1$^{M390R/M390R}$ mice retinae shows progressive degeneration, of inner and outer segments (IS and OS), that is slow and complete by 6 months after birth. Electroretinograms (ERG) of Bbs1$^{M390R/M390R}$ knock-in mice show significant attenuation in the a- and b-waves and a lower attenuation of the c-waves, suggesting the degeneration predominantly affects cone and rod photoreceptor cells and not the retinal pigmented epithelium (RPE). In addition, Bbs1$^{M390R/M390R}$ mice also develop obesity associated with high serum levels of adipocyte-derived leptin hormone suggesting leptin resistance, increased food intake and decreased locomotor activity. Also, numerous neuroanatomical defects are detected including a reduction in the size of the corpus striatum and hippocampus, areas important in cognition and learning. These phenotypes recapitulate the human disease making the mouse model ideal for assessing novel treatments. Both mouse Bbs10 and human BBS10 genes are encoded by two exons. Their proteins are conserved with 67% identical amino acid sequences. The Bbs10 null (Bbs10$^{-}$/–) mouse is lacking completely exon 2 of Bbs10. Bbs10$^{-/-}$ mice display typical BBS phenotype with a perinatal period with a runting and with an obesity onset from 8 onwards and are overweight at the third month of life. Bbs10$^{-/-}$ mice also develop hyperphagia and high levels of circulating leptin. Bbs10$^{-/-}$ mice develop severe retinal degeneration, with a clear loss of the inner IS and OS of the photoreceptors and the ONL by 3 months of age (*Cilia* 2015 4:10).

Materials and Methods

A construct has been produced where human BBS1 cDNA (SEQ ID NO. 1—NM_024649.4) has been cloned under the control of the EFS promoter (Human eukaryotic translation elongation factor 1 α1 short promoter) in an AAV2/8 viral plasmid. As the aim of the project was to move towards viral gene therapy for Bardet-Biedl syndrome 1 (BBS1), an adeno-associated virus (AAV) containing the human wild-type BBS1 cDNA and driven by an elongation factor-1α short (EFS) promoter was produced. For virus production, usual methods were used. 4000 $cm^2$ of HEK293T cell monolayer cells were transfected with the EFS-BBS1-AAV-ITR containing plasmid, AAV2 Rep-Cap plasmid and the helper plasmid. Once showing cytopathic effects, cells were harvested and lysed to release the virus. The adeno-associated virus was purified by centrifugation using two sequential caesium chloride gradients. The final product was desalted, titered both spectrophotometrically for viral particles and plaque formation assay for PFU/IFU.

The inventors also cloned BBS10 wild-type cDNA (SEQ ID NO. 2) under the control of the EFS promoter, and also completely novel codon optimised sequences for BBS1 (SEQ ID NOs. 11 and 12) and BBS10 (SEQ ID NOs. 13 and 14) to improve levels of gene expression and efficacy. Novel sequences were cloned under the control of EFS, CAG, CMV, CBA, UBC promoters. All possible combinations of the described promoters and described BBS1 and BBS10 sequences were cloned into pAV-AAV-ITR containing plasmids. Promoters were cloned between SpeI and EcoRI restriction sites, followed by inserting the BBS coding sequences, 3' downstream from the promoters, with EcoRI and SalI restriction enzymes. Clones were sequenced to check unwanted mutations in promoter and coding regions. All sequences containing the promoter and gene sequence are set out as SEQ ID NO. 15 to SEQ ID NO. 44.

To test improved gene expression, HEK293T cells were transfected with all different constructs; pAV-EFS-WTBBS1, pAV-EFS-COSEQ1-BBS1, pAV-EFS-COSEQ2-BBS1, pAV-UBC-WTBBS1, pAV-UBC-COSEQ1-BBS1, pAV-UBC-COSEQ2-BBS1, pAV-CMV-WTBBS1, pAV-CMV-COSEQ1-BBS1, pAV-CMV-COSEQ2-BBS1, pAV-CBA-WTBBS1, pAV-CBA-COSEQ1-BBS1, pAV-CBA-COSEQ2-BBS1, pAV-CAG-WTBBS1, pAV-CAG-COSEQ1-BBS1, pAV-CAG-COSEQ2-BBS1, pAV-EFS-WTBBS10, pAV-EFS-COSEQ1-BBS10, pAV-EFS-COSEQ2-BBS10, pAV-UBC-WTBBS10, pAV-UBC-COSEQ1-BBS10, pAV-UBC-COSEQ2-BBS10, pAV-CMV-WTBBS10, pAV-CMV-COSEQ1-BBS10, pAV-CMV-COSEQ2-BBS10, pAV-CBA-WTBBS10, pAV-CBA-COSEQ1-BBS10, pAV-CBA-COSEQ2-BBS10, pAV-CAG-WTBBS10, pAV-CAG-COSEQ1-BBS10, pAV-CAG-COSEQ2-BBS10, using 1 μg/μl of DNA, using a Lipofectamine 2000 protocol.

Cells were harvested for total mRNA with 0.5 ml of Trizol. Total mRNA was quantified and Real Time PCR was performed using 1 g of mRNA for each transfection. Specific primers for each sequence were used for each construct to quantify levels of human BBS1 expression. Ct values Expression levels were normalised for EFS-BBS1 for all BBS constructs and for untransfected samples for BBS10 constructs.

In a separate experiment, cells were also transfected for BBS1 protein expression. RIPA Buffer was used to extract total protein and total protein quantified for each transfection. 1 μg/μl of sample protein for each transfection was loaded in a 4-20% acrylamide gel. A western blot was performed with a specific antibody against BBS1 and the gel was scanned and analysed. As a loading control a second western blot was performed with a GAPDH antibody. Blots were quantified by normalising first for GAPDH, for each lane, and then to EFS-WTBBS1 expression, for each gel.

Virus Administration and Titer

Timed matings were prepared between $Bbs1^{M390R/+}$ males and $Bbs1^{M390R/+}$ females. P0 pups were genotyped for sex and Bbs1 genotype. The adenoviral-associated vector was given via two routes of administration in P0 animals a) intracranially (5 μl of $3.5\times10^{13}$ vg/ml (vector genomes/ml)) and systemically (IV) (20 μl of $3.5\times10^{13}$ vg/ml). Systemic injections were executed through the temporal face vein.

The inventors injected 3 different groups of animals; $Bbs1^{M390R/M390R}$ animals, wild-type and heterozygous. Uninjected controls have been used as a control for each group. A total of n=6 animals/group were used. Treated animals do not show any physical or behaviour distress after 6 months post-injection.

Based on the results with the codon optimised sequences and constructs, the inventors decided to test the capacity of the new constructs to deliver and express human BBS1 to different tissues. The authors tested a new virus capsid (AAV2/9), a new CAG promoter and the new CAG-COSEQ1-BBS1 construct (SEQ ID NO. 28). AAV2/9 vectors containing the CAG-COSEQ1-BBS1 construct (SEQ ID NO. 28) were produced and tested for effectiveness by dosing P0 neonatal pups to restore Bbs1 activity. $Bbs1^{M390R/M390R}$ neonates were injected intracranially with $0.175\times10^{12}$ vg per animal, in a 5 μl injection. Control, $Bbs1^{+/M390R}$ and WT animals were also injected with the AAV2/9-CAG-COSEQ1-BBS1 or vehicle and tested for human BBS1 expression at 14 and 40 days after injections.

Results

The inventors show for the first time the treatment of multiple tissues affected by a ciliopathy disorder, Bardet-Biedl Syndrome, using gene therapy techniques. The human BBS1 cDNA under the control of the ubiquitous promoter EFS transduced expression of BBS1 protein in an AAV2/8 vector. FIG. 1 show the right size after digestion of the cloned pAV-EFS-BBS1 (lane 4), demonstrating a correct cloning. In order to create this AAV, the producer plasmids pHGTI, pLT-AAV2-8, and pAV-EFS-BBS1 were obtained. The helper plasmid was pHGTI, which contains sequences coding for herpes simplex virus proteins. These are necessary for the efficient production of AAV. The pLT-AAV2-8 plasmid contains sequences coding for AAV rep and cap genes from AAV2 and AAV8, respectively. The rep gene is necessary for AAV replication, and the cap genes code for capsid proteins, which determine the tropism of the AAV. Finally, the pLT-AAV2-8 plasmid contains AAV inverted terminal repeat sequences, along with the BBS1 cDNA, which is controlled by the EFS promoter. It is these sequences that are packaged into the AAV and delivered to the cells.

To assess if the producer plasmids obtained were as expected, a restriction enzyme digest was carried out by digesting pLT-AAV2-8, pHGTI, and pAV-EFS-BBS1 plasmid DNA (FIG. 1). The band sizes of pLT-AAV2-8 plasmid were 186 bp, 2109 bp and 4844 bp, respectively (lane 3, FIG. 1). For the transgene pAV-EFS-BBS1 construct, the band sizes were 236 bp, 643 bp, 1195 bp and 5078 bp (lane 4, FIG. 1). For the helper plasmid, the band sizes visible were 6318 bp and 11549, respectively, (lane 2, FIG. 1) which verified that there was no additional, unwanted DNA present in the plasmids.

Figure 2:
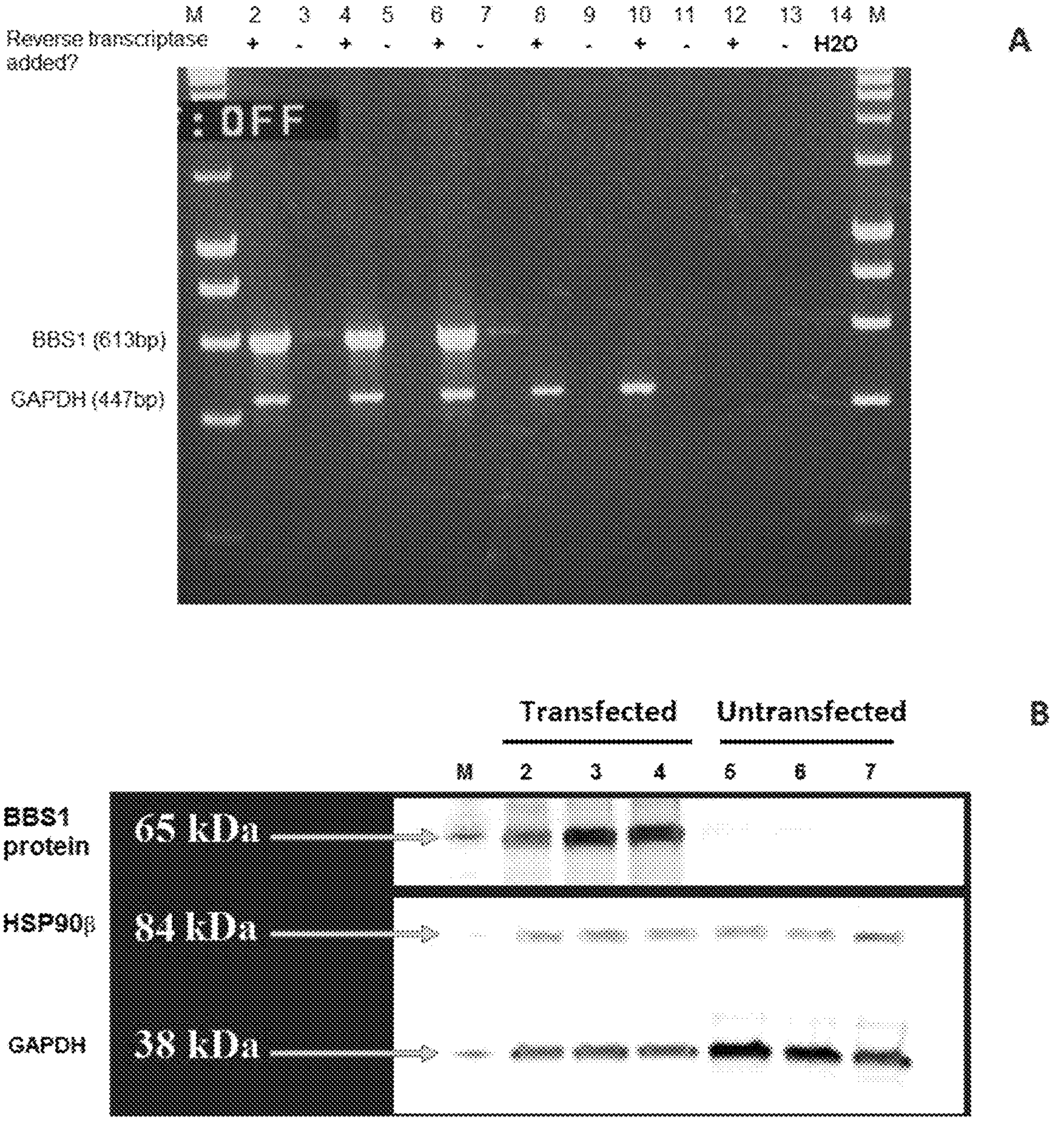
FIG. 2: human BBS1 Transfections of 293T Cells. Protein and mRNA expression following transfection of 293T with EFS-BBS1 plasmid. A) 2% agarose gel following reverse-transcription PCR from mRNA extracted from transfected and untransfected 293T cells. Lane 1 marker and lanes 2, 4 and 6 show transfected cDNA; lanes 3, 5 and 7, transfected cells without reverse transcription; lanes 8, 10 and 12, non-transfected cDNA; and lanes 9, 11 and 13, untransfected, no-reverse transcriptase controls. Lane 14 shows a ddH20 sample for PCR as the/a negative control. B) BBS1 protein expression following transfection was visible in 293T cells following transfection. Lanes 2, 3 and 4 are transfected cells, and lanes 5, 6 and 7 are untransfected. Protein expression of HSP90β and GAPDH was used as internal control.
Figure 3:
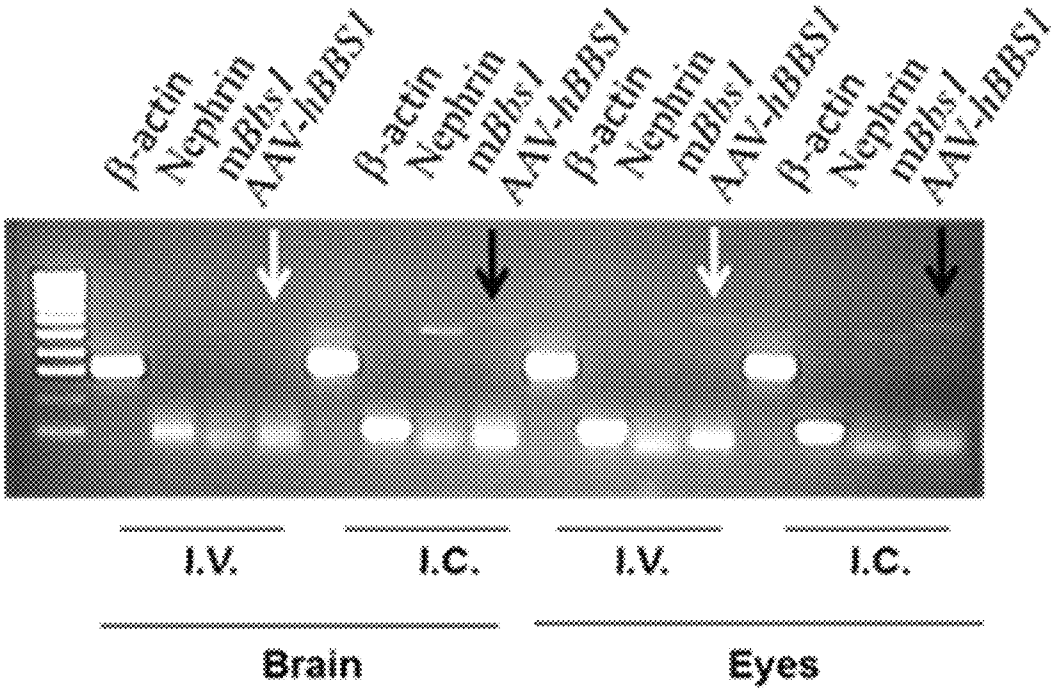
FIG. 3: Expression of human BBS1 in the retina and CNS (Central Nervous System). RT-PCR showing transgene human BBS1 expression. P35 animals after intracranial and systemic delivery. Intracranial injection of AAV2/8-EFS-BBS1 (I.C.) shows clear expression of human BBS1 alongside mouse Bbs1 in the brain and eye (black arrows), indicating good transduction and expression. A clear expression of human BBS1 is observed in the eyes of intravenously (systemically) injected animals (I.V.) (white arrows). Specific primers to differentiate mouse and human BBS1 were designed. mBbs1 (mouse Bbs1); AAV-hBBS1 (transduced human BBS1); β-actin (β-actin positive control); Nephrin (negative control).
Figure 4:
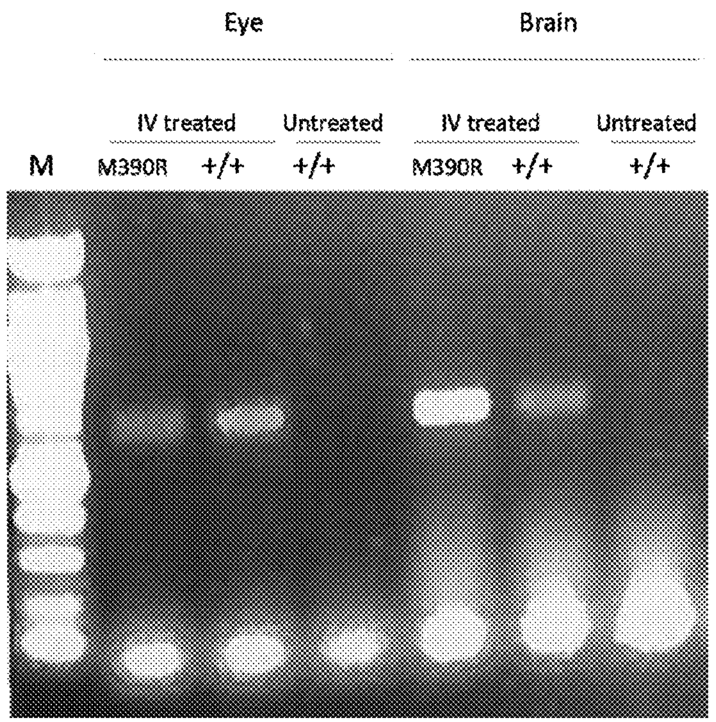
FIG. 4. Expression of human BBS1 by RT-PCR in the retina and CNS (Central Nervous System) at P180 (180 days post-injection) after P0 intracranial and systemic delivery in mice. A) A clear expression of human BBS1 is observed in the eyes and brain of intravenously (systemically) injected animals (I.V.). B) Intracranial injection of AAV2/8-EFS-BBS1 (I.C.) shows clear expression of human BBS1 in the brain, indicating good transduction and expression. Specific human primers to differentiate mouse and human BBS1 were designed. M390R=Bbs1$^{M390R/M390R}$ animals. +/+=Wild type animals. RT-=RT-PCR negative control.
Figure 4:
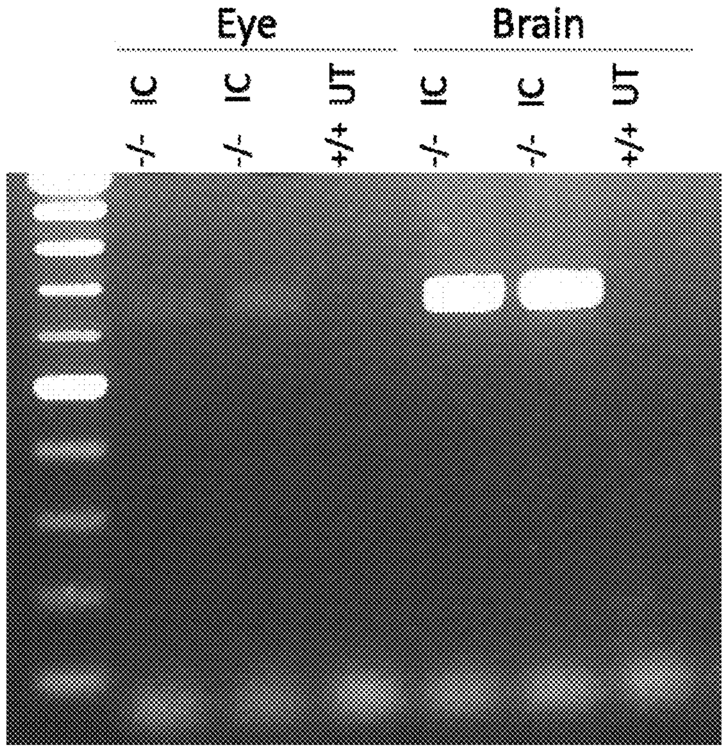

High expression of BBS1 was observed when HEK293T cells were transfected with pAV-EFS-BBS1 plasmid. This data shows that EFS is able to drive expression of human BBS1 in vitro (FIG. 2). The inventors produced and purified AAV2/8-EFS-BBS1 and injected P0 wild-type embryos with intracranial and systemic delivery. Transduction capacity of AAV2/8-EFS-BBS1 was demonstrated in both tissues, retina and brain. Specific expression of human BBS1 in the retina and brain expression was seen (FIG. 3, FIG. 4).

Figure 5:
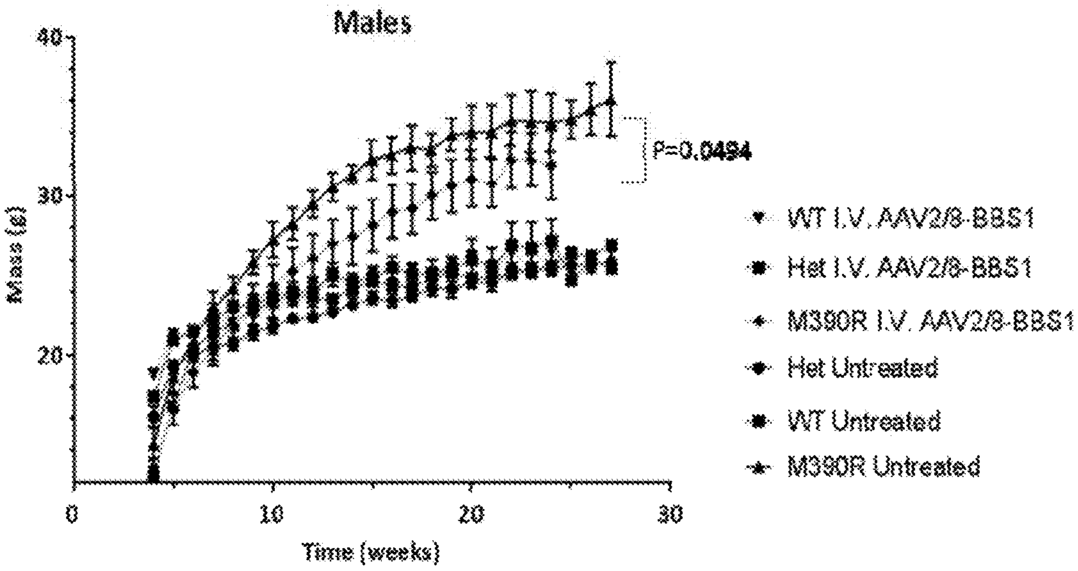
FIG. 5. Phenotypical expression in treated and untreated Bbs1$^{M390R/M390R}$ demonstrates reduction in weight in P0 intracranial treated animals. When treated intracranially with the AAV2/8 EFS-BBS1 construct, Bbs1$^{M390R/M390R}$ animals show statistically significant recovery of weight back to wild-type levels (see p-values) in males and females. IC=Intracranial. Het=Heterozygous animals, Bbs1$^{M390R/M390R}$. WT=Wild-type animals. M390R=Homozygous animal Bbs1$^{M390R/M390R}$. Error Bars show Standard error of the Mean (S.E.M). p-values were obtained after non-linear curve fitting, (Gompertz growth curve fitting), followed by ANOVA and Tukey's test.
Figure 5:
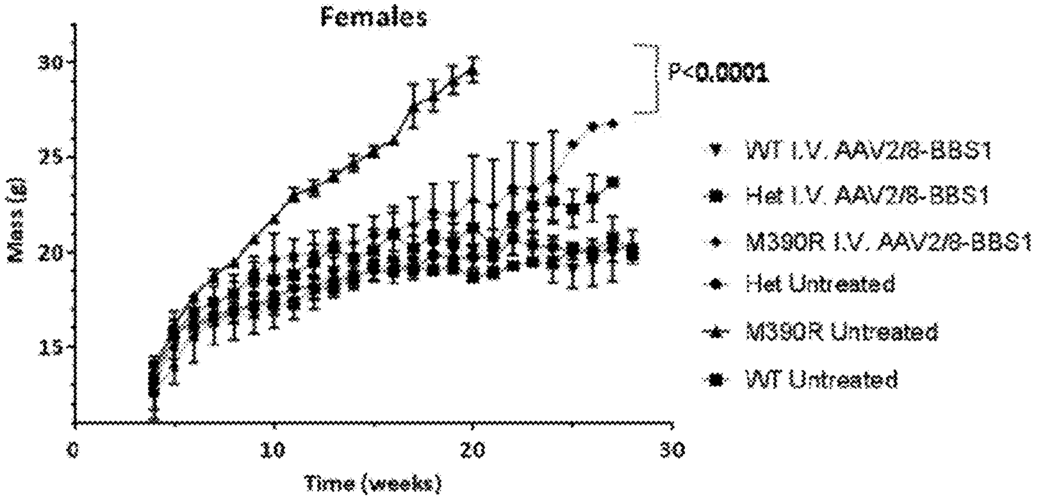
Figure 6:
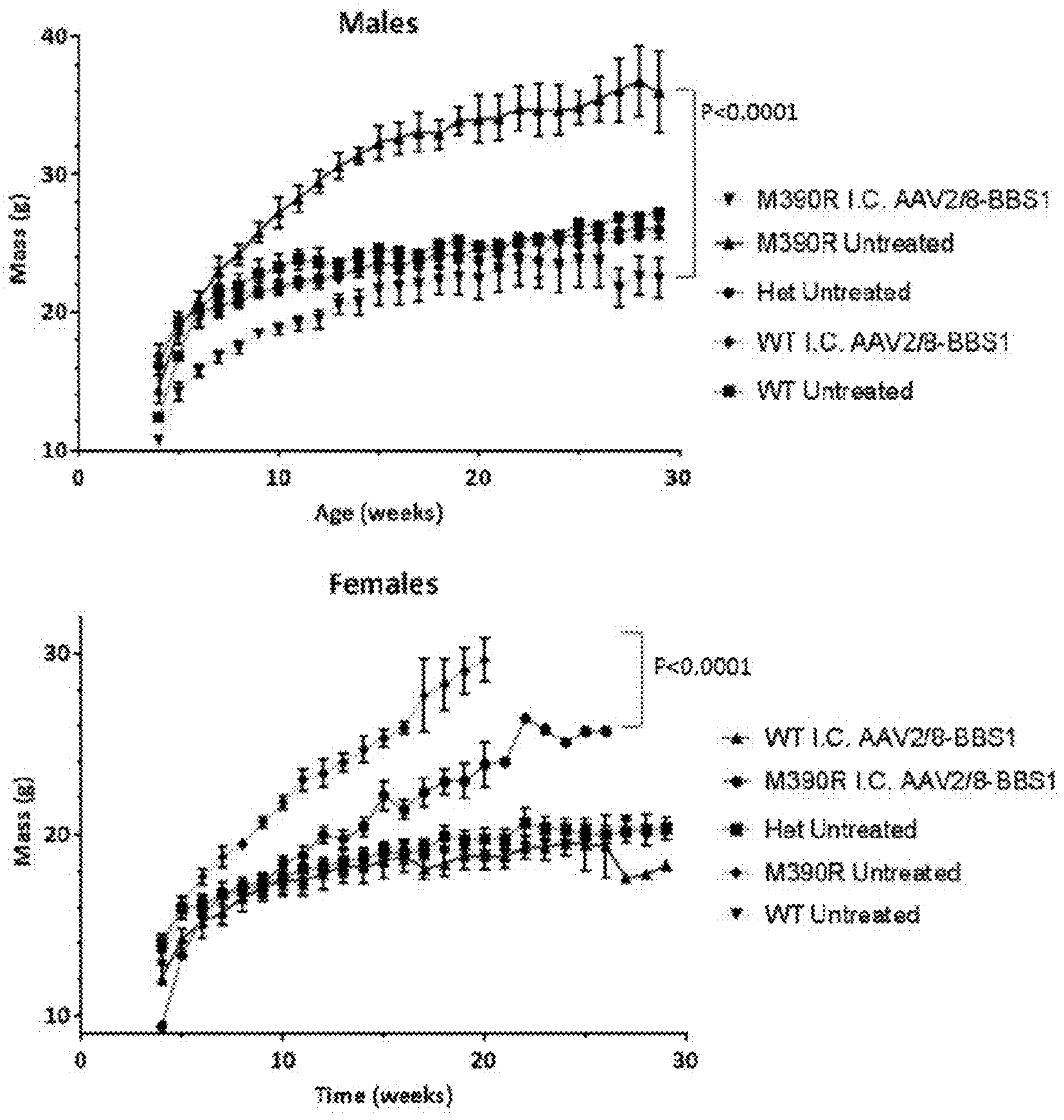
FIG. 6. Phenotypical expression in treated and untreated Bbs1$^{M390R/M390R}$ demonstrates reduction in weight in P0 systemically treated animals. When treated intravenously with AAV2/8 EFS-BBS1 construct, Bbs1$^{M390R/M390R}$ animals show an attenuated weight gain to wild-type levels (see p-values) in males and females. IV=Intravenous. Het=Heterozygous animals, Bbs1$^{M390R/M390R}$. WT=Wild-type animals. M390R=Homozygous animal Bbs1$^{M390R/M390R}$. Error Bars show Standard error of the Mean (S.E.M). p-values were obtained after non-linear curve fitting, (Gompertz growth curve fitting), followed by ANOVA and Tukey's test.
Figure 7:
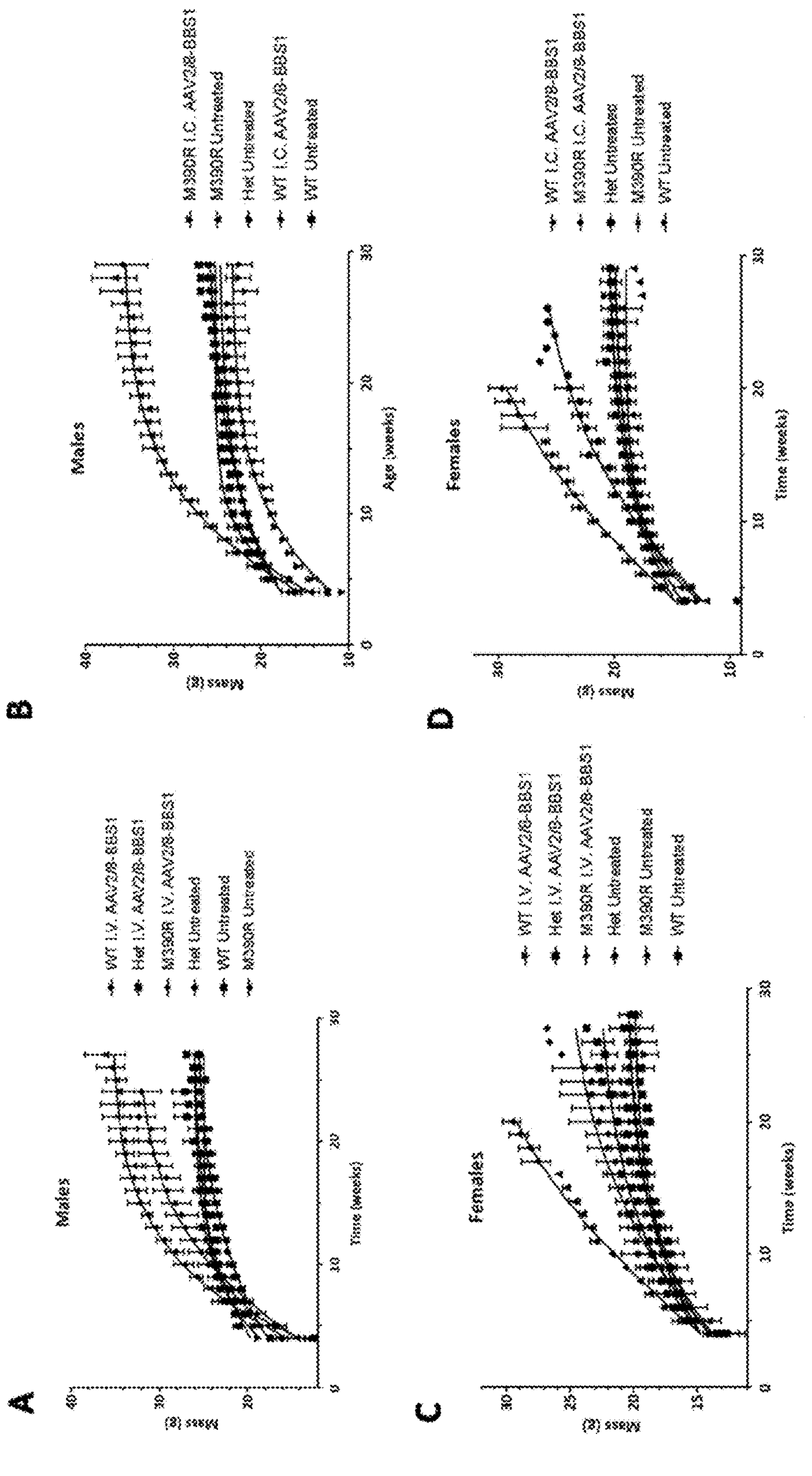
FIG. 7. Graphical representation of the Gompertz growth nonlinear regression analysis. Gompertz growth fitted the best of all tested nonlinear regression curves function. A. Intracranially P0 treated males. B. Systemically P0 treated males. C. Intracranially P0 treated females. D. Systemically P0 treated females. I.C.=Intracranial. I.V.=Intravenous.
Figure 8:
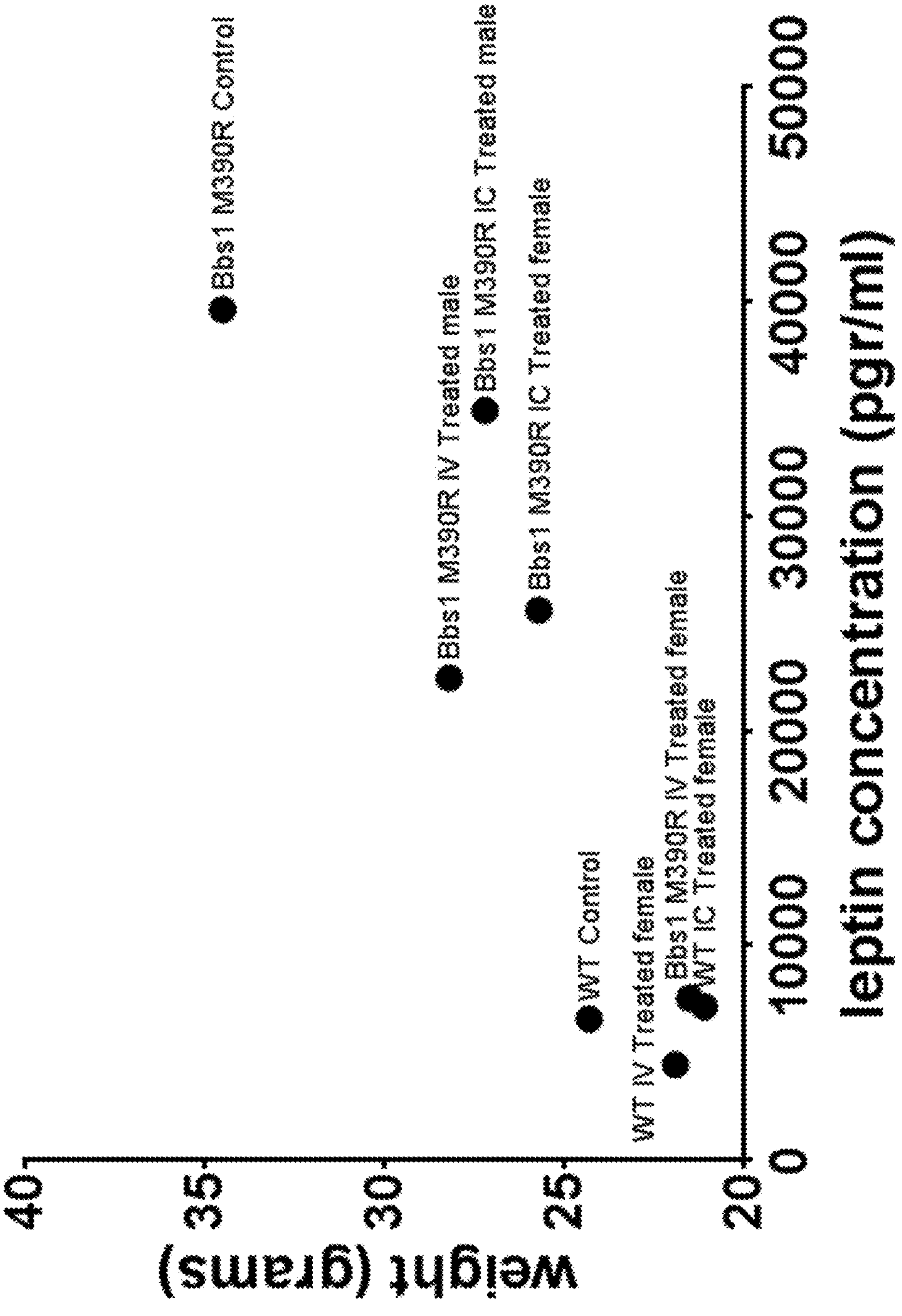
FIG. 8. Serum leptin plasma concentration/weight. AAV2/8-EFS-BBS1 IV and IC Bbs1$^{M390R/M390R}$ treated animals have reduced serum leptin concentrations 6 months after treatment. M390R=Homozygous animal Bbs1$^{M390R/M390R}$. WT=Wild-type animals. IC=Intracranially treated. IV=Intravenously treated.
Figure 13:
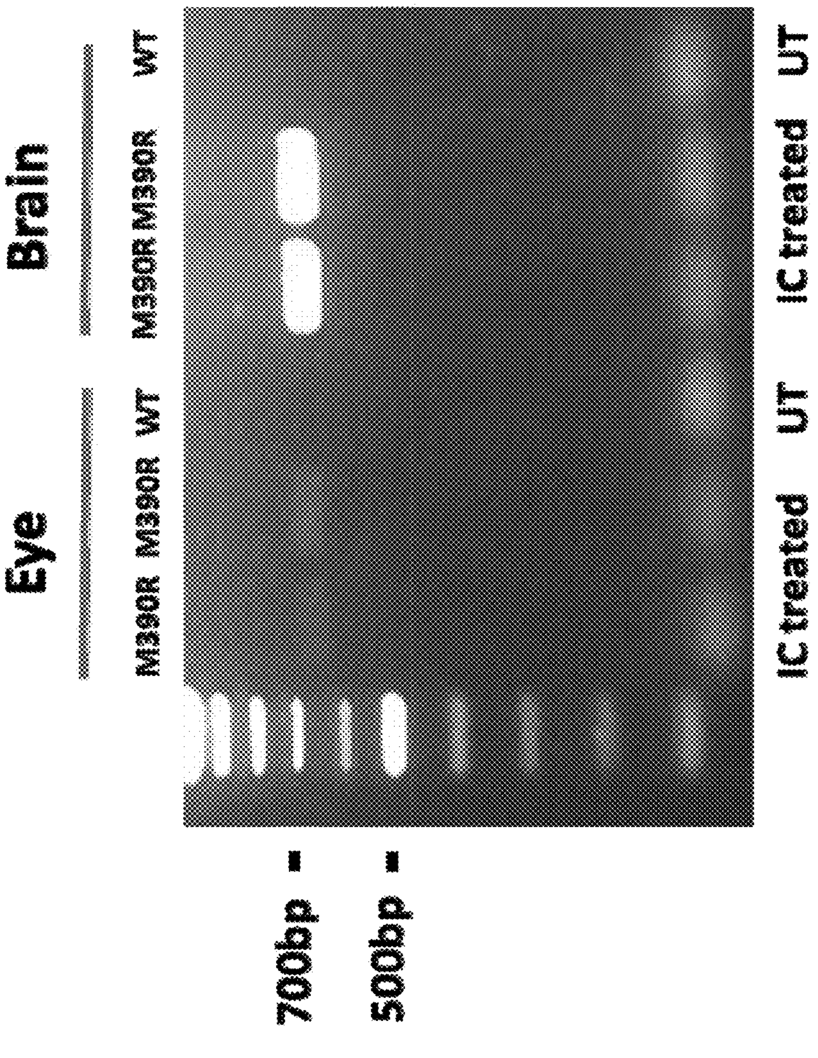
FIG. 13. Expression of human BBS1 by RT-PCR in the eye and brain at 52 weeks after P0 intracranial AAV2/8-EFS-BBS1 delivery. A clear expression of human BBS1 is observed in the eyes and brain of injected animals after intracranial injection of AAV2/8-EFS-BBS1 (IC treated), indicating good transduction and long lasting expression. Specific human primers to differentiate mouse and human BBS1 were designed, and no detection of mouse Bbs1 was observed. M390R=Bbs1$^{M390R/M390R}$; WT, wild type animals, UT, untreated; IC treated, intracranially treated.
Figure 14:
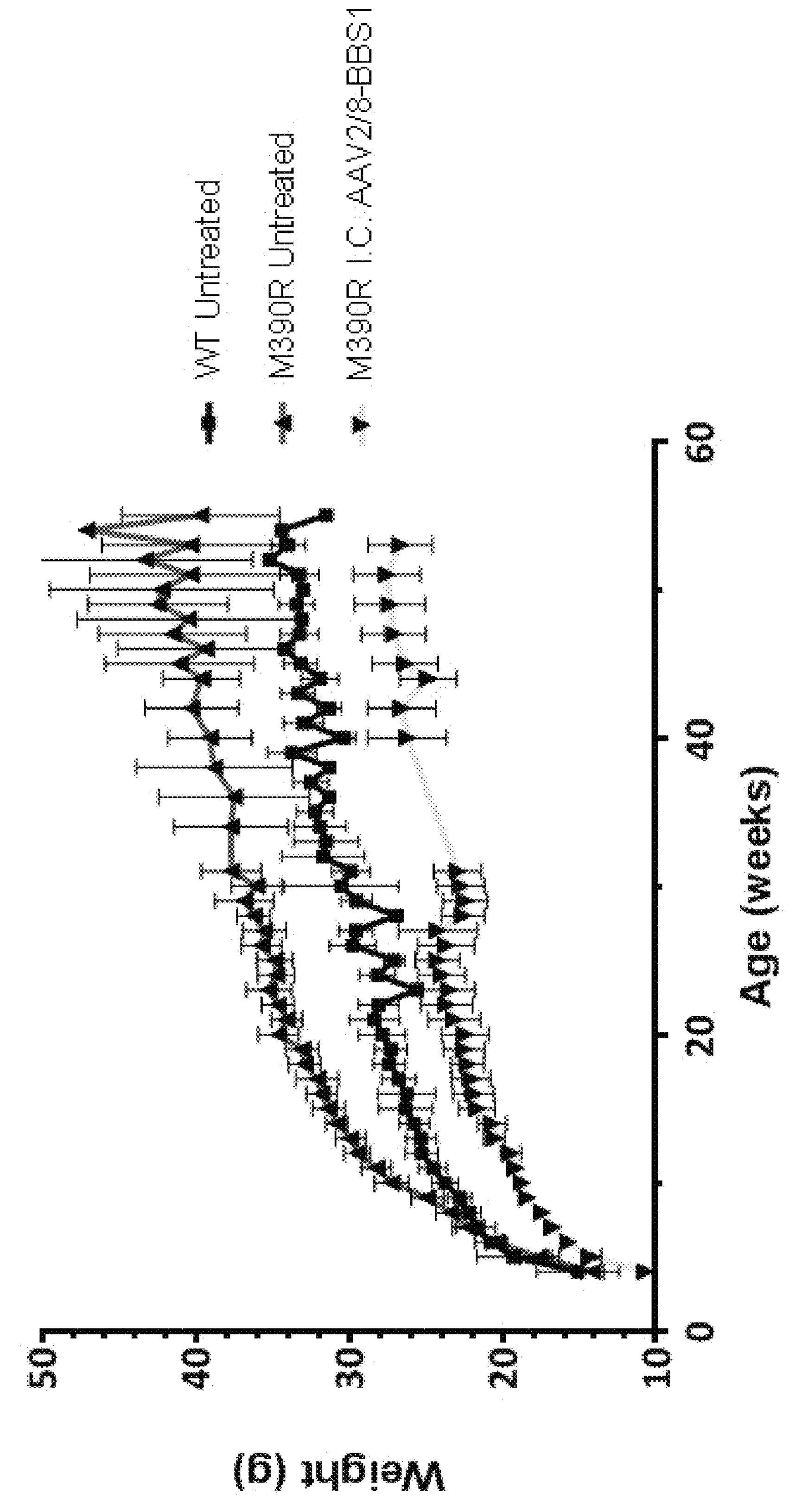
FIG. 14. Construct efficacy after a year of injection. 12 month after perinatal intracranial treatment with the construct AAV2/8 EFS-BBS1, Bbs1$^{M390R/M390R}$ treated males continue to demonstrate a reduction in weight compared with wild-type untreated littermates. WT=Wild-type animals. M390R=Homozygous animal Bbs1$^{M390R/M390R}$ Error Bars show Standard error of the Mean (S.E.M).
Figure 15:
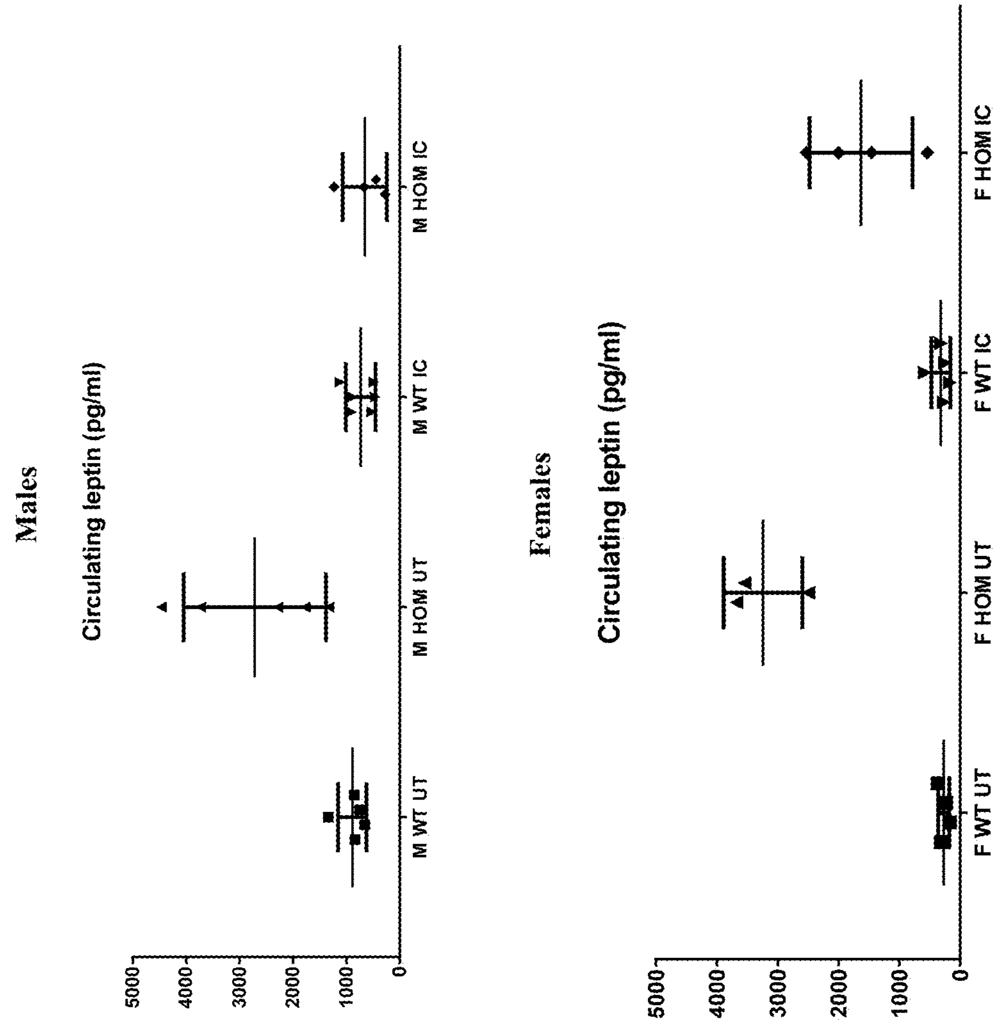
FIG. 15. Levels of circulating leptin 52 weeks post-treatment. Male and female Bbs1$^{M390R/M390R}$ animals show elevated levels of leptin. Male AAV2/8-EFS-BBS1 treated animals have the same leptin levels as untreated wild-type animals. Treated Bbs1$^{M390R/M390R}$ vs untreated wild-types are not significantly different (p-value 0.647). Untreated Bbs1$^{M390R/M390R}$ vs treated Bbs1$^{M390R/M390R}$ have a significant p-value of 0.027. Female AAV2/8-EFS-BBS1 treated animals show a significant reduction of their leptin levels compared with untreated Bbs1$^{M390R/M390R}$ animals (p-value 0.041). M, male; F, females; WT, wild type; HOM, Bbs1$^{M390R/M390R}$; UT, Untreated; IC, intracranial.

A functional study to assess the efficacy of BBS1 expression in Bbs1$^{M390R/M390R}$ mouse model was carried out. Wild-type, heterozygous Bbs1$^{M390R/+}$ and Bbs1$^{M390R/M390R}$ littermates were injected at P with AAV2/8-EFS-BBS1. In parallel, a cohort of untreated animals from all three genotypes was kept as control. The inventors followed the cohort for 26 weeks measuring the weight of each animal every week. A significant improvement was demonstrated in body weight maintenance in both, intracranially and systemically injected Bbs1$^{M390R/M390R}$ animals (FIGS. 5 to 7). No difference in body weight was observed between wild-type animals treated with AAV2/8-EFS-BBS1 and untreated animals. It has been shown that the levels of human BBS1 expression last for at least a year, as human BBS1 was found to be expressed in eye and retina 52 weeks after intracranial injection (FIG. 13). The improvement in regulation of body weight was also maintained for a whole year as shown in FIG. 14. Through a process of non-linear regression followed by one way ANOVA with Tukey's test statistical analysis, it was statistically proved that the rescue of body weight is significant in the Bbs1$^{M390R/M390R}$ animals treated with AAV2/8-EFS-BBS1 compared with untreated ones (FIG. 6). Levels of leptin in serum were analysed. There was a recovery to normal levels of leptin in Bbs1$^{M390R/M390R}$ animals treated intravenously and intracranially with AAV2/8-EFS-BBS1 (FIG. 8). The levels of normal leptin were maintained for 52 weeks for both males and females prenatally treated with AAV2/8-EFS-BBS1 (FIG. 15).

Figure 9:
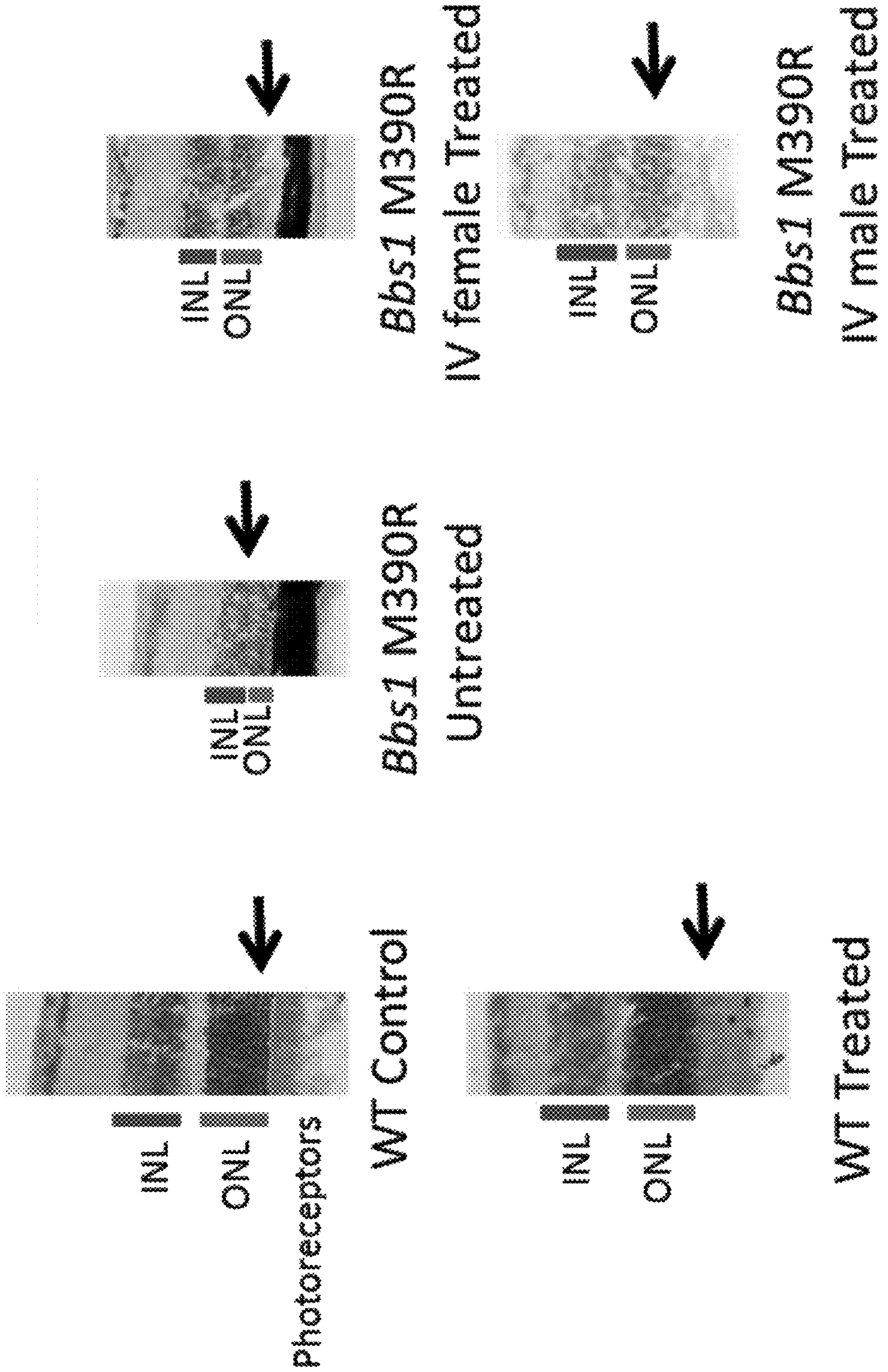
FIG. 9. Eosin-Haematoxylin retinal sections showing AAV2/8-EFS-BBS1 IV treated Bbs1$^{M390R/M390R}$ animals have attenuated loss of photoreceptors 6 months after treatment. For quantification view FIG. 11. ONL=Outer nuclear layer. IN=Inner nuclear layer. All images were taken with a ×40 objective.
Figure 10:
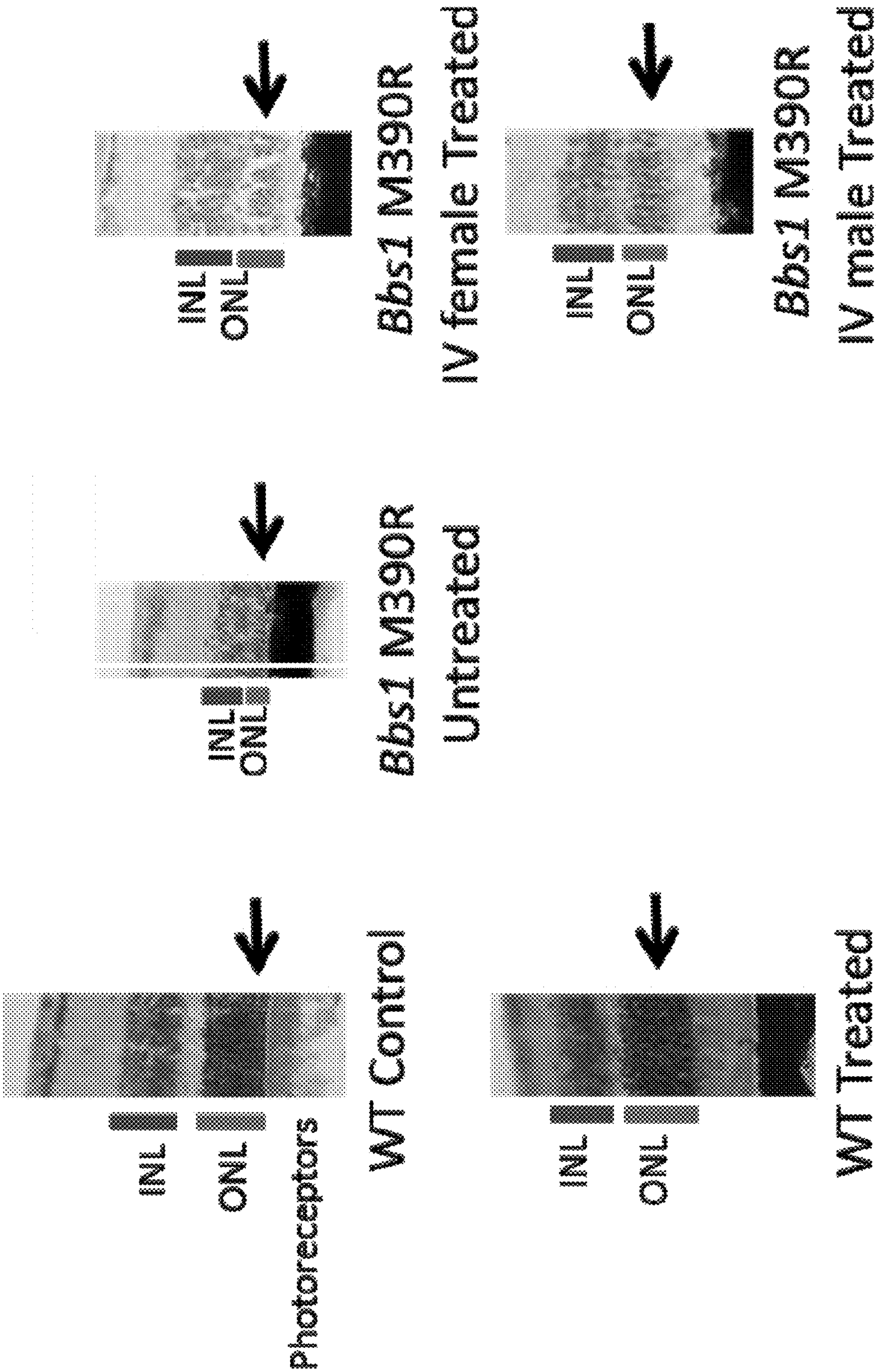
FIG. 10. Eosin-Haematoxylin retinal sections showing AAV2/8-EFS-BBS1 IC treated Bbs1$^{M390R/M390R}$ animals have attenuated loss of photoreceptors 6 months after treatment. For quantification view FIG. 11. ONL=Outer nuclear layer. IN=Inner nuclear layer. All images were taken with a ×40 objective.
Figure 11:
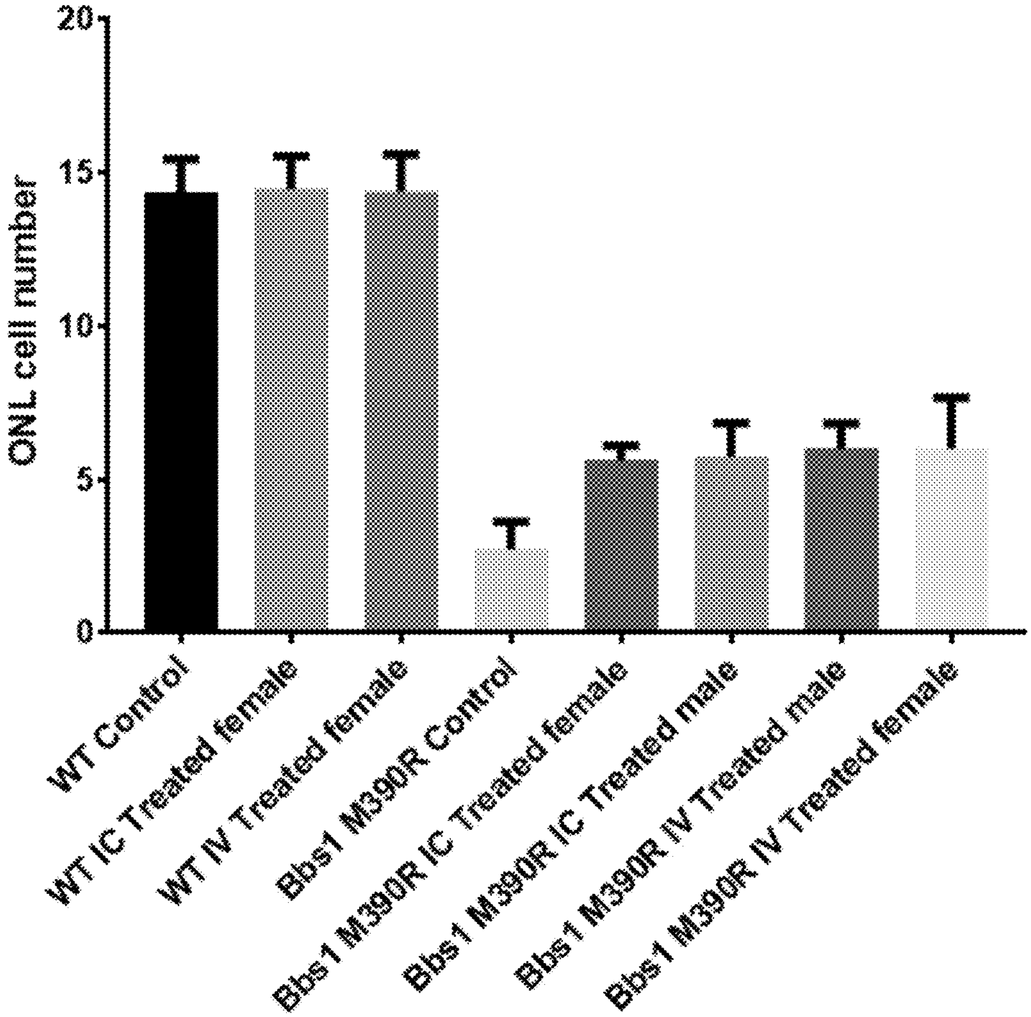
FIG. 11. Quantification of the outer nuclear layer section retinal thickness. The number of ONL nuclei recovered in Bbs1$^{M390R/M390R}$ treated animals is double compared to untreated animals.
Figure 12:
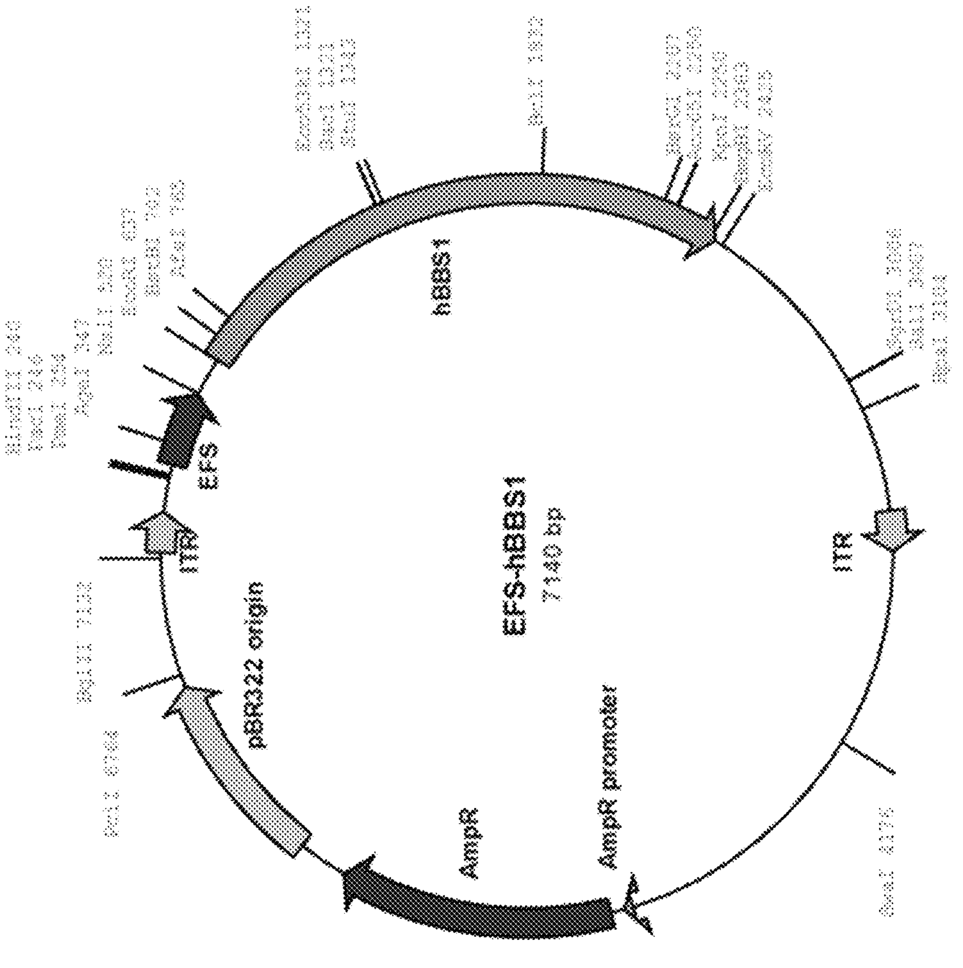
FIG. 12. A map of the vector contain EFS and human BBS1 (EFS-hBBS1) used in the following examples with the main features indicated. This vector was used to produce the AAV2/8-EFS-BBS1 virus. In certain embodiments of the invention, the promoter, ciliopathy gene and restriction sites can be different depending on the final product.

Bbs1$^{M390R/M390R}$ animals treated at P0 with AAV2/8-EFS-BBS1 also showed an attenuation of loss in the number of outer nuclear cells ONL. The attenuation was demonstrated by quantifying the number of nuclei of surviving photoreceptors, present in the retina of treated animals at 6 months compared to untreated Bbs1$^{M390R/M390R}$ animals. This effect was observed in both the intravenous and intracranially treated groups (FIGS. 9, 10 and 11).

Figure 16:
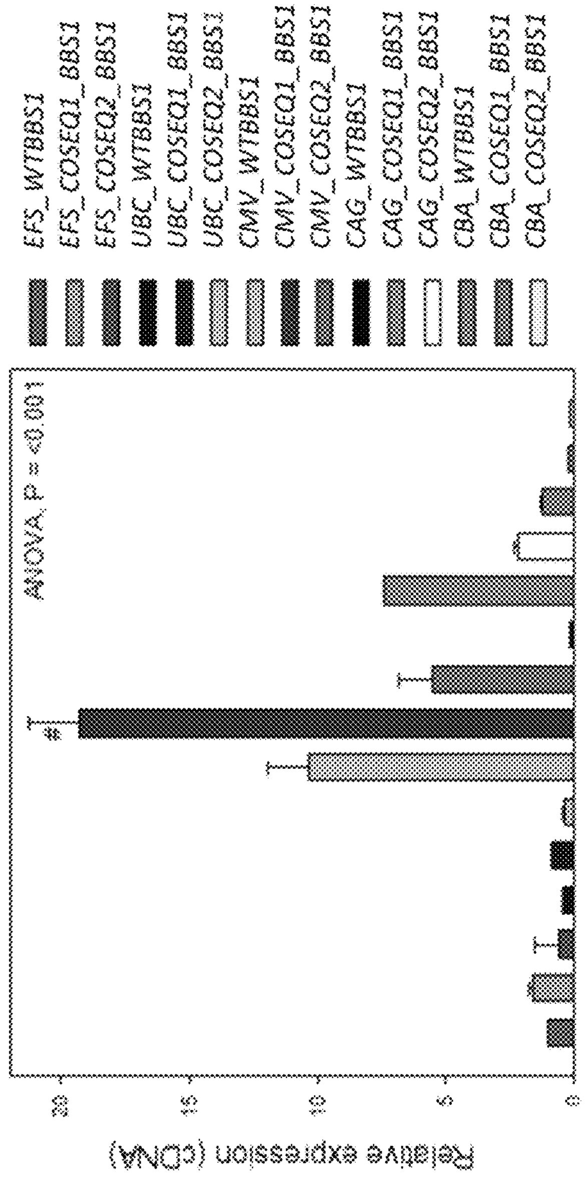
FIG. 16. Real Time PCR showing expression of BBS1 after individual transfections with all constructs from SEQ ID NO. 15 to SEQ ID NO. 29. After transfection of the constructs, total RNA was extracted and levels of RNA were quantified and normalised for the construct with SEQ ID NO. 15 (EFS-WTBBS1).
Figure 17:
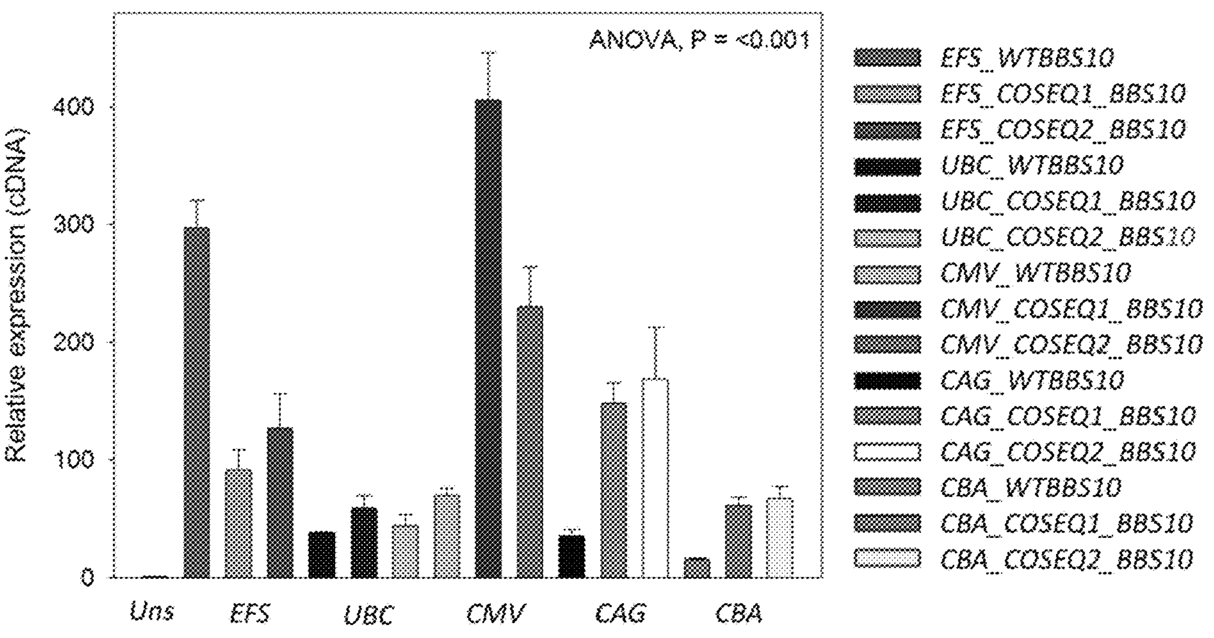
FIG. 17. Real Time PCR showing expression of BBS10 after individual transfections with all constructs from SEQ ID NO. 30 to SEQ ID NO. 44. After transfection of the constructs, total RNA was extracted and levels of RNA were quantified and normalised for the construct with untransfected HEK293T total mRNA.

With the novel codon optimised sequences, researchers showed the relative expression of BBS1 mRNA was improved after BBS1 construct transfections (see FIG. 16). CMV promoter showed the highest levels of expression, followed by the CAG promoter expression. BBS1 codon optimised sequences, COSEQ1-BBS1 and COSEQ2-BBS1, have a much better expression than the wild-type human BBS1 cDNA. The constructs with better expression are CMV-COSEQ1-BBS1 with an increase of 19-fold, CMV-WTBBS1 with an increase of 10-fold and CAG-COSEQ1-BBS1 with an increase of 7-fold. All expression is normalised relative to EFS-WTBBS1 expression. With the novel BBS10 constructs, transfections also showed an increase in human BBS10 expression and in most of the promoter-BBS10 sequence combinations the new codon optimised BBS10 sequences deliver better yields of BBS10 RNA (FIG. 17).

Figure 18:
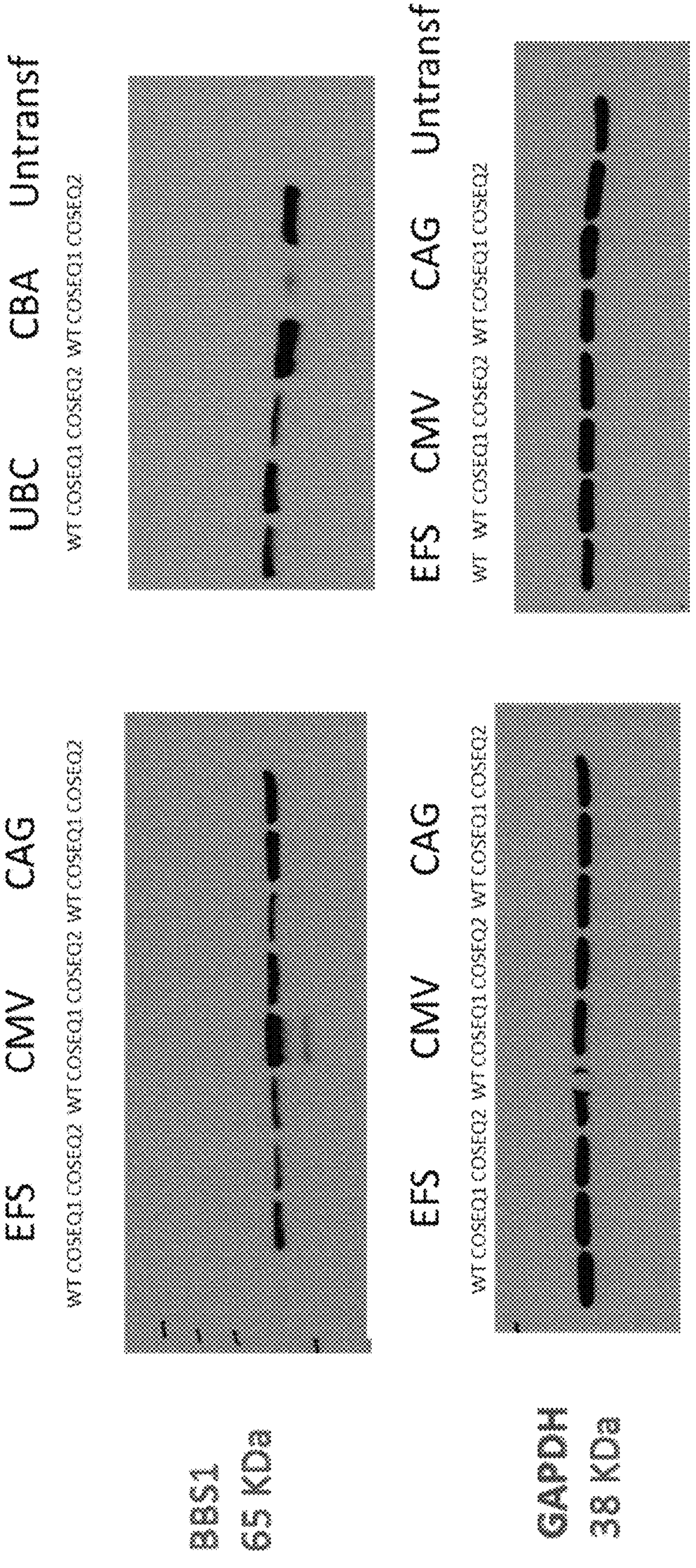
FIG. 18. Western Blots showing expression of BBS1 protein after individual transfections with constructs with SEQ ID NO. 15 to SEQ ID NO. 29. Blots were quantified using Image J and all BBS1 expression levels were normalised for SEQ ID NO. 15 (EFS-WTBBS1).
Figure 19:
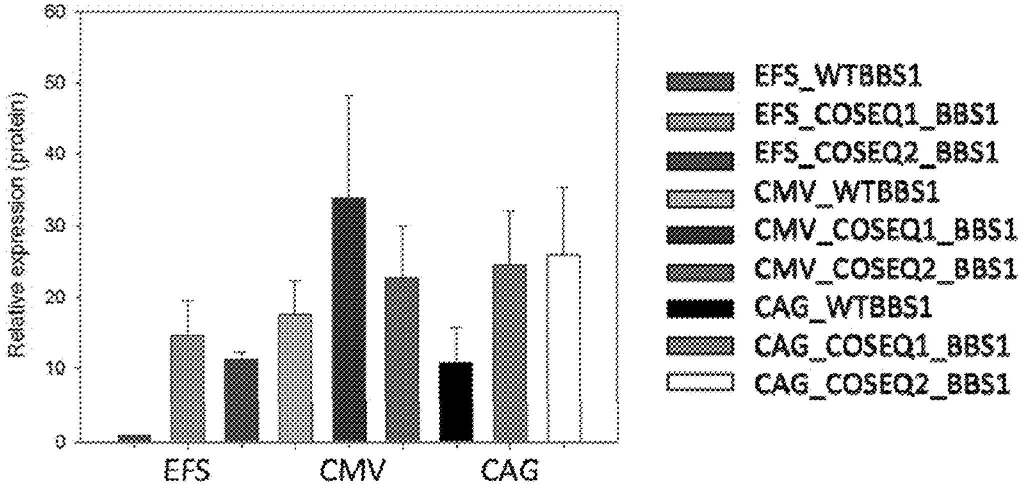
FIG. 19. Blots from FIG. 18 were quantified using Image J and all BBS1 expression levels were normalised for SEQ ID NO. 15 (EFS WT BBS1). Nearly all constructs and new BBS1 sequences showed an increased BBS1 protein expression compared with the initial EFS-WTBBS1 construct.
Figure 19:
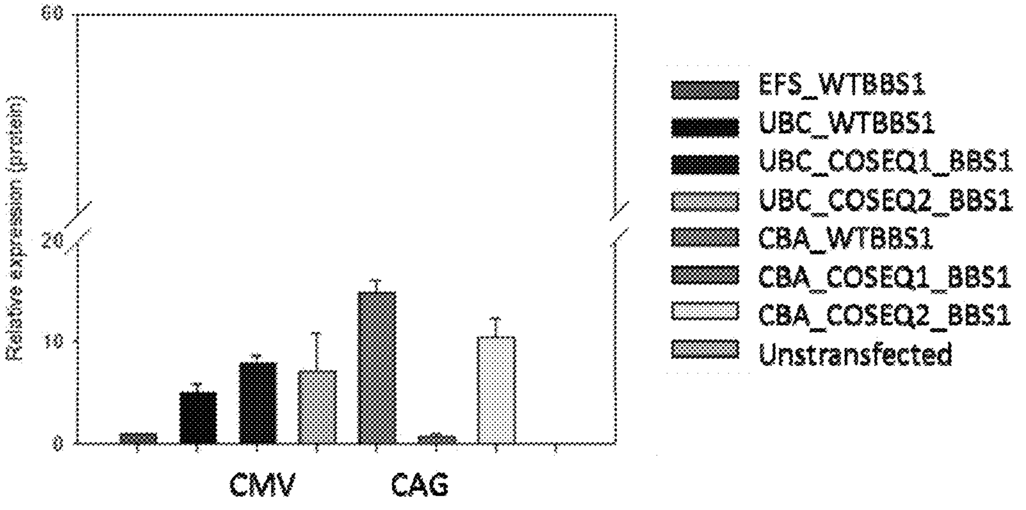

Western blots of protein extractions from all BBS1 constructs transfections showed an increase in protein expression for all BBS1 constructs. Specific bands for BBS1 (65 kDa) and for GAPDH (38 kDa) (see FIG. 18) were detected. Analysis and normalisation of the amount of protein was performed as shown in FIG. 19.

Analysis of gels show how new codon optimised sequences, COSEQ1-BBS1 and COSEQ1-BBS2, are able to express BBS1 better than wild-type BBS1, whatever the promoter that is used to drive the expression. The highest expression is found with the sequence COSEQ1-BBS1, which achieves a 33 fold increase with the CMV promoter and a 24 fold increase with the CAG promoter.

Figure 20:
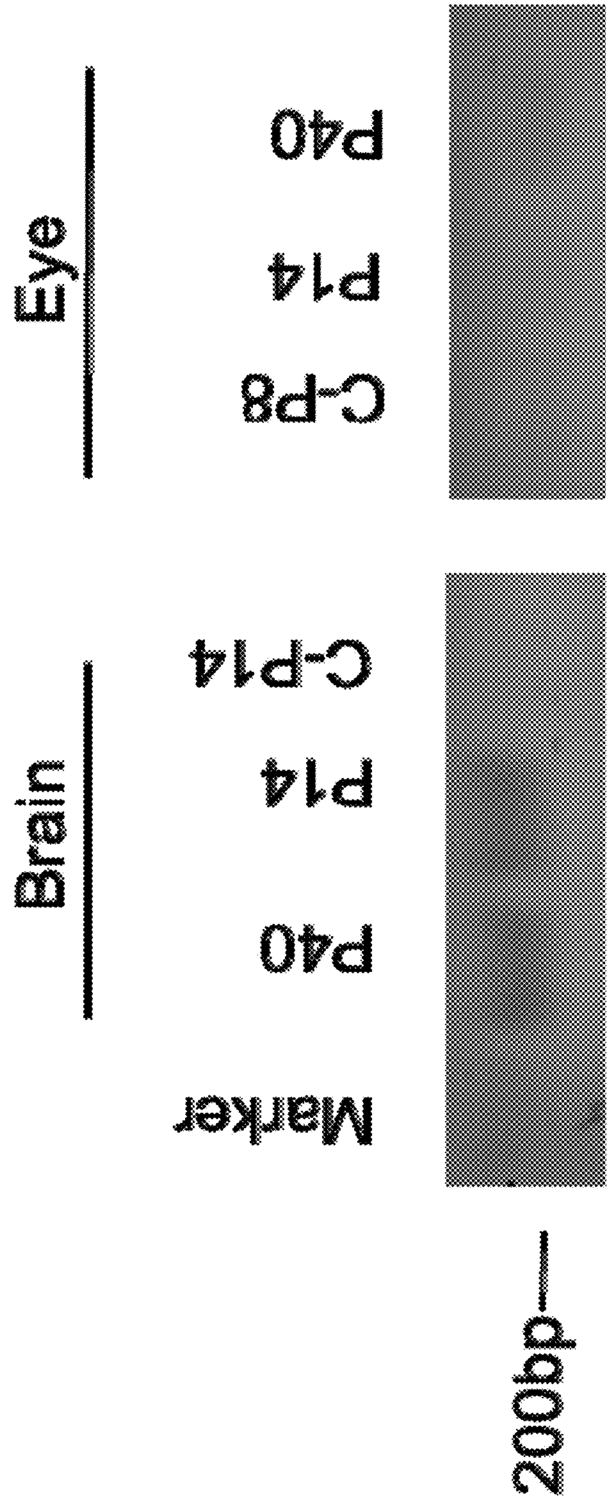
FIG. 20. RT-PCR for COSEQ1-BBS1 from samples of P0 AAV2/9-CAG-COSEQ1-BBS1 intracranially injected animals. Bbs1$^{M390R/M390R}$ animals were culled at 8, 14 and 40 days post injection with P0 AAV2/9-CAG-COSEQ1-BBS1. Total RNA was extracted and cDNA synthesised. A PCR for the COSEQ1-BBS1 with an expected band of 188 nucleotides was performed and expression of the gene expression was detected in the brain and in the eye. P, days postinjection, C-control vehicle injected, bp. Base pairs.

The inventors demonstrated the expression of the new codon optimised sequence COSEQ1-BBS1 in an AAV2/9-CAG-COSEQ1-BBS1 construct in the brain and the eye 40 days after transduction of the vector (see FIG. 20). To check the specificity of the band, the band was cut, cleaned and Sanger sequenced, observing the correct sequence for COSEQ1-BBS1.

Discussion

These results demonstrate that the inventors were able to deliver the human functional BBS1 gene that expresses the wild-type BBS1 protein, to multiple affected tissues with a single administration of a gene therapy vector. The increased expression of WT Bbs1 in the CNS was followed by the recovery of the function hypothalamic leptin regulation shown by the reduction in weight and a reduction of circulating leptin. Similarly, expression of human BBS1 in the eye was followed by an attenuation of the retinal degeneration six months after the systemic delivery (FIGS. 3-15).

The multi-tissue nature of most ciliopathies makes it challenging to treat some or all affected different organs with a single treatment. Even in the event a gene therapy is currently developed to treat a specific organ, it will only be useful for that specific phenotype and will not treat the condition more generally.

All ciliopathies have the same organs affected with different degrees of severity (see review N Engl J Med 2011; 364:1533-1543 Apr. 21, 2011). From all of them, BBS is one of the ciliopathies with more organs directly affected by mutations in BBS genes. The inventors have proven that gene therapy is able to target multiple affected tissues with a single vector dose. Therefore, the invention will be able to target specific ciliopathy genes in affected organs to restore function with a single administration.

Even in cases where the ciliopathy disorder is mainly affecting a single organ, such in the case of some ciliary retinal disorders, the intravenous, intracranial, and/or intravenous and intracranial administration will be more effective and risk-free than the actual techniques of subretinal therapies.

Treatment of Other Ciliopathies

The experiments described above show that systemic expression of a protein to replace the function of the mutated gene responsible for the ciliopathy, in this case Bardet-Biedl Syndrome, is an effective way to treat some or all the organs affected by the ciliopathy. Therefore, this is a more effective way of treating the ciliopathy than previous attempts. All ciliopathies are part of a similar spectrum of disorders that affect one way or another the cilia function or structure. The phenotypical output of that relationship is that the same gene has been found to be causative for more than one ciliopathy. Common shared genes in different ciliopathies can be found, for example MKKS/BBS6 is associated with Bardet-Biedl Syndrome and McKusick-Kaufman syndrome. The fact of sharing phenotypical expression, meaning the same organs are affected, and genetic homogeneity, the same gene involved in more than one ciliopathy, make this gene delivery and expression invention an unique approach to treat many ciliopathies. Therefore, this approach is not just limited to Bardet-Biedl Syndrome and it is applicable to many ciliopathies. Moreover, all ciliopathies are caused by mutations in a single gene therefore, the systemic expression of the appropriate non-mutated gene allows the pathologies associated with the ciliopathy to be ameliorated throughout the body.

As demonstrated above, Bardet-Biedl Syndrome can be treated using this gene therapy approach. The table below shows a number of genes in which mutations can occur to cause the phenotypical pathologies associated with Bardet-Biedl Syndrome. Therefore, using a gene therapy vector as described above which contains the appropriate gene to express the wild-type non-mutated protein can treat Bardet-Biedl Syndrome.

In addition, some of the genes which are associated with Bardet-Biedl Syndrome have also been associated with other related ciliopathies. As a result, the approach described above with the appropriate gene can also be used to treat other ciliopathies, such as Joubert syndrome, Meckel-Gruber syndrome, Nephronophthisis, Senior-Loken syndrome, McKusick-Kaufman syndrome and Leber's congenital amaurosis. For example, McKusick-Kaufman syndrome is caused by a mutation in the MKKS/BBS6 gene. Therefore, a vector which provides expression of the MKKS/BBS6 gene so that the wild type MKKS/BBS6 protein is expressed can be used to treat or ameliorate McKusick-Kaufman syndrome as well as Bardet-Biedl syndrome. This also applies to the various other ciliopathies referred to in the table below.

| Condition | Gene(s) |
|---|---|
| Bardet-Biedl syndrome | BBS1, BBS2, BBS3/ARL6, BBS4, BBS5, BBS6/MKKS, BBS7, BBS8, BBS9, BBS10, BBS11/TRIM32, BBS12, BBS13/MKS1, BBS14/CEP290, BBS15/C2ORF86, BBS16/SDCCAG8, BBS17/LZTFL1, BBS18/BBIP1, BBS19/IFT27, BBS20/IFT74, BBS21/C8ORF3. |
| Joubert syndrome | BBS14/CEP290 |
| Meckel-Gruber syndrome | BBS13/MKS1 |
| Nephronophthisis | BBS14/CEP290 |
| Senior-Loken syndrome | BBS14/CEP290 |
| McKusick-Kaufman syndrome | MKKS/BBS6 |
| Leber's congenital amaurosis | BBS14/CEP290 |

Sequences

SEQ ID NO. 1—Human Bardet-Biedl syndrome 1 (BBS1) nucleotide sequence (WT), cDNA (NM 024649.4)

SEQ ID NO. 2—Human Bardet-Biedl syndrome 10 (BBS10) nucleotide sequence (WT), cDNA (NM 024685.3)

SEQ ID NO. 3—Short elongation factor (EFS) promoter sequence

SEQ ID NO. 4—CAG promoter sequence

SEQ ID NO. 5—Ubiquitin C (UBC) promoter sequence

SEQ ID NO. 6—Cytomegalovirus (CMV) immediate-early promoter sequence

SEQ ID NO. 7—Phosphoglycerate kinase (PGK) promoter sequence

SEQ ID NO. 8—Chicken beta actin (CBA) promoter sequence

SEQ ID NO. 9—Human BBS1 full protein sequence (Q8NFJ9)

SEQ ID NO. 10—Human BBS10 full protein sequence (Q8TAM1)

SEQ ID NO. 11—Codon optimised nucleotide sequence encoding human BBS1 protein (referred to as COSEQ1-BBS1)

SEQ ID NO. 12—Codon optimised nucleotide sequence encoding human BBS1 protein (referred to as COSEQ2-BBS1)

SEQ ID NO. 13—Codon optimised nucleotide sequence encoding human BBS10 protein (referred to as COSEQ1-BBS10)

SEQ ID NO. 14—Codon optimised nucleotide sequence encoding human BBS10 protein (referred to as COSEQ2-BBS10)

SEQ ID NO 15—Construct comprising EFS promoter (nt 41-272) and wild type BBS1 nucleotide sequence (nt 1238-3019) (referred to as EFS-WTBBS1)

SEQ ID NO 16—Construct comprising EFS promoter (nt 41-272) and COSEQ1-BBS1 nucleotide sequence (nt 1243-3024) (referred to as EFS-COSEQ1-BBS1)

SEQ ID NO 17—Construct comprising EFS promoter (nt 41-272) and COSEQ2-BBS1 nucleotide sequence (nt 1243-3024) (referred to as EFS-COSEQ2-BBS1)

SEQ ID NO 18—Construct comprising UBC promoter (nt 29-1198) and wild type BBS1 nucleotide sequence (nt 1281-3062) (referred to as UBC-WTBBS1)

SEQ ID NO 19—Construct comprising UBC promoter (nt 29-1198) and COSEQ1-BBS1 nucleotide sequence (nt 1285-3066) (referred to as UBC-COSEQ11BBS1)

SEQ ID NO 20—Construct comprising UBC promoter (nt 29-1198) and COSEQ2-BBS1 nucleotide sequence (nt 1285-3066) (referred to as UBC-COSEQ2-BBS1)

SEQ ID NO 21—Construct comprising CMV promoter (nt 367-570) and wild type BBS1 nucleotide sequence (nt 626-2407) (referred to as CMV-WTBBS1)

SEQ ID NO 22—Construct comprising CMV promoter (nt 367-570) and COSEQ1-BBS1 nucleotide sequence (nt 630-2411) (referred to as CMV-COSEQ1-BBS1)

SEQ ID NO 23—Construct comprising CMV promoter (nt 367-570) and COSEQ2-BBS1 nucleotide sequence (nt 630-2411) (referred to as CMV-COSEQ2-BBS1)

SEQ ID NO 24—Construct comprising CBA promoter (nt 42-319) and wild type BBS1 nucleotide sequence (nt 469-2250) (referred to as CBA-WTBBS1)

SEQ ID NO 25—Construct comprising CBA promoter (nt 42-319) and COSEQ1-BBS1 nucleotide sequence (nt 473-2254) (referred to as CBA-COSEQ1-BBS1)

SEQ ID NO 26—Construct comprising CBA promoter (nt 42-319) and COSEQ2-BBS1 nucleotide sequence (nt 473-2254) (referred to as CBA-COSEQ2-BBS1)

SEQ ID NO 27—Construct comprising CAG promoter (nt 35-562) and wild type BBS1 nucleotide sequence (nt 712-2493) (referred to as CAG-WTBBS1)

SEQ ID NO 28—Construct comprising CAG promoter (nt 35-562) and COSEQ1-BBS1 nucleotide sequence (nt 716-2497) (referred to as CAG-COSEQ1-BBS1)

SEQ ID NO 29—Construct comprising CAG promoter (nt 35-562) and COSEQ2-BBS1 nucleotide sequence (nt 716-2497) (referred to as CAG-COSEQ2-BBS1)

SEQ ID NO 30—Construct comprising EFS promoter (nt 41-272) and wild type BBS10 nucleotide sequence (nt 1243-3414) (referred to as EFS-WTBBS10)

SEQ ID NO 31—Construct comprising EFS promoter (nt 41-272) and COSEQ1-BBS10 nucleotide sequence (nt 1243-3414) (referred to as EFS-COSEQ1-BBS10)

SEQ ID NO 32—Construct comprising EFS promoter (nt 41-272) and COSEQ2-BBS10 nucleotide sequence (nt 1243-3414) (referred to as EFS-COSEQ2-BBS10)

SEQ ID NO 33—Construct comprising UBC promoter (nt 29-1198) and wild type BBS10 nucleotide sequence (nt 1285-3456) (referred to as UBC-WTBBS10)

SEQ ID NO 34—Construct comprising UBC promoter (nt 29-1198) and COSEQ1-BBS10 nucleotide sequence (nt 1285-3456) (referred to as UBC-COSEQ1BBS10)

SEQ ID NO 35—Construct comprising UBC promoter (nt 29-1198) and COSEQ2-BBS10 nucleotide sequence (nt 1285-3456) (referred to as UBC-COSEQ2-BBS10)

SEQ ID NO 36—Construct comprising CMV promoter (nt 367-570) and wild type BBS10 nucleotide sequence (nt 630-2801) (referred to as CMV-WTBBS10)

SEQ ID NO 37—Construct comprising CMV promoter (nt 367-570) and COSEQ1-BBS10 nucleotide sequence (nt 630-2801) (referred to as CMV-COSEQ1-BBS10)

SEQ ID NO 38—Construct comprising CMV promoter (nt 367-570) and COSEQ2-BBS10 nucleotide sequence (nt 630-2801) (referred to as CMV-COSEQ2-BBS10)

SEQ ID NO 39—Construct comprising CBA promoter (nt 42-319) and wild type BBS10 nucleotide sequence (nt 473-2644) (referred to as CBA-WTBBS10)

SEQ ID NO 40—Construct comprising CBA promoter (nt 42-319) and COSEQ1-BBS10 nucleotide sequence (nt 473-2644) (referred to as CBA-COSEQ1-BBS10)

SEQ ID NO 41—Construct comprising CBA promoter (nt 42-319) and COSEQ2-BBS10 nucleotide sequence (nt 473-2644) (referred to as CBA-COSEQ2-BBS10)

SEQ ID NO 42—Construct comprising CAG promoter (nt 35-562) and wild type BBS10 nucleotide sequence (nt 716-2887) (referred to as CAG-WTBBS10)

SEQ ID NO 43—Construct comprising CAG promoter (nt 35-562) and COSEQ1-BBS10 nucleotide sequence (nt 716-2887) (referred to as CAG-COSEQ1-BBS10)

SEQ ID NO 44—Construct comprising CAG promoter (nt 35-562) and COSEQ2-BBS10 nucleotide sequence (nt 716-2887) (referred to as CAG-COSEQ2-BBS10)

SEQ ID NO. 45—Alternative CMV promoter sequence

SEQ ID NO. 46—Alternative short elongation factor (EFS) promoter sequence

SEQ ID NO. 47—Alternative CAG promoter sequence

SEQ ID NO. 48—Alternative ubiquitin C (UBC) promoter sequence

SEQ ID NO. 49—Alternative chicken beta actin (CBA) promoter sequence

What is claimed is:

1. A vector for treating a ciliopathy, wherein the vector comprises a promoter operably linked to a ciliopathy gene, wherein the vector can provide transduction of the ciliopathy gene into multiple organs, wherein the promoter is a CAG promoter which can provide expression of the ciliopathy gene in the transduced organs, and wherein the ciliopathy gene encodes a functional human protein corresponding to the protein that is mutated in the ciliopathy, wherein the ciliopathy gene comprises one of the following (a) to (b):

(a) the ciliopathy gene comprises the nucleotide sequence of SEQ ID NO. 11 or comprises at least 90% sequence identity thereto, and encodes a functional human BBS1 protein; and (b) the ciliopathy gene comprises the nucleotide sequence of SEQ ID NO. 12 or comprises at least 90% sequence identity thereto, and encodes a functional human BBS1 protein.

2. The vector according to claim 1, wherein the vector is an adeno-associated viral (AAV) vector or a lentiviral vector.

3. The vector according to claim 1, wherein the vector is an AAV vector.

4. The vector according to claim 1, wherein the vector is contained within a particle selected from an AAV8, an AAV9, or an AAV pseudotyped with the capsid proteins from an AAV8, an AAV9, an AAV-PHP.A, an AAV-PHP.B, an AAV9.47, an AAV-B1, an AAV8 (Y733F) or an AAV2-TT.

5. The vector according to claim 1, wherein the vector is contained within a particle selected from an AAV8 particle, an AAV9 particle, or an AAV particle which has been pseudotyped with the capsid proteins from an AAV8 or an AAV9.

6. The vector according to claim 1, wherein the CAG promoter comprises a sequence of SEQ ID NO. 4.

7. The vector according to claim 1, wherein the CAG promoter comprises the nucleotide sequence of SEQ ID NO. 4 or SEQ ID NO. 47.

8. The vector according to claim 1, wherein the ciliopathy gene comprises the nucleotide sequence of one of SEQ ID NOs. 11 or 12.

9. A pharmaceutical composition comprising the vector according to claim 1 and one or more pharmaceutically acceptable excipients.

* * * * *

SEQUENCE LISTING

```
<160> NUMBER OF SEQ ID NOS: 49

<210> SEQ ID NO 1
<211> LENGTH: 1782
<212> TYPE: DNA
<213> ORGANISM: Homo sapiens

<400> SEQUENCE: 1

atggccgctg cgtcctcatc ggattccgac gcctgcggag ctgagagcaa tgaggccaat      60

tcgaagtggt tggatgcgca ctacgaccca atggccaata tccacacctt ttctgcctgc     120

ctagcgctgg cagatttaca tggggatggg gaatacaagc tggtggtagg ggaccttggc     180

cctggtgggc agcagccccg cctgaaggtg ctcaaaggac cactggtgat gaccgaaagc     240

ccgctacctg ctctgccagc tgctgctgcc accttcctca tggagcaaca tgagccccgg     300

accccagctc tggcacttgc ttcaggccct tgtgtctatg tgtataagaa tctcagaccc     360

tacttcaagt tcagcctgcc ccaattgcct ccaaatcctc tggaacaaga cctttggaac     420

caggccaaag aggaccgaat cgacccctta accctgaagg agatgctgga gagcatccgg     480

gagacggcag aggagccttt gtccatccag tcactcaggt ttctgcagct ggagctaagt     540

gaaatggagg catttgtaaa ccaacacaag tccaactcca tcaagcggca gacagtcatc     600

accaccatga ccaccttgaa gaagaacctg gctgacgagg atgctgtgtc ttgcctggtg     660

ctgggcaccg agaacaagga gctcctggtg cttgaccccg aggccttcac cattttagcc     720

aagatgagcc ttcccagcgt ccccgtcttc ctagaggttt ctggccagtt tgatgttgag     780

ttccggcttg ccgcggcctg ccgcaatgga aacatctata ttctgagaag agactccaag     840

caccccaagt actgcatcga gctgagcgcc cagcctgtgg gacttatccg ggtacacaag     900

gtcctagtgg tgggcagcac ccaagacagc ctgcatggct tcacccacaa ggggaagaag     960

ctgtggacag tgcagatgcc cgcagccatc ctgaccatga acctcctgga gcagcattcc    1020

cggggcctgc aggccgtcat ggctgggctg gccaatggag aggtccgcat ttatcgtgac    1080

aaggccctgc tcaatgtcat ccacaccccg gatgcagtga ccagcctttg ctttggccgg    1140

tacgggcggg aggacaacac cctcatcatg accactcgag gtggtggcct gatcatcaag    1200

atcctgaagc gtacagcagt gtttgtagag ggaggaagtg aggtgggtcc cccaccagcc    1260
```

-continued caggccatga aactcaatgt gccccgaaag acccggcttt acgtggatca gacactgcga 1320
gagcgggagg ctggcaccgc catgcaccgg gccttccaga cagacctata cctgctgcgc 1380
ctacgtgctg cccgcgccta cctgcaggcc ctcgagtcca gcctgagccc cctgtccacg 1440
acagcccgag agccactcaa gctgcacgcc gtggttcagg gccttggccc cacctttaag 1500
ctcacacttc acctgcagaa cacctcaaca acccgtcctg tcctggggct gctggtctgc 1560
ttcctgtaca acgaggcgct ctattccctg ccccgggcct tcttcaaggt acccttgctg 1620
gtgccagggc tcaactaccc cctggagacc tttgtggaga gtctcagtaa caagggcatc 1680
tcagacatca tcaaggtgct ggtgcttcga gaaggccaaa gtgcacccct gctgagtgcc 1740
cacgtcaaca tgcctgggag cgaggggctg gcggccgcct ga 1782

<210> SEQ ID NO 2
<211> LENGTH: 2172
<212> TYPE: DNA
<213> ORGANISM: Homo sapiens

<400> SEQUENCE: 2
atgttaagtt ctatggccgc tgcagggtct gtgaaggcgg cgttgcaggt ggccgaggtg 60
ctggaagcca tcgtgagctg ctgcgtgggg cccgagggac ggcaagtttt gtgtacgaag 120
cccactggcg aggtgcttct cagccggaat ggaggccgcc tcctggaggc gctacactta 180
gagcatccca tagccaggat gatagtggac tgtgtttcca gtcatctcaa aaaaacagga 240
gatggtgcaa aaacatttat tatctttctt tgccatttgc ttagaggact tcatgcaatc 300
acagacagag aaaaggatcc tttgatgtgt gaaaacattc aaacccatgg aaggcattgg 360
aaaaattgtt ctcggtggaa atttatttcc caggctctcc taacgtttca gacacaaata 420
ttagacggta ttatggacca gtacctaagt agacactttt tgtctatctt ttcgtctgct 480
aaagagagaa cattgtgtag gagctcttta gagttgctct tagaagcata cttttgtgga 540
agagtgggaa gaaataatca taaatttatt tcacagttga tgtgtgacta ctttttcaag 600
tgtatgactt gtaaaagtgg gattggtgta tttgagttag tggatgacca ttttgtagag 660
ttgaatgttg gtgtcactgg ccttcctgtt tcagattcca ggatcatagc tggtcttgtg 720
cttcagaaag atttttctgt gtaccgccca gcagatggtg acatgcgaat ggtgatagta 780
acagaaacca ttcagcctct tttttccact tctggatcag agtttattct aaattcagaa 840
gcacagtttc agacatctca attttggatt atggaaaaga caaaagcaat aatgaaacat 900
ctacatagtc agaatgtaaa attgctcata tctagtgtga aacaaccaga tttagttagt 960
tattatgcag ggtgaatgg catatcagtg gttgagtgtt tatcatcaga agaagtttct 1020
cttatccgga ggatcattgg tctttctcca tttgtaccac cacaggcctt ttcgcagtgt 1080
gaaataccta acactgcttt ggtgaaattt tgtaaacctc ttatccttag atccaaaaga 1140
tatgttcatc taggcttgat aagcacatgt gcatttatac cacactctat agttctttgt 1200
ggaccagtgc atggtctcat tgaacaacat gaggatgctt tacatggagc acttaaaatg 1260
cttcggcaat tatttaaaga ccttgatcta aattacatga cacaaaccaa tgaccaaaat 1320
ggcacttcaa gtctttttat ttataagaac agtggagaaa gttatcaagc accagatcct 1380
ggtaatggct caatacaaag gccttatcag gacacagttg cagagaacaa agatgcattg 1440
gaaaaaactc aaacatattt aaaagtacat tctaatttgg taattccaga tgtagaatta 1500
gaaacatata ttccgtattc aacccccaca ctgacaccaa cagatacatt ccaaacagtt 1560
gaaacgctga catgtttgtc tttggaaaga aacaggctaa ctgattatta tgaaccatta 1620

-continued ctcaagaaca attccactgc ttattcaaca aggggaaata gaatagaaat ttcttacgaa 1680
aatttacagg tcacaaatat tactagaaag ggaagcatgt taccagtgag ctgtaagtta 1740
ccgaatatgg gtacttccca gagttacctt tcctcatcta tgccagctgg ttgtgttttg 1800
ccagtaggtg gtaattttga gatcttgtta cattactatc ttctcaatta tgccaaaaaa 1860
tgccatcaat cagaagaaac catggttagt atgataatag ctaatgcact tttaggcatt 1920
cccaaagtcc tttataaatc taaaacagga aagtacagct ttccacatac atatataaga 1980
gctgtccatg cactgcaaac caatcaaccc ttggtaagca gtcagacagg tttggaatca 2040
gtaatgggta aataccagct actaacttca gttcttcagt gtttgacaaa aatattaacc 2100
attgacatgg taatcactgt taagagacac cctcagaaag ttcacaatca agattcagaa 2160
gatgaactat aa 2172

<210> SEQ ID NO 3
<211> LENGTH: 232
<212> TYPE: DNA
<213> ORGANISM: Homo sapiens

<400> SEQUENCE: 3
ggctccggtg cccgtcagtg ggcagagcgc acatcgccca cagtccccga gaagttgggg 60
ggaggggtcg gcaattgatc cggtgcctag agaaggtggc gcggggtaaa ctgggaaagt 120
gatgtcgtgt actggctccg cctttttccc gagggtgggg gagaaccgta tataagtgca 180
gtagtcgccg tgaacgttct ttttcgcaac gggtttgccg ccagaacaca gg 232

<210> SEQ ID NO 4
<211> LENGTH: 584
<212> TYPE: DNA
<213> ORGANISM: Artificial sequence
<220> FEATURE:
<223> OTHER INFORMATION: CAG promoter sequence

<400> SEQUENCE: 4
gcgttacata acttacggta aatggcccgc ctggctgacc gcccaacgac ccccgcccat 60
tgacgtcaat aatgacgtat gttcccatag taacgccaat agggactttc cattgacgtc 120
aatgggtgga gtatttacgg taaactgccc acttggcagt acatcaagtg tatcatatgc 180
caagtacgcc ccctattgac gtcaatgacg gtaaatggcc cgcctggcat tatgcccagt 240
acatgacctt atgggacttt cctacttggc agtacatcta cgtattagtc atcgctatta 300
ccatggtcga ggtgagcccc acgttctgct tcactctccc catctccccc ccctccccac 360
ccccaatttt gtatttattt atttttaat tattttgtgc agcgatgggg gcgggggggg 420 gggggggcg cgcgccaggc ggggcggggc ggggcgaggg gcggggcggg gcgaggcgga 480
gaggtgcggc ggcagccaat cagagcggcg cgctccgaaa gtttcctttt atggcgaggc 540
ggcggcggcg gcggccctat aaaaagcgaa gcgcgcggcg ggcg 584

<210> SEQ ID NO 5
<211> LENGTH: 1177
<212> TYPE: DNA
<213> ORGANISM: Homo sapiens

<400> SEQUENCE: 5
ggtgcagcgg cctccgcgcc gggttttggc gcctcccgcg ggcgcccccc tcctcacggc 60
gagcgctgcc acgtcagacg aagggcgcag gagcgttcct gatccttccg cccggacgct 120

-continued

```
caggacagcg gcccgctgct cataagactc ggccttagaa ccccagtatc agcagaagga    180

cattttagga cgggacttgg gtgactctag ggcactggtt ttctttccag agagcggaac    240

aggcgaggaa aagtagtccc ttctcggcga ttctgcggag ggatctccgt ggggcggtga    300

acgccgatga ttatataagg acgcgccggg tgtggcacag ctagttccgt cgcagccggg    360

atttgggtcg cggttcttgt ttgtggatcg ctgtgatcgt cacttggtga gttgcgggct    420

gctgggctgg ccggggcttt cgtggccgcc gggccgctcg gtgggacgga agcgtgtgga    480

gagaccgcca agggctgtag tctgggtccg cgagcaaggt tgccctgaac tgggggttgg    540

ggggagcgca caaaatggcg gctgttcccg agtcttgaat ggaagacgct tgtaaggcgg    600

gctgtgaggt cgttgaaaca aggtgggggg catggtgggc ggcaagaacc caaggtcttg    660

aggccttcgc taatgcggga aagctcttat tcgggtgaga tgggctgggg caccatctgg    720

ggaccctgac gtgaagtttg tcactgactg gagaactcgg gtttgtcgtc tggttgcggg    780

ggcggcagtt atgcggtgcc gttgggcagt gcacccgtac ctttgggagc gcgcgcctcg    840

tcgtgtcgtg acgtcacccg ttctgttggc ttataatgca gggtggggcc acctgccggt    900

aggtgtgcgg taggcttttc tccgtcgcag gacgcagggt tcgggcctag ggtaggctct    960

cctgaatcga caggcgccgg acctctggtg aggggaggga taagtgaggc gtcagtttct   1020

ttggtcggtt ttatgtacct atcttcttaa gtagctgaag ctccggtttt gaactatgcg   1080

ctcggggttg gcgagtgtgt tttgtgaagt tttttaggca ccttttgaaa tgtaatcatt   1140

tgggtcaata tgtaattttc agtgttagac tagtaaa                            1177
```

```
<210> SEQ ID NO 6
<211> LENGTH: 511
<212> TYPE: DNA
<213> ORGANISM: Human cytomegalovirus

<400> SEQUENCE: 6

gatctgacgg ttcactaaac gagctctgct tatatagacc tcccaccgta cacgcctacc     60

gcccatttgc gtcaatgggg cggagttgtt acgacatttt ggaaagtccc gttgattttg    120

gtgccaaaac aaactcccat tgacgtcaat ggggtggaga cttggaaatc cccgtgagtc    180

aaaccgctat ccacgcccat tgatgtactg ccaaaaccgc atcaccatgg taatagcgat    240

gactaatacg tagatgtact gccaagtagg aaagtcccat aaggtcatgt actgggcata    300

atgccaggcg ggccatttac cgtcattgac gtcaataggg ggcgtacttg gcatatgata    360

cacttgatgt actgccaagt gggcagttta ccgtaaatac tccacccatt gacgtcaatg    420

gaaagtccct attggtcatt attgacgtca atgggcgggg gtcgttgggc ggtcagccag    480

gcgggccatt taccgtaagt tatgtaacgg g                                   511
```

```
<210> SEQ ID NO 7
<211> LENGTH: 511
<212> TYPE: DNA
<213> ORGANISM: Mus musculus

<400> SEQUENCE: 7

ttctaccggg taggggaggc gcttttccca aggcagtctg gagcatgcgc tttagcagcc     60

ccgctgggca cttggcgcta cacaagtggc ctctggcctc gcacacattc cacatccacc    120

ggtaggcgcc aaccggctcc gttctttggt ggccccttcg cgccaccttc tactcctccc    180

ctagtcagga agttcccccc cgccccgcag ctcgcgtcgt gcaggacgtg acaaatggaa    240

gtagcacgtc tcactagtct cgtgcagatg gacagcaccg ctgagcaatg gaagcgggta    300
```

-continued

```
ggcctttggg gcagcggcca atagcagctt tgctccttcg ctttctgggc tcagaggctg    360

ggaaggggtg ggtccggggg cgggctcagg ggcgggctca ggggcggggc gggcgcccga    420

aggtcctccg gaggcccggc attctgcacg cttcaaaagc gcacgtctgc cgcgctgttc    480

tcctcttcct catctccggg cctttcgacc t                                   511


<210> SEQ ID NO 8
<211> LENGTH: 260
<212> TYPE: DNA
<213> ORGANISM: Gallus gallus

<400> SEQUENCE: 8

cacgttctgc ttcactctcc ccatctcccc cccctcccca cccccaattt tgtatttatt     60

tattttttaa ttattttgtg cagcgatggg ggcggggggg gggggggcgc gcgccaggcg    120

gggcggggcg gggcgagggg cggggcgggg cgaggcggag aggtgcggcg gcagccaatc    180

agagcggcgc gctccgaaag tttcctttta tggcgaggcg gcggcggcgg cggccctata    240

aaaagcgaag cgcgcggcgg                                                260


<210> SEQ ID NO 9
<211> LENGTH: 593
<212> TYPE: PRT
<213> ORGANISM: Homo sapiens

<400> SEQUENCE: 9

Met Ala Ala Ala Ser Ser Ser Asp Ser Asp Ala Cys Gly Ala Glu Ser
1               5                   10                  15

Asn Glu Ala Asn Ser Lys Trp Leu Asp Ala His Tyr Asp Pro Met Ala
            20                  25                  30

Asn Ile His Thr Phe Ser Ala Cys Leu Ala Leu Ala Asp Leu His Gly
        35                  40                  45

Asp Gly Glu Tyr Lys Leu Val Val Gly Asp Leu Gly Pro Gly Gly Gln
    50                  55                  60

Gln Pro Arg Leu Lys Val Leu Lys Gly Pro Leu Val Met Thr Glu Ser
65                  70                  75                  80

Pro Leu Pro Ala Leu Pro Ala Ala Ala Ala Thr Phe Leu Met Glu Gln
                85                  90                  95

His Glu Pro Arg Thr Pro Ala Leu Ala Leu Ala Ser Gly Pro Cys Val
            100                 105                 110

Tyr Val Tyr Lys Asn Leu Arg Pro Tyr Phe Lys Phe Ser Leu Pro Gln
        115                 120                 125

Leu Pro Pro Asn Pro Leu Glu Gln Asp Leu Trp Asn Gln Ala Lys Glu
    130                 135                 140

Asp Arg Ile Asp Pro Leu Thr Leu Lys Glu Met Leu Glu Ser Ile Arg
145                 150                 155                 160

Glu Thr Ala Glu Glu Pro Leu Ser Ile Gln Ser Leu Arg Phe Leu Gln
                165                 170                 175

Leu Glu Leu Ser Glu Met Glu Ala Phe Val Asn Gln His Lys Ser Asn
            180                 185                 190

Ser Ile Lys Arg Gln Thr Val Ile Thr Thr Met Thr Thr Leu Lys Lys
        195                 200                 205

Asn Leu Ala Asp Glu Asp Ala Val Ser Cys Leu Val Leu Gly Thr Glu
    210                 215                 220

Asn Lys Glu Leu Leu Val Leu Asp Pro Glu Ala Phe Thr Ile Leu Ala
225                 230                 235                 240
```

-continued

Lys Met Ser Leu Pro Ser Val Pro Val Phe Leu Glu Val Ser Gly Gln
245 250 255

Phe Asp Val Glu Phe Arg Leu Ala Ala Ala Cys Arg Asn Gly Asn Ile
260 265 270

Tyr Ile Leu Arg Arg Asp Ser Lys His Pro Lys Tyr Cys Ile Glu Leu
275 280 285

Ser Ala Gln Pro Val Gly Leu Ile Arg Val His Lys Val Leu Val Val
290 295 300

Gly Ser Thr Gln Asp Ser Leu His Gly Phe Thr His Lys Gly Lys Lys
305 310 315 320

Leu Trp Thr Val Gln Met Pro Ala Ala Ile Leu Thr Met Asn Leu Leu
325 330 335

Glu Gln His Ser Arg Gly Leu Gln Ala Val Met Ala Gly Leu Ala Asn
340 345 350

Gly Glu Val Arg Ile Tyr Arg Asp Lys Ala Leu Leu Asn Val Ile His
355 360 365

Thr Pro Asp Ala Val Thr Ser Leu Cys Phe Gly Arg Tyr Gly Arg Glu
370 375 380

Asp Asn Thr Leu Ile Met Thr Thr Arg Gly Gly Gly Leu Ile Ile Lys
385 390 395 400

Ile Leu Lys Arg Thr Ala Val Phe Val Glu Gly Gly Ser Glu Val Gly
405 410 415

Pro Pro Pro Ala Gln Ala Met Lys Leu Asn Val Pro Arg Lys Thr Arg
420 425 430

Leu Tyr Val Asp Gln Thr Leu Arg Glu Arg Glu Ala Gly Thr Ala Met
435 440 445

His Arg Ala Phe Gln Thr Asp Leu Tyr Leu Leu Arg Leu Arg Ala Ala
450 455 460

Arg Ala Tyr Leu Gln Ala Leu Glu Ser Ser Leu Ser Pro Leu Ser Thr
465 470 475 480

Thr Ala Arg Glu Pro Leu Lys Leu His Ala Val Val Gln Gly Leu Gly
485 490 495

Pro Thr Phe Lys Leu Thr Leu His Leu Gln Asn Thr Ser Thr Thr Arg
500 505 510

Pro Val Leu Gly Leu Leu Val Cys Phe Leu Tyr Asn Glu Ala Leu Tyr
515 520 525

Ser Leu Pro Arg Ala Phe Phe Lys Val Pro Leu Leu Val Pro Gly Leu
530 535 540

Asn Tyr Pro Leu Glu Thr Phe Val Glu Ser Leu Ser Asn Lys Gly Ile
545 550 555 560

Ser Asp Ile Ile Lys Val Leu Val Leu Arg Glu Gly Gln Ser Ala Pro
565 570 575

Leu Leu Ser Ala His Val Asn Met Pro Gly Ser Glu Gly Leu Ala Ala
580 585 590

Ala

<210> SEQ ID NO 10
<211> LENGTH: 723
<212> TYPE: PRT
<213> ORGANISM: Homo sapiens

<400> SEQUENCE: 10

Met Leu Ser Ser Met Ala Ala Ala Gly Ser Val Lys Ala Ala Leu Gln
1 5 10 15

-continued

```
Val Ala Glu Val Leu Glu Ala Ile Val Ser Cys Cys Val Gly Pro Glu
            20                  25                  30

Gly Arg Gln Val Leu Cys Thr Lys Pro Thr Gly Glu Val Leu Leu Ser
        35                  40                  45

Arg Asn Gly Gly Arg Leu Leu Glu Ala Leu His Leu Glu His Pro Ile
    50                  55                  60

Ala Arg Met Ile Val Asp Cys Val Ser Ser His Leu Lys Lys Thr Gly
65                  70                  75                  80

Asp Gly Ala Lys Thr Phe Ile Ile Phe Leu Cys His Leu Leu Arg Gly
                85                  90                  95

Leu His Ala Ile Thr Asp Arg Glu Lys Asp Pro Leu Met Cys Glu Asn
            100                 105                 110

Ile Gln Thr His Gly Arg His Trp Lys Asn Cys Ser Arg Trp Lys Phe
        115                 120                 125

Ile Ser Gln Ala Leu Leu Thr Phe Gln Thr Gln Ile Leu Asp Gly Ile
    130                 135                 140

Met Asp Gln Tyr Leu Ser Arg His Phe Leu Ser Ile Phe Ser Ser Ala
145                 150                 155                 160

Lys Glu Arg Thr Leu Cys Arg Ser Ser Leu Glu Leu Leu Leu Glu Ala
                165                 170                 175

Tyr Phe Cys Gly Arg Val Gly Arg Asn Asn His Lys Phe Ile Ser Gln
            180                 185                 190

Leu Met Cys Asp Tyr Phe Phe Lys Cys Met Thr Cys Lys Ser Gly Ile
        195                 200                 205

Gly Val Phe Glu Leu Val Asp Asp His Phe Val Glu Leu Asn Val Gly
    210                 215                 220

Val Thr Gly Leu Pro Val Ser Asp Ser Arg Ile Ile Ala Gly Leu Val
225                 230                 235                 240

Leu Gln Lys Asp Phe Ser Val Tyr Arg Pro Ala Asp Gly Asp Met Arg
                245                 250                 255

Met Val Ile Val Thr Glu Thr Ile Gln Pro Leu Phe Ser Thr Ser Gly
            260                 265                 270

Ser Glu Phe Ile Leu Asn Ser Glu Ala Gln Phe Gln Thr Ser Gln Phe
        275                 280                 285

Trp Ile Met Glu Lys Thr Lys Ala Ile Met Lys His Leu His Ser Gln
    290                 295                 300

Asn Val Lys Leu Leu Ile Ser Ser Val Lys Gln Pro Asp Leu Val Ser
305                 310                 315                 320

Tyr Tyr Ala Gly Val Asn Gly Ile Ser Val Val Glu Cys Leu Ser Ser
                325                 330                 335

Glu Glu Val Ser Leu Ile Arg Arg Ile Ile Gly Leu Ser Pro Phe Val
            340                 345                 350

Pro Pro Gln Ala Phe Ser Gln Cys Glu Ile Pro Asn Thr Ala Leu Val
        355                 360                 365

Lys Phe Cys Lys Pro Leu Ile Leu Arg Ser Lys Arg Tyr Val His Leu
    370                 375                 380

Gly Leu Ile Ser Thr Cys Ala Phe Ile Pro His Ser Ile Val Leu Cys
385                 390                 395                 400

Gly Pro Val His Gly Leu Ile Glu Gln His Glu Asp Ala Leu His Gly
                405                 410                 415

Ala Leu Lys Met Leu Arg Gln Leu Phe Lys Asp Leu Asp Leu Asn Tyr
            420                 425                 430
```

-continued

```
Met Thr Gln Thr Asn Asp Gln Asn Gly Thr Ser Ser Leu Phe Ile Tyr
        435                 440                 445

Lys Asn Ser Gly Glu Ser Tyr Gln Ala Pro Asp Pro Gly Asn Gly Ser
    450                 455                 460

Ile Gln Arg Pro Tyr Gln Asp Thr Val Ala Glu Asn Lys Asp Ala Leu
465                 470                 475                 480

Glu Lys Thr Gln Thr Tyr Leu Lys Val His Ser Asn Leu Val Ile Pro
                485                 490                 495

Asp Val Glu Leu Glu Thr Tyr Ile Pro Tyr Ser Thr Pro Thr Leu Thr
            500                 505                 510

Pro Thr Asp Thr Phe Gln Thr Val Glu Thr Leu Thr Cys Leu Ser Leu
        515                 520                 525

Glu Arg Asn Arg Leu Thr Asp Tyr Tyr Glu Pro Leu Leu Lys Asn Asn
    530                 535                 540

Ser Thr Ala Tyr Ser Thr Arg Gly Asn Arg Ile Glu Ile Ser Tyr Glu
545                 550                 555                 560

Asn Leu Gln Val Thr Asn Ile Thr Arg Lys Gly Ser Met Leu Pro Val
                565                 570                 575

Ser Cys Lys Leu Pro Asn Met Gly Thr Ser Gln Ser Tyr Leu Ser Ser
            580                 585                 590

Ser Met Pro Ala Gly Cys Val Leu Pro Val Gly Gly Asn Phe Glu Ile
        595                 600                 605

Leu Leu His Tyr Tyr Leu Leu Asn Tyr Ala Lys Lys Cys His Gln Ser
    610                 615                 620

Glu Glu Thr Met Val Ser Met Ile Ile Ala Asn Ala Leu Leu Gly Ile
625                 630                 635                 640

Pro Lys Val Leu Tyr Lys Ser Lys Thr Gly Lys Tyr Ser Phe Pro His
                645                 650                 655

Thr Tyr Ile Arg Ala Val His Ala Leu Gln Thr Asn Gln Pro Leu Val
            660                 665                 670

Ser Ser Gln Thr Gly Leu Glu Ser Val Met Gly Lys Tyr Gln Leu Leu
        675                 680                 685

Thr Ser Val Leu Gln Cys Leu Thr Lys Ile Leu Thr Ile Asp Met Val
    690                 695                 700

Ile Thr Val Lys Arg His Pro Gln Lys Val His Asn Gln Asp Ser Glu
705                 710                 715                 720

Asp Glu Leu
```

<210> SEQ ID NO 11
<211> LENGTH: 1782
<212> TYPE: DNA
<213> ORGANISM: Artificial sequence
<220> FEATURE:
<223> OTHER INFORMATION: Codon optimised nucleotide sequence encoding human BBS1 protein (referred to as COSEQ1-BBS1)

<400> SEQUENCE: 11

```
atggctgccg ccagcagttc tgattctgat gcctgtggcg ccgagagcaa cgaggccaat      60

tctaaatggc tggacgccca ctacgacccc atggccaata tccacacctt tagcgcctgt     120

ctggccctgg ctgatcttca tggcgacggc gagtataagc tggttgtggg agatcttgga     180

cctggcggac agcagcctag actgaaggtg ctgaagggcc ctctcgtgat gacagagtct     240

cctcttcctg ctctgcctgc cgccgctgcc acatttctga tggaacagca cgagcccaga     300

acacccgctc tggctcttgc ttctggccct tgcgtgtacg tgtacaagaa cctgcggcct     360
```

```
tacttcaagt tcagcctgcc tcagctgcct cctaatcctc tggaacagga cctgtggaac    420

caggccaaag aggacagaat cgaccctctg acactgaaag agatgctgga atccatcaga    480

gagacagccg aggaacccct gtctatccag agcctgagat tcctgcagct ggaactgagc    540

gagatggaag ccttcgtgaa ccagcacaag agcaacagca tcaagcggca gaccgtgatc    600

accaccatga ccacactgaa gaagaacctg gccgacgagg atgccgtgtc ttgtctggtg    660

ctgggcaccg agaacaaaga gctgctggtt ctggatcccg aggccttcac aatcctggcc    720

aagatgtctc tgcctagcgt gcccgtgttt ctggaagtgt ccggccagtt cgacgtggaa    780

tttcggctgg ccgctgcctg cagaaacggc aacatctaca tcctgcggag ggacagcaag    840

caccccaagt actgtatcga gctgtctgcc cagcctgtgg gcctgattag agtgcacaag    900

gtgctggtcg tgggcagcac acaggatagc ctgcacggct ttacccacaa gggcaagaaa    960

ctgtggaccg tgcagatgcc agccgccatc ctgaccatga atctgctcga acagcacagc   1020

agaggactgc aggctgttat ggcaggactg gctaatggcg aagtgcggat ctacagagac   1080

aaggccctgc tgaacgtgat ccacacacct gatgccgtga caagcctgtg cttcggcaga   1140

tacggcagag aggacaacac cctgatcatg acaacaagag gcggcggact gatcatcaag   1200

atcctgaaga gaaccgccgt gttcgtggaa ggcggatctg aagttggacc tcctccagct   1260

caggccatga agctgaatgt gcccagaaag acccggctgt acgtggacca gacactgaga   1320

gaaagagaag ccggcacagc catgcacaga gccttccaga ctgacctgta cctgctgaga   1380

ctgagagccg ccagagccta tctgcaggcc ctggaatcta gcctgtctcc tctgagcaca   1440

accgccagag agcctctgaa actgcacgct gtggttcaag gcctgggacc taccttcaag   1500

ctgaccctgc atctgcagaa caccagcacc acaagaccag tgctgggcct gctcgtgtgc   1560

ttcctgtaca atgaggccct gtacagcctg ccacgggcct tttttaaggt gccactgctg   1620

gtgcccggcc tgaactaccc tctggaaacc tttgtggaaa gcctgagcaa caagggcatc   1680

agcgacatca tcaaagtgct ggtgctgaga gagggccagt ctgctcctct gctcagcgcc   1740

catgtgaata tgcctggctc tgaaggcctg gcagccgctt aa                      1782
```

<210> SEQ ID NO 12
<211> LENGTH: 1782
<212> TYPE: DNA
<213> ORGANISM: Artificial sequence
<220> FEATURE:
<223> OTHER INFORMATION: Codon optimised nucleotide sequence encoding human BBS1 protein (referred to as COSEQ2-BBS1)

<400> SEQUENCE: 12

```
atggctgccg cctctagctc tgactctgat gcatgtggag cagagtctaa cgaggccaat     60

agcaagtggc tggacgccca ctacgatcct atggccaaca tccacacatt ctctgcctgc    120

ctggccctgg cagacctgca cggcgatgga gagtataagc tggtggtggg cgacctggga    180

cctggcggcc agcagccacg gctgaaggtg ctgaagggcc ctctggtcat gacagagtcc    240

ccactgcccg ccctgccagc cgccgccgcc accttcctga tggagcagca cgagcctaga    300

accccagccc tggccctggc ctctggcccc tgcgtgtacg tgtataagaa cctgcggccc    360

tacttcaagt ttagcctgcc acagctgccc cctaaccctc tggagcagga tctgtggaat    420

caggccaagg aggacaggat cgatcctctg acactgaagg agatgctgga gagcatccgg    480

gagacagccg aggagccact gagcatccag tccctgagat tcctgcagct ggagctgtcc    540

gagatggagg cctttgtgaa ccagcacaag tctaatagca tcaagcgcca gaccgtgatc    600
```

-continued

```
accacaatga ccacactgaa gaagaacctg gccgacgagg atgccgtgtc ttgtctggtg    660

ctgggcacag agaataagga gctgctggtg ctggacccag aggccttcac catcctggcc    720

aagatgtctc tgccctctgt gcccgtgttc ctggaggtga gcggacagtt cgacgtggag    780

tttcggctgg ctgccgcctg cagaaacggc aatatctaca tcctgcggag agatagcaag    840

cacccaaagt attgtattga gctgtccgcc cagcctgtgg gcctgatcag agtgcacaag    900

gtgctggtgg tgggcagcac ccaggactcc ctgcacggct tcacacacaa gggcaagaag    960

ctgtggaccg tgcagatgcc cgccgccatc ctgaccatga acctgctgga gcagcacagc   1020

agaggcctgc aggccgtgat ggcaggcctg gcaaatggag aggtgaggat ctaccgcgac   1080

aaggccctgc tgaatgtgat ccacacccct gatgccgtga catccctgtg cttcggccgg   1140

tatggcagag aggataacac actgatcatg accacacggg gcggcggcct gatcatcaag   1200

atcctgaaga gaacagccgt gtttgtggag ggcggctctg aagtgggccc acccccctgcc   1260

caggccatga agctgaatgt gcccaggaag acccgcctgt acgtggacca gacactgagg   1320

gaaagagagg caggaacagc aatgcacagg gccttccaga ccgatctgta cctgctgaga   1380

ctgagagcag caagagccta tctgcaggcc ctggagagct ccctgtcccc actgtctacc   1440

acagcaagag aacccctgaa gctgcacgca gtggtgcagg gcctgggacc caccttcaag   1500

ctgacactgc acctgcagaa cacatccacc acaaggcctg tgctgggcct gctggtgtgc   1560

ttcctgtaca atgaggccct gtattctctg ccacgcgcct tctttaaggt gccactgctg   1620

gtgcccggcc tgaactatcc cctggagaca ttcgtggagt ccctgtctaa taagggcatc   1680

tctgatatca tcaaggtgct ggtgctgaga gaaggacagt ccgcccctct gctgtctgcc   1740

cacgtgaata tgccaggcag cgagggcctg gctgccgcct ga                        1782
```

<210> SEQ ID NO 13
<211> LENGTH: 2172
<212> TYPE: DNA
<213> ORGANISM: Artificial sequence
<220> FEATURE:
<223> OTHER INFORMATION: Codon optimised nucleotide sequence encoding
human BBS10 protein (referred to as COSEQ1-BBS10)

<400> SEQUENCE: 13

```
atgctgtcta gcatggctgc cgctggatct gtgaaagctg ctctgcaggt tgccgaggtg     60

ctggaagcca tcgtgtcttg ttgtgtggga cctgagggca gacaggtgct gtgtacaaag    120

cctacaggcg aagtgctgct gagcagaaat ggcggcagac tgctcgaagc cctgcacctg    180

gaacacccta tcgccagaat gatcgtggac tgcgtgtcca gccacctgaa gaaaacaggc    240

gacggcgcca agaccttcat catctttctg tgccatctgc tgcggggcct gcacgccatc    300

accgatagag aaaaggaccc tctgatgtgc gagaacatcc agacacacgg ccggcactgg    360

aagaactgct cccggtggaa gtttatcagc caggctctgc tgacctttca gacccagatc    420

ctggacggca tcatggacca gtacctgagc agacacttcc tgagcatctt cagcagcgcc    480

aaagaacgga ccctgtgcag aagctctctg gaactgctgc tcgaggccta cttttgcggc    540

agagtgggca gaaacaacca caagttcatc tcccagctga tgtgtgacta cttcttcaag    600

tgcatgacct gcaagagcgg catcggcgtg ttcgagctgg tggacgatca cttcgtggaa    660

ctgaatgtgg gcgtgaccgg cctgcctgtg tccgatagca gaattattgc cggcctggtg    720

ctgcagaaag acttcagcgt gtacagaccc gccgacggcg acatgagaat ggtcatcgtg    780

accgagacaa tccagcctct gttcagcaca agcggcagcg agttcatcct gaacagcgag    840
```

```
gcccagtttc agaccagcca gttctggatc atggaaaaga ccaaggccat catgaagcac     900

ctccacagcc agaacgtgaa gctgctgatc tccagcgtga agcagcccga cctggtgtct     960

tattatgccg gcgtgaacgg catcagcgtg gtggaatgtc tgagcagcga agaggtgtcc    1020

ctgatcagac ggatcatcgg actgagcccc tttgtgcctc ctcaagcctt tagccagtgc    1080

gagatcccta acacagccct ggtcaagttc tgcaagcccc tgatcctgcg gagcaagaga    1140

tatgtgcacc tgggcctgat cagcacatgc gccttcattc ctcactccat cgtgctgtgt    1200

ggacctgtgc acggactgat tgagcagcac gaagatgcac tgcacggcgc cctgaaaatg    1260

ctgagacagc tgttcaagga cctggacctg aactacatga cccagaccaa cgaccagaac    1320

ggcaccagca gcctgttcat ctacaagaac agcggcgaga gctatcaggc cccagatcca    1380

ggcaatggca gcatccagag gccttaccag gataccgtgg ccgagaacaa ggacgccctg    1440

gaaaaaaccc agacctacct gaaggtgcac agcaacctgg tcatccccga tgtggaactg    1500

gaaacctaca ttccctacag caccccctaca ctgaccccta ccgatacctt ccagaccgtg    1560

gaaaccctga cctgtctgag cctggaacgg aacagactga ccgactacta cgagcccctg    1620

ctgaaaaaca acagcaccgc ctatagcacc cggggcaaca gaatcgagat cagctacgag    1680

aacctgcaag tgaccaacat cacccggaag ggctccatgc tgccagtgtc ctgcaagctg    1740

cctaatatgg gcaccagcca gagctacctg tcctcttcta tgcctgccgg atgtgtgctg    1800

cctgtcggcg gcaattttga gatcctgctg cactactacc tgctgaacta cgccaagaag    1860

tgccaccaga gcgaagagac aatggtgtcc atgattatcg ccaacgctct gctgggcatc    1920

cccaaggtgc tgtacaagag caagaccggc aagtacagct tccctcacac ctacattaga    1980

gccgtgcacg ccctgcagac caatcagcca ctggtttcta gccagacagg cctggaaagc    2040

gtgatgggaa agtaccagct gctgaccagc gtgctgcagt gcctgaccaa gatcctgacc    2100

atcgacatgg tcatcaccgt gaagcggcac cctcagaaag tgcacaacca ggacagcgag    2160

gacgagctgt ag                                                        2172
```

<210> SEQ ID NO 14
<211> LENGTH: 2172
<212> TYPE: DNA
<213> ORGANISM: Artificial sequence
<220> FEATURE:
<223> OTHER INFORMATION: Codon optimised nucleotide sequence encoding human BBS10 protein (referred to as COSEQ2-BBS10)

<400> SEQUENCE: 14

```
atgctgagct ccatggctgc cgccggatct gtgaaagccg ccctgcaggt ggcagaggtg      60

ctggaggcaa tcgtgagctg ttgcgtggga cctgagggcc ggcaggtgct gtgcacaaag     120

ccaaccggcg aggtgctgct gtctagaaat ggcggccggc tgctggaggc cctgcacctg     180

gagcacccaa ttgcaagaat gatcgtggac tgcgtgtcta gccacctgaa gaagacaggc     240

gatggcgcca agaccttcat catcttcctg tgccacctgc tgaggggcct gcacgccatc     300

acagaccgcg agaaggatcc tctgatgtgc gagaacatcc agacccacgg caggcactgg     360

aagaattgtt cccgctggaa gttcatctct caggccctgc tgacatttca gacccagatc     420

ctggacggca tcatggatca gtatctgagc aggcacttcc tgtccatctt ttcctctgcc     480

aaggagcgga ccctgtgcag aagctccctg gagctgctgc tggaggccta cttctgtggc     540

cgggtgggca gaaacaatca caagtttatc agccagctga tgtgcgacta tttctttaag     600

tgcatgacct gtaagtccgg catcggcgtg ttcgagctgg tggacgatca ctttgtggag     660
```

-continued

```
ctgaacgtgg gagtgacagg cctgcccgtg tccgactctc gcatcatcgc cggcctggtg    720

ctgcagaagg atttctccgt gtaccggcct gccgacggcg atatgagaat ggtcatcgtg    780

accgagacaa tccagccact gttcagcacc tccggctctg agttcatcct gaacagcgag    840

gcccagttcc agacatctca gttttggatc atggagaaga ccaaggccat catgaagcac    900

ctgcacagcc agaacgtgaa gctgctgatc tctagcgtga agcagccaga cctggtgtct    960

tactatgccg gcgtgaatgg catcagcgtg gtggagtgtc tgtcctctga ggaggtgtcc   1020

ctgatccgga gaatcattgg cctgtctccc ttcgtgcccc ctcaggcctt tagccagtgc   1080

gagatcccca acacagccct ggtgaagttc tgtaagcctc tgatcctgag gtccaagcgg   1140

tacgtgcacc tgggcctgat cagcacctgc gcctttatcc cacactctat cgtgctgtgc   1200

ggacctgtgc acggcctgat tgagcagcac gaggatgcac tgcacggcgc cctgaagatg   1260

ctgaggcagc tgttcaagga cctggatctg aattacatga cccagacaaa cgaccagaat   1320

ggcacaagct ccctgtttat ctacaagaac tctggcgaga gctatcaggc cccagatccc   1380

ggcaatggca gcattcagcg cccctaccag gacacagtgg cagagaacaa ggatgccctg   1440

gagaagaccc agacatatct gaaggtgcac tccaacctgg tcatccctga cgtggagctg   1500

gagacataca tcccttattc taccccaaca ctgaccccca cagatacctt ccagacagtg   1560

gagacactga cctgcctgtc cctggagagg aaccgcctga ccgactacta tgagcccctg   1620

ctgaagaaca attccacagc ctactctacc cggggcaata gaatcgagat cagctatgag   1680

aacctgcagg tgacaaatat caccagaaag ggctctatgc tgcctgtgag ctgcaagctg   1740

ccaaacatgg gcaccagcca gtcctacctg tctagctcca tgcctgcagg atgcgtgctg   1800

cctgtgggcg gcaacttcga gatcctgctg cactactatc tgctgaatta tgccaagaag   1860

tgccaccaga gcgaggagac aatggtgtcc atgatcatcg ccaacgccct gctgggcatc   1920

ccaaaggtgc tgtacaagtc taagaccggc aagtacagct ttccccacac ctatatccgg   1980

gccgtgcacg ccctgcagac aaatcagcct ctggtgtcta gccagaccgg cctggagtcc   2040

gtgatgggca agtaccagct gctgacatct gtgctgcagt gtctgacaaa gatcctgacc   2100

atcgatatgg tcatcaccgt gaagagacac ccacagaagg tgcacaatca ggacagcgag   2160

gatgagctgt aa                                                       2172
```

<210> SEQ ID NO 15
<211> LENGTH: 3030
<212> TYPE: DNA
<213> ORGANISM: Artificial sequence
<220> FEATURE:
<223> OTHER INFORMATION: Construct comprising EFS promoter and wild type BBS1 nucleotide sequence (referred to as EFS-WTBBS1)

<400> SEQUENCE: 15

```
actagtgggc agatctcgat cgagttgggc cccagagctt ggctccggtg cccgtcagtg     60

ggcagagcgc acatcgccca cagtccccga gaagttgtgg ggaggggtcg gcaattgaac    120

cggtgcctag agaaggtggc gcggggtaaa ctgggaaagt gatgtcgtgt actggctccg    180

cctttttccc gagggtgggg gagaaccgta tataagtgca gtagtcgccg tgaacgttct    240

ttttcgcaac gggtttgccg ccagaacaca ggtaagtgcc gtgtgtggtt cccgcgggcc    300

tggcctcttt acgggttatg gcccttgcgt gccttgaatt actccacctg gctgcagtac    360

gtgattcttg atcccgagct tcgggttgga agtgggtggg agagttcgag gccttgcgct    420

taaggagccc cttcgcctcg tgcttgagtt gaggcctggc ctgggcgctg gggccgccgc    480
```

-continued

```
gtgcgaatct ggtggcacct tcgcgcctgt ctcgctgctt tcgataagtc tctagccatt    540
taaaattttt gatgacctgc tgcgacgctt tttttctggc aagatagtct tgtaaatgcg    600
ggccaagatc tgcacactgg tatttcggtt tttggggccg cgggcggcga cggggcccgt    660
gcgtcccagc gcacatgttc ggcgaggcgg ggcctgcgag cgcggccacc gagaatcgga    720
cgggggtagt ctcaagctgg ccggcctgct ctggtgcctg gcctcgcgcc gccgtgtatc    780
gccccgccct gggcggcaag gctggcccgg tcggcaccag ttgcgtgagc ggaaagatgg    840
ccgcttcccg gccctgctgc agggagctca aaatggagga cgcggcgctc gggagagcgg    900
gcgggtgagt cacccacaca aaggaaaagg gcctttccgt cctcagccgt cgcttcatgt    960
gactccacgg agtaccgggc gccgtccagg cacctcgatt agttctcgag cttttggagt   1020
acgtcgtctt taggttgggg ggaggggttt tatgcgatgg agtttcccca cactgagtgg   1080
gtggagactg aagttaggcc agcttggcac ttgatgtaat tctccttgga atttgccctt   1140
tttgagtttg gatcttggtt cattctcaag cctcagacag tggttcaaag tttttttctt   1200
ccatttcagg tgtcgtgacc atgagcttcg aattccgatg gccgctgcgt cctcatcgga   1260
ttccgacgcc tgcggagctg agagcaatga ggccaattcg aagtggttgg atgcgcacta   1320
cgacccaatg gccaatatcc acaccttttc tgcctgccta gcgctggcag atttacatgg   1380
ggatggggaa tacaagctgg tggtagggga ccttggccct ggtgggcagc agccccgcct   1440
gaaggtgctc aaaggaccac tggtgatgac cgaaagcccg ctacctgctc tgccagctgc   1500
tgctgccacc ttcctcatgg agcaacatga gccccggacc ccagctctgg cacttgcttc   1560
aggcccttgt gtctatgtgt ataagaatct cagaccctac ttcaagttca gcctgcccca   1620
attgcctcca aatcctctgg aacaagacct ttggaaccag gccaaagagg accgaatcga   1680
ccccttaacc ctgaaggaga tgctggagag catccgggag acggcagagg agcctttgtc   1740
catccagtca ctcaggtttc tgcagctgga gctaagtgaa atggaggcat ttgtaaacca   1800
acacaagtcc aactccatca agcggcagac agtcatcacc accatgacca ccttgaagaa   1860
gaacctggct gacgaggatg ctgtgtcttg cctggtgctg ggcaccgaga acaaggagct   1920
cctggtgctt gaccccgagg ccttcaccat tttagccaag atgagccttc ccagcgtccc   1980
cgtcttccta gaggtttctg gccagtttga tgttgagttc cggcttgccg cggcctgccg   2040
caatggaaac atctatattc tgagaagaga ctccaagcac cccaagtact gcatcgagct   2100
gagcgcccag cctgtgggac ttatccgggt acacaaggtc ctagtggtgg gcagcaccca   2160
agacagcctg catggcttca cccacaaggg gaagaagctg tggacagtgc agatgcccgc   2220
agccatcctg accatgaacc tcctggagca gcattcccgg ggcctgcagg ccgtcatggc   2280
tgggctggcc aatggagagg tccgcattta tcgtgacaag gccctgctca atgtcatcca   2340
caccccggat gcagtgacca gcctttgctt tggccggtac gggcgggagg acaacaccct   2400
catcatgacc actcgaggtg gtggcctgat catcaagatc ctgaagcgta cagcagtgtt   2460
tgtagaggga ggaagtgagg tgggtccccc accagcccag gccatgaaac tcaatgtgcc   2520
ccgaaagacc cggctttacg tggatcagac actgcgagag cgggaggctg gcaccgccat   2580
gcaccgggcc ttccagacag acctatacct gctgcgccta cgtgctgccc gcgcctacct   2640
gcaggccctc gagtccagcc tgagccccct gtccacgaca gcccgagagc cactcaagct   2700
gcacgccgtg gttcagggcc ttggccccac ctttaagctc acacttcacc tgcagaacac   2760
ctcaacaacc cgtcctgtcc tggggctgct ggtctgcttc ctgtacaacg aggcgctcta   2820
ttccctgccc cgggccttct tcaaggtacc cttgctggtg ccagggctca actacccccct   2880
```

```
ggagaccttt gtggagagtc tcagtaacaa gggcatctca gacatcatca aggtgctggt   2940

gcttcgagaa ggccaaagtg cacccctgct gagtgcccac gtcaacatgc ctgggagcga   3000

ggggctggcg gccgcctgag acttgtcgac                                     3030
```

<210> SEQ ID NO 16
<211> LENGTH: 3035
<212> TYPE: DNA
<213> ORGANISM: Artificial sequence
<220> FEATURE:
<223> OTHER INFORMATION: Construct comprising EFS promoter and COSEQ1-
BBS1 nucleotide sequence (referred to as EFS-COSEQ1-BBS1)

<400> SEQUENCE: 16

```
actagtgggc agatctcgat cgagttgggc cccagagctt ggctccggtg cccgtcagtg     60

ggcagagcgc acatcgccca cagtccccga gaagttgtgg ggaggggtcg gcaattgaac    120

cggtgcctag agaaggtggc gcggggtaaa ctgggaaagt gatgtcgtgt actggctccg    180

cctttttccc gagggtgggg gagaaccgta tataagtgca gtagtcgccg tgaacgttct    240

ttttcgcaac gggtttgccg ccagaacaca ggtaagtgcc gtgtgtggtt cccgcgggcc    300

tggcctcttt acgggttatg gcccttgcgt gccttgaatt acttccacct ggctgcagta    360

cgtgattctt gatcccgagc ttcgggttgg aagtgggtgg gagagttcga ggccttgcgc    420

ttaaggagcc ccttcgcctc gtgcttgagt tgaggcctgg cctgggcgct ggggccgccg    480

cgtgcgaatc tggtggcacc ttcgcgcctg tctcgctgct ttcgataagt ctctagccat    540

ttaaaatttt tgatgacctg ctgcgacgct ttttttctgg caagatagtc ttgtaaatgc    600

gggccaagat ctgcacactg gtatttcggt ttttggggcc gcgggcggcg acggggcccg    660

tgcgtcccag cgcacatgtt cggcgaggcg gggcctgcga gcgcggccac cgagaatcgg    720

acgggggtag tctcaagctg gccggcctgc tctggtgcct ggcctcgcgc cgccgtgtat    780

cgccccgccc tgggcggcaa ggctggcccg gtcggcacca gttgcgtgag cggaaagatg    840

gccgcttccc ggccctgctg cagggagctc aaaatggagg acgcggcgct cgggagagcg    900

ggcgggtgag tcacccacac aaaggaaaag ggcctttccg tcctcagccg tcgcttcatg    960

tgactccacg gagtaccggg cgccgtccag gcacctcgat tagttctcga gcttttggag   1020

tacgtcgtct ttaggttggg gggaggggtt ttatgcgatg gagtttcccc acactgagtg   1080

ggtggagact gaagttaggc cagcttggca cttgatgtaa ttctccttgg aatttgccct   1140

ttttgagttt ggatcttggt tcattctcaa gcctcagaca gtggttcaaa gtttttttct   1200

tccatttcag gtgtcgtgac catgagcttc gaattcgcca ccatggctgc cgccagcagt   1260

tctgattctg atgcctgtgg cgccgagagc aacgaggcca attctaaatg gctggacgcc   1320

cactacgacc ccatggccaa tatccacacc tttagcgcct gtctggccct ggctgatctt   1380

catggcgacg gcgagtataa gctggttgtg ggagatcttg gacctggcgg acagcagcct   1440

agactgaagg tgctgaaggg ccctctcgtg atgacagagt ctcctcttcc tgctctgcct   1500

gccgccgctg ccacatttct gatggaacag cacgagccca gaacacccgc tctggctctt   1560

gcttctggcc cttgcgtgta cgtgtacaag aacctgcggc cttacttcaa gttcagcctg   1620

cctcagctgc ctcctaatcc tctggaacag gacctgtgga accaggccaa agaggacaga   1680

atcgaccctc tgacactgaa agagatgctg gaatccatca gagagacagc cgaggaaccc   1740

ctgtctatcc agagcctgag attcctgcag ctggaactga gcgagatgga agccttcgtg   1800

aaccagcaca agagcaacag catcaagcgg cagaccgtga tcaccaccat gaccacactg   1860
```

aagaagaacc tggccgacga ggatgccgtg tcttgtctgg tgctgggcac cgagaacaaa 1920
gagctgctgg ttctggatcc cgaggccttc acaatcctgg ccaagatgtc tctgcctagc 1980
gtgcccgtgt ttctggaagt gtccggccag ttcgacgtgg aatttcggct ggccgctgcc 2040
tgcagaaacg gcaacatcta catcctgcgg agggacagca agcaccccaa gtactgtatc 2100
gagctgtctg cccagcctgt gggcctgatt agagtgcaca aggtgctggt cgtgggcagc 2160
acacaggata gcctgcacgg ctttacccac aagggcaaga aactgtggac cgtgcagatg 2220
ccagccgcca tcctgaccat gaatctgctc gaacagcaca gcagaggact gcaggctgtt 2280
atggcaggac tggctaatgg cgaagtgcgg atctacagag acaaggccct gctgaacgtg 2340
atccacacac ctgatgccgt gacaagcctg tgcttcggca gatacggcag agaggacaac 2400
accctgatca tgacaacaag aggcggcgga ctgatcatca agatcctgaa gagaaccgcc 2460
gtgttcgtgg aaggcggatc tgaagttgga cctcctccag ctcaggccat gaagctgaat 2520
gtgcccagaa agacccggct gtacgtggac cagacactga gagaaagaga agccggcaca 2580
gccatgcaca gagccttcca gactgacctg tacctgctga gactgagagc cgccagagcc 2640
tatctgcagg ccctggaatc tagcctgtct cctctgagca caaccgccag agagcctctg 2700
aaactgcacg ctgtggttca aggcctggga cctaccttca agctgaccct gcatctgcag 2760
aacaccagca ccacaagacc agtgctgggc ctgctcgtgt gcttcctgta caatgaggcc 2820
ctgtacagcc tgccacgggc ctttttttaag gtgccactgc tggtgcccgg cctgaactac 2880
cctctggaaa cctttgtgga aagcctgagc aacaagggca tcagcgacat catcaaagtg 2940
ctggtgctga gagagggcca gtctgctcct ctgctcagcg cccatgtgaa tatgcctggc 3000
tctgaaggcc tggcagccgc ttaagcgccg tcgac 3035

<210> SEQ ID NO 17
<211> LENGTH: 3038
<212> TYPE: DNA
<213> ORGANISM: Artificial sequence
<220> FEATURE:
<223> OTHER INFORMATION: Construct comprising EFS promoter and COSEQ2-
BBS1 nucleotide sequence (referred to as EFS-COSEQ2-BBS1)

<400> SEQUENCE: 17
actagtgggc agatctcgat cgagttgggc cccagagctt ggctccggtg cccgtcagtg 60
ggcagagcgc acatcgccca cagtccccga gaagttgtgg ggaggggtcg gcaattgaac 120
cggtgcctag agaaggtggc gcggggtaaa ctgggaaagt gatgtcgtgt actggctccg 180
cctttttccc gagggtgggg gagaaccgta tataagtgca gtagtcgccg tgaacgttct 240
ttttcgcaac gggtttgccg ccagaacaca ggtaagtgcc gtgtgtggtt cccgcgggcc 300
tggcctcttt acgggttatg gcccttgcgt gccttgaatt acttccacct ggctgcagta 360
cgtgattctt gatcccgagc ttcgggttgg aagtgggtgg gagagttcga ggccttgcgc 420
ttaaggagcc ccttcgcctc gtgcttgagt tgaggcctgg cctgggcgct ggggccgccg 480
cgtgcgaatc tggtggcacc ttcgcgcctg tctcgctgct ttcgataagt ctctagccat 540
ttaaaatttt tgatgacctg ctgcgacgct ttttttctgg caagatagtc ttgtaaatgc 600
gggccaagat ctgcacactg gtatttcggt ttttggggcc gcgggcggcg acggggcccg 660
tgcgtcccag cgcacatgtt cggcgaggcg gggcctgcga gcgcggccac cgagaatcgg 720
acgggggtag tctcaagctg gccggcctgc tctggtgcct ggcctcgcgc cgccgtgtat 780
cgccccgccc tgggcggcaa ggctggcccg gtcggcacca gttgcgtgag cggaaagatg 840

```
gccgcttccc ggccctgctg cagggagctc aaaatggagg acgcggcgct cgggagagcg    900
ggcgggtgag tcacccacac aaaggaaaag ggcctttccg tcctcagccg tcgcttcatg    960
tgactccacg gagtaccggg cgccgtccag gcacctcgat tagttctcga gcttttggag   1020
tacgtcgtct ttaggttggg gggaggggtt ttatgcgatg gagtttcccc acactgagtg   1080
ggtggagact gaagttaggc cagcttggca cttgatgtaa ttctccttgg aatttgccct   1140
ttttgagttt ggatcttggt tcattctcaa gcctcagaca gtggttcaaa gtttttttct   1200
tccatttcag gtgtcgtgac catgagcttc gaattcgcca ccatggctgc cgcctctagc   1260
tctgactctg atgcatgtgg agcagagtct aacgaggcca atagcaagtg gctggacgcc   1320
cactacgatc ctatggccaa catccacaca ttctctgcct gcctggccct ggcagacctg   1380
cacggcgatg gagagtataa gctggtggtg ggcgacctgg gacctggcgg ccagcagcca   1440
cggctgaagg tgctgaaggg ccctctggtc atgacagagt ccccactgcc cgccctgcca   1500
gccgccgccg ccaccttcct gatggagcag cacgagccta gaaccccagc cctggccctg   1560
gcctctggcc cctgcgtgta cgtgtataag aacctgcggc cctacttcaa gtttagcctg   1620
ccacagctgc cccctaaccc tctggagcag gatctgtgga atcaggccaa ggaggacagg   1680
atcgatcctc tgacactgaa ggagatgctg gagagcatcc gggagacagc cgaggagcca   1740
ctgagcatcc agtccctgag attcctgcag ctggagctgt ccgagatgga ggcctttgtg   1800
aaccagcaca agtctaatag catcaagcgc cagaccgtga tcaccacaat gaccacactg   1860
aagaagaacc tggccgacga ggatgccgtg tcttgtctgg tgctgggcac agagaataag   1920
gagctgctgg tgctggaccc agaggccttc accatcctgg ccaagatgtc tctgccctct   1980
gtgcccgtgt tcctggaggt gagcggacag ttcgacgtgg agtttcggct ggctgccgcc   2040
tgcagaaacg gcaatatcta catcctgcgg agagatagca agcacccaaa gtattgtatt   2100
gagctgtccg cccagcctgt gggcctgatc agagtgcaca aggtgctggt ggtgggcagc   2160
acccaggact ccctgcacgg cttcacacac aagggcaaga agctgtggac cgtgcagatg   2220
cccgccgcca tcctgaccat gaacctgctg gagcagcaca gcagaggcct gcaggccgtg   2280
atggcaggcc tggcaaatgg agaggtgagg atctaccgcg acaaggccct gctgaatgtg   2340
atccacaccc ctgatgccgt gacatccctg tgcttcggcc ggtatggcag agaggataac   2400
acactgatca tgaccacacg gggcggcggc ctgatcatca agatcctgaa gagaacagcc   2460
gtgtttgtgg agggcggctc tgaagtgggc ccacccccctg cccaggccat gaagctgaat  2520
gtgcccagga agacccgcct gtacgtggac cagacactga gggaaagaga ggcaggaaca   2580
gcaatgcaca gggccttcca gaccgatctg tacctgctga gactgagagc agcaagagcc   2640
tatctgcagg ccctggagag ctccctgtcc ccactgtcta ccacagcaag agaacccctg   2700
aagctgcacg cagtggtgca gggcctggga cccaccttca agctgacact gcacctgcag   2760
aacacatcca ccacaaggcc tgtgctgggc ctgctggtgt gcttcctgta caatgaggcc   2820
ctgtattctc tgccacgcgc cttctttaag gtgccactgc tggtgcccgg cctgaactat   2880
cccctggaga cattcgtgga gtccctgtct aataagggca tctctgatat catcaaggtg   2940
ctggtgctga gagaaggaca gtccgcccct ctgctgtctg cccacgtgaa tatgccaggc   3000
agcgagggcc tggctgccgc ctgagcggcc gcgtcgac                           3038
```

<210> SEQ ID NO 18
<211> LENGTH: 3073
<212> TYPE: DNA

<213> ORGANISM: Artificial sequence
<220> FEATURE:
<223> OTHER INFORMATION: Construct comprising UBC promoter and wild type BBS1 nucleotide sequence (referred to as UBC-WTBBS1)

<400> SEQUENCE: 18

```
actagtaacc cgtgtcggct ccagatctgg cctccgcgcc gggttttggc gcctcccgcg     60
ggcgcccccc tcctcacggc gagcgctgcc acgtcagacg aagggcgcag cgagcgtcct    120
gatccttccg cccggacgct caggacagcg gcccgctgct cataagactc ggccttagaa    180
ccccagtatc agcagaagga cattttagga cgggacttgg gtgactctag ggcactggtt    240
ttctttccag agagcggaac aggcgaggaa aagtagtccc ttctcggcga ttctgcggag    300
ggatctccgt ggggcggtga acgccgatga ttatataagg acgcgccggg tgtggcacag    360
ctagttccgt cgcagccggg atttgggtcg cggttcttgt ttgtggatcg ctgtgatcgt    420
cacttggtga gtagcgggct gctgggctgg ccggggcttt cgtggccgcc gggccgctcg    480
gtgggacgga agcgtgtgga gagaccgcca agggctgtag tctgggtccg cgagcaaggt    540
tgccctgaac tgggggttgg ggggagcgca gcaaaatggc ggctgttccc gagtcttgaa    600
tggaagacgc ttgtgaggcg ggctgtgagg tcgttgaaac aaggtggggg gcatggtggg    660
cggcaagaac ccaaggtctt gaggccttcg ctaatgcggg aaagctctta ttcgggtgag    720
atgggctggg gcaccatctg ggaccctga cgtgaagttt gtcactgact ggagaactcg    780
gtttgtcgtc tgttgcgggg gcggcagtta tggcggtgcc gttgggcagt gcacccgtac    840
ctttgggagc gcgcgccctc gtcgtgtcgt gacgtcaccc gttctgttgg cttataatgc    900
agggtggggc cacctgccgg taggtgtgcg gtaggctttt ctccgtcgca ggacgcaggg    960
ttcgggccta gggtaggctc tcctgaatcg acaggcgccg gacctctggt gaggggaggg   1020
ataagtgagg cgtcagtttc tttggtcggt tttatgtacc tatcttctta agtagctgaa   1080
gctccggttt tgaactatgc gctcggggtt ggcgagtgtg ttttgtgaag ttttttaggc   1140
accttttgaa atgtaatcat ttgggtcaat atgtaatttt cagtgttaga ctagtaaatt   1200
gtccgctaaa ttctggccgt ttttggcttt tttgttagac gaagcttggg ctgcaggtcg   1260
agctcaagct tcgaattccg atggccgctg cgtcctcatc ggattccgac gcctgcggag   1320
ctgagagcaa tgaggccaat tcgaagtggt tggatgcgca ctacgaccca atggccaata   1380
tccacacctt ttctgcctgc ctagcgctgg cagatttaca tggggatggg gaatacaagc   1440
tggtggtagg ggaccttggc cctggtgggc agcagccccg cctgaaggtg ctcaaaggac   1500
cactggtgat gaccgaaagc ccgctacctg ctctgccagc tgctgctgcc accttcctca   1560
tggagcaaca tgagccccgg accccagctc tggcacttgc ttcaggccct tgtgtctatg   1620
tgtataagaa tctcagaccc tacttcaagt tcagcctgcc ccaattgcct ccaaatcctc   1680
tggaacaaga cctttggaac caggccaaag aggaccgaat cgacccctta accctgaagg   1740
agatgctgga gagcatccgg gagacggcag aggagccttt gtccatccag tcactcaggt   1800
ttctgcagct ggagctaagt gaaatggagg catttgtaaa ccaacacaag tccaactcca   1860
tcaagcggca gacagtcatc accaccatga ccaccttgaa gaagaacctg gctgacgagg   1920
atgctgtgtc ttgcctggtg ctgggcaccg agaacaagga gctcctggtg cttgaccccg   1980
aggccttcac cattttagcc aagatgagcc ttcccagcgt ccccgtcttc ctagaggttt   2040
ctggccagtt tgatgttgag ttccggcttg ccgcggcctg ccgcaatgga aacatctata   2100
ttctgagaag agactccaag caccccaagt actgcatcga gctgagcgcc cagcctgtgg   2160
```

```
gacttatccg ggtacacaag gtcctagtgg tgggcagcac ccaagacagc ctgcatggct   2220

tcacccacaa ggggaagaag ctgtggacag tgcagatgcc cgcagccatc ctgaccatga   2280

acctcctgga gcagcattcc cggggcctgc aggccgtcat ggctgggctg gccaatggag   2340

aggtccgcat ttatcgtgac aaggccctgc tcaatgtcat ccacaccccg gatgcagtga   2400

ccagcctttg ctttggccgg tacgggcggg aggacaacac cctcatcatg accactcgag   2460

gtggtggcct gatcatcaag atcctgaagc gtacagcagt gtttgtagag ggaggaagtg   2520

aggtgggtcc cccaccagcc caggccatga aactcaatgt gccccgaaag acccggcttt   2580

acgtggatca gacactgcga gagcgggagg ctggcaccgc catgcaccgg gccttccaga   2640

cagacctata cctgctgcgc ctacgtgctg cccgcgccta cctgcaggcc ctcgagtcca   2700

gcctgagccc cctgtccacg acagcccgag agccactcaa gctgcacgcc gtggttcagg   2760

gccttggccc cacctttaag ctcacacttc acctgcagaa cacctcaaca acccgtcctg   2820

tcctggggct gctggtctgc ttcctgtaca acgaggcgct ctattccctg ccccgggcct   2880

tcttcaaggt acccttgctg gtgccagggc tcaactaccc cctggagacc tttgtggaga   2940

gtctcagtaa caagggcatc tcagacatca tcaaggtgct ggtgcttcga gaaggccaaa   3000

gtgcacccct gctgagtgcc cacgtcaaca tgcctgggag cgaggggctg gcggccgcct   3060

gagacttgtc gac                                                      3073
```

<210> SEQ ID NO 19
<211> LENGTH: 3080
<212> TYPE: DNA
<213> ORGANISM: Artificial sequence
<220> FEATURE:
<223> OTHER INFORMATION: Construct comprising UBC promoter and COSEQ1-
      BBS1 nucleotide sequence (referred to as UBC-COSEQ11BBS1)

<400> SEQUENCE: 19

```
actagtaacc cgtgtcggct ccagatctgg cctccgcgcc gggttttggc gcctcccgcg     60

ggcgcccccc tcctcacggc gagcgctgcc acgtcagacg aagggcgcag cgagcgtcct    120

gatccttccg cccggacgct caggacagcg gcccgctgct cataagactc ggccttagaa    180

ccccagtatc agcagaagga cattttagga cgggacttgg gtgactctag ggcactggtt    240

ttctttccag agagcggaac aggcgaggaa aagtagtccc ttctcggcga ttctgcggag    300

ggatctccgt ggggcggtga acgccgatga ttatataagg acgcgccggg tgtggcacag    360

ctagttccgt cgcagccggg atttgggtcg cggttcttgt ttgtggatcg ctgtgatcgt    420

cacttggtga gtagcgggct gctgggctgg ccggggcttt cgtggccgcc gggccgctcg    480

gtgggacgga agcgtgtgga gagaccgcca agggctgtag tctgggtccg cgagcaaggt    540

tgccctgaac tgggggttgg ggggagcgca gcaaaatggc ggctgttccc gagtcttgaa    600

tggaagacgc ttgtgaggcg ggctgtgagg tcgttgaaac aaggtggggg gcatggtggg    660

cggcaagaac ccaaggtctt gaggccttcg ctaatgcggg aaagctctta ttcgggtgag    720

atgggctggg gcaccatctg gggaccctga cgtgaagttt gtcactgact ggagaactcg    780

gtttgtcgtc tgttgcgggg gcggcagtta tggcggtgcc gttgggcagt gcacccgtac    840

ctttgggagc gcgcgccctc gtcgtgtcgt gacgtcaccc gttctgttgg cttataatgc    900

agggtggggc cacctgccgg taggtgtgcg gtaggctttt ctccgtcgca ggacgcaggg    960

ttcgggccta gggtaggctc tcctgaatcg acaggcgccg gacctctggt gaggggaggg   1020

ataagtgagg cgtcagtttc tttggtcggt tttatgtacc tatcttctta agtagctgaa   1080
```

-continued gctccggttt tgaactatgc gctcggggtt ggcgagtgtg ttttgtgaag ttttttaggc 1140 acctttgaa atgtaatcat ttgggtcaat atgtaatttt cagtgttaga ctagtaaatt 1200
gtccgctaaa ttctggccgt ttttggcttt tttgttagac gaagcttggg ctgcaggtcg 1260
agctcaagct tcgaattcgc caccatggct gccgccagca gttctgattc tgatgcctgt 1320
ggcgccgaga gcaacgaggc caattctaaa tggctggacg cccactacga ccccatggcc 1380
aatatccaca cctttagcgc ctgtctggcc ctggctgatc ttcatggcga cggcgagtat 1440
aagctggttg tgggagatct tggacctggc ggacagcagc ctagactgaa ggtgctgaag 1500
ggccctctcg tgatgacaga gtctcctctt cctgctctgc ctgccgccgc tgccacattt 1560
ctgatggaac agcacgagcc cagaacaccc gctctggctc ttgcttctgg cccttgcgtg 1620
tacgtgtaca agaacctgcg gccttacttc aagttcagcc tgcctcagct gcctcctaat 1680
cctctggaac aggacctgtg gaaccaggcc aaagaggaca gaatcgaccc tctgacactg 1740
aaagagatgc tggaatccat cagagagaca gccgaggaac ccctgtctat ccagagcctg 1800
agattcctgc agctggaact gagcgagatg gaagccttcg tgaaccagca caagagcaac 1860
agcatcaagc ggcagaccgt gatcaccacc atgaccacac tgaagaagaa cctggccgac 1920
gaggatgccg tgtcttgtct ggtgctgggc accgagaaca aagagctgct ggttctggat 1980
cccgaggcct tcacaatcct ggccaagatg tctctgccta gcgtgcccgt gtttctggaa 2040
gtgtccggcc agttcgacgt ggaatttcgg ctggccgctg cctgcagaaa cggcaacatc 2100
tacatcctgc ggagggacag caagcacccc aagtactgta tcgagctgtc tgcccagcct 2160
gtgggcctga ttagagtgca caaggtgctg gtcgtgggca gcacacagga tagcctgcac 2220
ggctttaccc acaagggcaa gaaactgtgg accgtgcaga tgccagccgc catcctgacc 2280
atgaatctgc tcgaacagca cagcagagga ctgcaggctg ttatggcagg actggctaat 2340
ggcgaagtgc ggatctacag agacaaggcc ctgctgaacg tgatccacac acctgatgcc 2400
gtgacaagcc tgtgcttcgg cagatacggc agagaggaca acaccctgat catgacaaca 2460
agaggcggcg gactgatcat caagatcctg aagagaaccg ccgtgttcgt ggaaggcgga 2520
tctgaagttg gacctcctcc agctcaggcc atgaagctga atgtgcccag aaagacccgg 2580
ctgtacgtgg accagacact gagagaaaga gaagccggca cagccatgca cagagccttc 2640
cagactgacc tgtacctgct gagactgaga gccgccagag cctatctgca ggccctggaa 2700
tctagcctgt ctcctctgag cacaaccgcc agagagcctc tgaaactgca cgctgtggtt 2760
caaggcctgg gacctacctt caagctgacc ctgcatctgc agaacaccag caccacaaga 2820
ccagtgctgg gcctgctcgt gtgcttcctg tacaatgagg ccctgtacag cctgccacgg 2880
gcctttttta aggtgccact gctggtgccc ggcctgaact accctctgga aacctttgtg 2940
gaaagcctga gcaacaaggg catcagcgac atcatcaaag tgctggtgct gagagagggc 3000
cagtctgctc ctctgctcag cgcccatgtg aatatgcctg gctctgaagg cctggcagcc 3060
gcttaagcgg ccgcgtcgac 3080

<210> SEQ ID NO 20
<211> LENGTH: 3080
<212> TYPE: DNA
<213> ORGANISM: Artificial sequence
<220> FEATURE:
<223> OTHER INFORMATION: Construct comprising UBC promoter and COSEQ2-
      BBS1 nucleotide sequence (referred to as UBC-COSEQ2-BBS1)

<400> SEQUENCE: 20

-continued actagtaacc cgtgtcggct ccagatctgg cctccgcgcc gggttttggc gcctcccgcg 60
ggcgcccccc tcctcacggc gagcgctgcc acgtcagacg aagggcgcag cgagcgtcct 120
gatccttccg cccggacgct caggacagcg gcccgctgct cataagactc ggccttagaa 180
ccccagtatc agcagaagga cattttagga cgggacttgg gtgactctag ggcactggtt 240
ttctttccag agagcggaac aggcgaggaa aagtagtccc ttctcggcga ttctgcggag 300
ggatctccgt ggggcggtga acgccgatga ttatataagg acgcgccggg tgtggcacag 360
ctagttccgt cgcagccggg atttgggtcg cggttcttgt ttgtggatcg ctgtgatcgt 420
cacttggtga gtagcgggct gctgggctgg ccggggcttt cgtggccgcc gggccgctcg 480
gtgggacgga agcgtgtgga gagaccgcca agggctgtag tctgggtccg cgagcaaggt 540
tgccctgaac tgggggttgg ggggagcgca gcaaaatggc ggctgttccc gagtcttgaa 600
tggaagacgc ttgtgaggcg ggctgtgagg tcgttgaaac aaggtggggg gcatggtggg 660
cggcaagaac ccaaggtctt gaggccttcg ctaatgcggg aaagctctta ttcgggtgag 720
atgggctggg gcaccatctg gggaccctga cgtgaagttt gtcactgact ggagaactcg 780
gtttgtcgtc tgttgcgggg gcggcagtta tggcggtgcc gttgggcagt gcacccgtac 840
ctttgggagc gcgcgccctc gtcgtgtcgt gacgtcaccc gttctgttgg cttataatgc 900
agggtggggc cacctgccgg taggtgtgcg gtaggctttt ctccgtcgca ggacgcaggg 960
ttcgggccta gggtaggctc tcctgaatcg acaggcgccg gacctctggt gaggggaggg 1020
ataagtgagg cgtcagtttc tttggtcggt tttatgtacc tatcttctta agtagctgaa 1080
gctccggttt tgaactatgc gctcggggtt ggcgagtgtg ttttgtgaag ttttttaggc 1140
accttttgaa atgtaatcat ttgggtcaat atgtaatttt cagtgttaga ctagtaaatt 1200
gtccgctaaa ttctggccgt ttttggcttt tttgttagac gaagcttggg ctgcaggtcg 1260
agctcaagct tcgaattcgc caccatggct gccgcctcta gctctgactc tgatgcatgt 1320
ggagcagagt ctaacgaggc caatagcaag tggctggacg cccactacga tcctatggcc 1380
aacatccaca cattctctgc ctgcctggcc ctggcagacc tgcacggcga tggagagtat 1440
aagctggtgg tgggcgacct gggacctggc ggccagcagc cacggctgaa ggtgctgaag 1500
ggccctctgg tcatgacaga gtccccactg cccgccctgc cagccgccgc cgccaccttc 1560
ctgatggagc agcacgagcc tagaacccca gccctggccc tggcctctgg cccctgcgtg 1620
tacgtgtata agaacctgcg gccctacttc aagtttagcc tgccacagct gccccctaac 1680
cctctggagc aggatctgtg gaatcaggcc aaggaggaca ggatcgatcc tctgacactg 1740
aaggagatgc tggagagcat ccgggagaca gccgaggagc cactgagcat ccagtccctg 1800
agattcctgc agctggagct gtccgagatg gaggcctttg tgaaccagca caagtctaat 1860
agcatcaagc gccagaccgt gatcaccaca atgaccacac tgaagaagaa cctggccgac 1920
gaggatgccg tgtcttgtct ggtgctgggc acagagaata aggagctgct ggtgctggac 1980
ccagaggcct tcaccatcct ggccaagatg tctctgccct ctgtgcccgt gttcctggag 2040
gtgagcggac agttcgacgt ggagtttcgg ctggctgccg cctgcagaaa cggcaatatc 2100
tacatcctgc ggagagatag caagcaccca aagtattgta ttgagctgtc cgcccagcct 2160
gtgggcctga tcagagtgca caaggtgctg gtggtgggca gcacccagga ctccctgcac 2220
ggcttcacac acaagggcaa gaagctgtgg accgtgcaga tgcccgccgc catcctgacc 2280
atgaacctgc tggagcagca cagcagaggc ctgcaggccg tgatggcagg cctggcaaat 2340
ggagaggtga ggatctaccg cgacaaggcc ctgctgaatg tgatccacac ccctgatgcc 2400

-continued gtgacatccc tgtgcttcgg ccggtatggc agagaggata acacactgat catgaccaca 2460
cggggcggcg gcctgatcat caagatcctg aagagaacag ccgtgtttgt ggagggcggc 2520
tctgaagtgg gcccaccccc tgcccaggcc atgaagctga atgtgcccag gaagacccgc 2580
ctgtacgtgg accagacact gagggaaaga gaggcaggaa cagcaatgca cagggccttc 2640
cagaccgatc tgtacctgct gagactgaga gcagcaagag cctatctgca ggccctggag 2700
agctccctgt ccccactgtc taccacagca agagaacccc tgaagctgca cgcagtggtg 2760
cagggcctgg gacccacctt caagctgaca ctgcacctgc agaacacatc caccacaagg 2820
cctgtgctgg gcctgctggt gtgcttcctg tacaatgagg ccctgtattc tctgccacgc 2880
gccttcttta aggtgccact gctggtgccc ggcctgaact atcccctgga gacattcgtg 2940
gagtccctgt ctaataaggg catctctgat atcatcaagg tgctggtgct gagagaagga 3000
cagtccgccc ctctgctgtc tgcccacgtg aatatgccag gcagcgaggg cctggctgcc 3060
gcctgagcgg ccgcgtcgac 3080

<210> SEQ ID NO 21
<211> LENGTH: 2418
<212> TYPE: DNA
<213> ORGANISM: Artificial sequence
<220> FEATURE:
<223> OTHER INFORMATION: Construct comprising CMV promoter and wild type BBS1 nucleotide sequence (referred to as CMV-WTBBS1)

<400> SEQUENCE: 21
actagttatt aatagtaatc aattacgggg tcattagttc atagcccata tatggagttc 60
cgcgttacat aacttacggt aaatggcccg cctggctgac cgcccaacga cccccgccca 120
ttgacgtcaa taatgacgta tgttcccata gtaacgccaa tagggacttt ccattgacgt 180
caatgggtgg agtatttacg gtaaactgcc cacttggcag tacatcaagt gtatcatatg 240
ccaagtacgc cccctattga cgtcaatgac ggtaaatggc ccgcctggca ttatgcccag 300
tacatgacct tatgggactt tcctacttgg cagtacatct acgtattagt catcgctatt 360
accatggtga tgcggttttg gcagtacatc aatgggcgtg gatagcggtt tgactcacgg 420
ggatttccaa gtctccaccc cattgacgtc aatgggagtt tgttttggca ccaaaatcaa 480
cgggactttc caaaatgtcg taacaactcc gccccattga cgcaaatggg cggtaggcgt 540
gtacggtggg aggtctatat aagcagagct ggtttagtga accgtcagat ccgctagcgc 600
taccggactc agatctcgaa ttccgatggc cgctgcgtcc tcatcggatt ccgacgcctg 660
cggagctgag agcaatgagg ccaattcgaa gtggttggat gcgcactacg acccaatggc 720
caatatccac accttttctg cctgcctagc gctggcagat ttacatgggg atggggaata 780
caagctggtg gtaggggacc ttggccctgg tgggcagcag ccccgcctga aggtgctcaa 840
aggaccactg gtgatgaccg aaagcccgct acctgctctg ccagctgctg ctgccacctt 900
cctcatggag caacatgagc cccggacccc agctctggca cttgcttcag gcccttgtgt 960
ctatgtgtat aagaatctca gaccctactt caagttcagc ctgccccaat tgcctccaaa 1020
tcctctggaa caagaccttt ggaaccaggc caaagaggac cgaatcgacc ccttaaccct 1080
gaaggagatg ctggagagca tccgggagac ggcagaggag cctttgtcca tccagtcact 1140
caggtttctg cagctggagc taagtgaaat ggaggcattt gtaaaccaac acaagtccaa 1200
ctccatcaag cggcagacag tcatcaccac catgaccacc ttgaagaaga acctggctga 1260
cgaggatgct gtgtcttgcc tggtgctggg caccgagaac aaggagctcc tggtgcttga 1320
ccccgaggcc ttcaccattt tagccaagat gagccttccc agcgtccccg tcttcctaga 1380
ggtttctggc cagtttgatg ttgagttccg gcttgccgcg gcctgccgca atggaaacat 1440
ctatattctg agaagagact ccaagcaccc caagtactgc atcgagctga gcgcccagcc 1500
tgtgggactt atccgggtac acaaggtcct agtggtgggc agcacccaag acagcctgca 1560
tggcttcacc cacaagggga agaagctgtg gacagtgcag atgcccgcag ccatcctgac 1620
catgaacctc ctggagcagc attcccgggg cctgcaggcc gtcatggctg ggctggccaa 1680
tggagaggtc cgcatttatc gtgacaaggc cctgctcaat gtcatccaca ccccggatgc 1740
agtgaccagc ctttgctttg gccggtacgg gcgggaggac aacaccctca tcatgaccac 1800
tcgaggtggt ggcctgatca tcaagatcct gaagcgtaca gcagtgtttg tagagggagg 1860
aagtgaggtg ggtcccccac cagcccaggc catgaaactc aatgtgcccc gaaagacccg 1920
gctttacgtg gatcagacac tgcgagagcg ggaggctggc accgccatgc accgggcctt 1980
ccagacagac ctatacctgc tgcgcctacg tgctgcccgc gcctacctgc aggccctcga 2040
gtccagcctg agcccccctgt ccacgacagc ccgagagcca ctcaagctgc acgccgtggt 2100
tcagggcctt ggccccacct ttaagctcac acttcacctg cagaacacct caacaacccg 2160
tcctgtcctg ggctgctgg tctgcttcct gtacaacgag gcgctctatt ccctgccccg 2220
ggccttcttc aaggtaccct tgctggtgcc agggctcaac tacccccctgg agacctttgt 2280 ggagagtctc agtaacaagg gcatctcaga catcatcaag gtgctggtgc ttcgagaagg 2340
ccaaagtgca cccctgctga gtgcccacgt caacatgcct gggagcgagg ggctggcggc 2400
cgcctgagac ttgtcgac 2418

<210> SEQ ID NO 22
<211> LENGTH: 2422
<212> TYPE: DNA
<213> ORGANISM: Artificial sequence
<220> FEATURE:
<223> OTHER INFORMATION: Construct comprising CMV promoter and COSEQ1-BBS1 nucleotide sequence (referred to as CMV-COSEQ1-BBS1)

<400> SEQUENCE: 22
actagttatt aatagtaatc aattacgggg tcattagttc atagcccata tatggagttc 60
cgcgttacat aacttacggt aaatggcccg cctggctgac cgcccaacga cccccgccca 120
ttgacgtcaa taatgacgta tgttcccata gtaacgccaa tagggacttt ccattgacgt 180
caatgggtgg agtatttacg gtaaactgcc cacttggcag tacatcaagt gtatcatatg 240
ccaagtacgc cccctattga cgtcaatgac ggtaaatggc ccgcctggca ttatgcccag 300
tacatgacct tatgggactt tcctacttgg cagtacatct acgtattagt catcgctatt 360
accatggtga tgcggttttg gcagtacatc aatgggcgtg gatagcggtt tgactcacgg 420
ggatttccaa gtctccaccc cattgacgtc aatgggagtt tgttttggca ccaaaatcaa 480
cgggactttc caaaatgtcg taacaactcc gccccattga cgcaaatggg cggtaggcgt 540
gtacggtggg aggtctatat aagcagagct ggtttagtga accgtcagat ccgctagcgc 600
taccggactc agatctcgaa ttcgccacca tggctgccgc cagcagttct gattctgatg 660
cctgtggcgc cgagagcaac gaggccaatt ctaaatggct ggacgcccac tacgacccca 720
tggccaatat ccacaccttt agcgcctgtc tggccctggc tgatcttcat ggcgacggcg 780
agtataagct ggttgtggga gatcttggac ctggcggaca gcagcctaga ctgaaggtgc 840
tgaagggccc tctcgtgatg acagagtctc ctcttcctgc tctgcctgcc gccgctgcca 900

```
catttctgat ggaacagcac gagcccagaa cacccgctct ggctcttgct tctggccctt    960

gcgtgtacgt gtacaagaac ctgcggcctt acttcaagtt cagcctgcct cagctgcctc   1020

ctaatcctct ggaacaggac ctgtggaacc aggccaaaga ggacagaatc gaccctctga   1080

cactgaaaga gatgctggaa tccatcagag agacagccga ggaacccctg tctatccaga   1140

gcctgagatt cctgcagctg gaactgagcg agatggaagc cttcgtgaac cagcacaaga   1200

gcaacagcat caagcggcag accgtgatca ccaccatgac cacactgaag aagaacctgg   1260

ccgacgagga tgccgtgtct tgtctggtgc tgggcaccga gaacaaagag ctgctggttc   1320

tggatcccga ggccttcaca atcctggcca agatgtctct gcctagcgtg cccgtgtttc   1380

tggaagtgtc cggccagttc gacgtggaat ttcggctggc cgctgcctgc agaaacggca   1440

acatctacat cctgcggagg gacagcaagc accccaagta ctgtatcgag ctgtctgccc   1500

agcctgtggg cctgattaga gtgcacaagg tgctggtcgt gggcagcaca caggatagcc   1560

tgcacggctt tacccacaag ggcaagaaac tgtggaccgt gcagatgcca gccgccatcc   1620

tgaccatgaa tctgctcgaa cagcacagca gaggactgca ggctgttatg gcaggactgg   1680

ctaatggcga agtgcggatc tacagagaca aggccctgct gaacgtgatc cacacacctg   1740

atgccgtgac aagcctgtgc ttcggcagat acggcagaga ggacaacacc ctgatcatga   1800

caacaagagg cggcggactg atcatcaaga tcctgaagag aaccgccgtg ttcgtggaag   1860

gcggatctga agttggacct cctccagctc aggccatgaa gctgaatgtg cccagaaaga   1920

cccggctgta cgtggaccag acactgagag aaagagaagc cggcacagcc atgcacagag   1980

ccttccagac tgacctgtac ctgctgagac tgagagccgc cagagcctat ctgcaggccc   2040

tggaatctag cctgtctcct ctgagcacaa ccgccagaga gcctctgaaa ctgcacgctg   2100

tggttcaagg cctgggacct accttcaagc tgaccctgca tctgcagaac accagcacca   2160

caagaccagt gctgggcctg ctcgtgtgct tcctgtacaa tgaggccctg tacagcctgc   2220

cacgggcctt ttttaaggtg ccactgctgg tgcccggcct gaactaccct ctggaaacct   2280

ttgtggaaag cctgagcaac aagggcatca gcgacatcat caaagtgctg gtgctgagag   2340

agggccagtc tgctcctctg ctcagcgccc atgtgaatat gcctggctct gaaggcctgg   2400

cagccgctta agcgccgtcg ac                                             2422
```

<210> SEQ ID NO 23
<211> LENGTH: 2425
<212> TYPE: DNA
<213> ORGANISM: Artificial sequence
<220> FEATURE:
<223> OTHER INFORMATION: Construct comprising CMV promoter and COSEQ2-BBS1 nucleotide sequence (referred to as CMV-COSEQ2-BBS1)

<400> SEQUENCE: 23

```
actagttatt aatagtaatc aattacgggg tcattagttc atagcccata tatggagttc     60

cgcgttacat aacttacggt aaatggcccg cctggctgac cgcccaacga cccccgccca    120

ttgacgtcaa taatgacgta tgttcccata gtaacgccaa tagggacttt ccattgacgt    180

caatgggtgg agtatttacg gtaaactgcc cacttggcag tacatcaagt gtatcatatg    240

ccaagtacgc cccctattga cgtcaatgac ggtaaatggc ccgcctggca ttatgcccag    300

tacatgacct tatgggactt tcctacttgg cagtacatct acgtattagt catcgctatt    360

accatggtga tgcggttttg gcagtacatc aatgggcgtg gatagcggtt tgactcacgg    420

ggatttccaa gtctccaccc cattgacgtc aatgggagtt tgttttggca ccaaaatcaa    480
```

cgggactttc caaaatgtcg taacaactcc gccccattga cgcaaatggg cggtaggcgt 540
gtacggtggg aggtctatat aagcagagct ggtttagtga accgtcagat ccgctagcgc 600
taccggactc agatctcgaa ttcgccacca tggctgccgc ctctagctct gactctgatg 660
catgtggagc agagtctaac gaggccaata gcaagtggct ggacgcccac tacgatccta 720
tggccaacat ccacacattc tctgcctgcc tggccctggc agacctgcac ggcgatggag 780
agtataagct ggtggtgggc gacctgggac ctggcggcca gcagccacgg ctgaaggtgc 840
tgaagggccc tctggtcatg acagagtccc cactgcccgc cctgccagcc gccgccgcca 900
ccttcctgat ggagcagcac gagcctagaa ccccagccct ggccctggcc tctggcccct 960
gcgtgtacgt gtataagaac ctgcggccct acttcaagtt tagcctgcca cagctgcccc 1020
ctaaccctct ggagcaggat ctgtggaatc aggccaagga ggacaggatc gatcctctga 1080
cactgaagga gatgctggag agcatccggg agacagccga ggagccactg agcatccagt 1140
ccctgagatt cctgcagctg gagctgtccg agatggaggc ctttgtgaac cagcacaagt 1200
ctaatagcat caagcgccag accgtgatca ccacaatgac cacactgaag aagaacctgg 1260
ccgacgagga tgccgtgtct tgtctggtgc tgggcacaga gaataaggag ctgctggtgc 1320
tggacccaga ggccttcacc atcctggcca agatgtctct gccctctgtg cccgtgttcc 1380
tggaggtgag cggacagttc gacgtggagt ttcggctggc tgccgcctgc agaaacggca 1440
atatctacat cctgcggaga gatagcaagc acccaaagta ttgtattgag ctgtccgccc 1500
agcctgtggg cctgatcaga gtgcacaagg tgctggtggt gggcagcacc caggactccc 1560
tgcacggctt cacacacaag ggcaagaagc tgtggaccgt gcagatgccc gccgccatcc 1620
tgaccatgaa cctgctggag cagcacagca gaggcctgca ggccgtgatg gcaggcctgg 1680
caaatggaga ggtgaggatc taccgcgaca aggccctgct gaatgtgatc cacacccctg 1740
atgccgtgac atccctgtgc ttcggccggt atggcagaga ggataacaca ctgatcatga 1800
ccacacgggg cggcggcctg atcatcaaga tcctgaagag aacagccgtg tttgtggagg 1860
gcggctctga agtgggccca ccccctgccc aggccatgaa gctgaatgtg cccaggaaga 1920
cccgcctgta cgtggaccag acactgaggg aaagagaggc aggaacagca atgcacaggg 1980
ccttccagac cgatctgtac ctgctgagac tgagagcagc aagagcctat ctgcaggccc 2040
tggagagctc cctgtcccca ctgtctacca cagcaagaga accccctgaag ctgcacgcag 2100 tggtgcaggg cctgggaccc accttcaagc tgacactgca cctgcagaac acatccacca 2160
caaggcctgt gctgggcctg ctggtgtgct tcctgtacaa tgaggccctg tattctctgc 2220
cacgcgcctt ctttaaggtg ccactgctgg tgcccggcct gaactatccc ctggagacat 2280
tcgtggagtc cctgtctaat aagggcatct ctgatatcat caaggtgctg gtgctgagag 2340
aaggacagtc cgcccctctg ctgtctgccc acgtgaatat gccaggcagc gagggcctgg 2400
ctgccgcctg agcggccgcg tcgac 2425

<210> SEQ ID NO 24
<211> LENGTH: 2261
<212> TYPE: DNA
<213> ORGANISM: Artificial sequence
<220> FEATURE:
<223> OTHER INFORMATION: Construct comprising CBA promoter and wild type BBS1 nucleotide sequence (referred to as CBA-WTBBS1)

<400> SEQUENCE: 24
actagtgtac atctacgtat tagtcatcgc tattaccatg gtcgaggtga gccccacgtt 60

-continued ctgcttcact ctccccatct cccccccctc cccaccccca attttgtatt tatttatttt 120
ttaattattt tgtgcagcga tgggggcggg gggggggggg gggcgcgcgc caggcggggc 180
ggggcggggc gaggggcggg gcggggcgag gcggagaggt gcggcggcag ccaatcagag 240
cggcgcgctc cgaaagtttc cttttatggc gaggcggcgg cggcggcggc cctataaaaa 300
gcgaagcgcg cggcgggcgg gagtcgctgc gcgctgcctt cgccccgtgc cccgctccgc 360
cgccgcctcg cgccgcccgc cccggctctg actgaccgcg ttactcccac aggtgagcgg 420
gcgggacggc ccttctcctc cgggctgtaa ttagcgcttg gaattccgat ggccgctgcg 480
tcctcatcgg attccgacgc ctgcggagct gagagcaatg aggccaattc gaagtggttg 540
gatgcgcact acgacccaat ggccaatatc cacacctttt ctgcctgcct agcgctggca 600
gatttacatg ggatggggga atacaagctg gtggtagggg accttggccc tggtgggcag 660
cagccccgcc tgaaggtgct caaaggacca ctggtgatga ccgaaagccc gctacctgct 720
ctgccagctg ctgctgccac cttcctcatg gagcaacatg agccccggac cccagctctg 780
gcacttgctt caggcccttg tgtctatgtg tataagaatc tcagacccta cttcaagttc 840
agcctgcccc aattgcctcc aaatcctctg gaacaagacc tttggaacca ggccaaagag 900
gaccgaatcg acccccttaac cctgaaggag atgctggaga gcatccggga gacggcagag 960
gagcctttgt ccatccagtc actcaggttt ctgcagctgg agctaagtga aatggaggca 1020
tttgtaaacc aacacaagtc caactccatc aagcggcaga cagtcatcac caccatgacc 1080
accttgaaga agaacctggc tgacgaggat gctgtgtctt gcctggtgct gggcaccgag 1140
aacaaggagc tcctggtgct tgaccccgag gccttcacca ttttagccaa gatgagcctt 1200
cccagcgtcc ccgtcttcct agaggtttct ggccagtttg atgttgagtt ccggcttgcc 1260
gcggcctgcc gcaatggaaa catctatatt ctgagaagag actccaagca ccccaagtac 1320
tgcatcgagc tgagcgccca gcctgtggga cttatccggg tacacaaggt cctagtggtg 1380
ggcagcaccc aagacagcct gcatggcttc acccacaagg ggaagaagct gtggacagtg 1440
cagatgcccg cagccatcct gaccatgaac ctcctggagc agcattcccg gggcctgcag 1500
gccgtcatgg ctgggctggc caatggagag gtccgcattt atcgtgacaa ggccctgctc 1560
aatgtcatcc acaccccgga tgcagtgacc agcctttgct ttggccggta cgggcgggag 1620
gacaacaccc tcatcatgac cactcgaggt ggtggcctga tcatcaagat cctgaagcgt 1680
acagcagtgt ttgtagaggg aggaagtgag gtgggtcccc caccagccca ggccatgaaa 1740
ctcaatgtgc cccgaaagac ccggctttac gtggatcaga cactgcgaga gcgggaggct 1800
ggcaccgcca tgcaccgggc cttccagaca gacctatacc tgctgcgcct acgtgctgcc 1860
cgcgcctacc tgcaggccct cgagtccagc ctgagccccc tgtccacgac agcccgagag 1920
ccactcaagc tgcacgccgt ggttcagggc cttggcccca cctttaagct cacacttcac 1980
ctgcagaaca cctcaacaac ccgtcctgtc ctggggctgc tggtctgctt cctgtacaac 2040
gaggcgctct attccctgcc ccgggccttc ttcaaggtac ccttgctggt gccagggctc 2100
aactaccccc tggagacctt tgtggagagt ctcagtaaca agggcatctc agacatcatc 2160
aaggtgctgg tgcttcgaga aggccaaagt gcacccctgc tgagtgccca cgtcaacatg 2220
cctgggagcg aggggctggc ggccgcctga gacttgtcga c 2261

<210> SEQ ID NO 25
<211> LENGTH: 2265
<212> TYPE: DNA

-continued

<213> ORGANISM: Artificial sequence
<220> FEATURE:
<223> OTHER INFORMATION: Construct comprising CBA promoter and COSEQ1-
BBS1 nucleotide sequence (referred to as CBA-COSEQ1-BBS1)

<400> SEQUENCE: 25

```
actagtgtac atctacgtat tagtcatcgc tattaccatg gtcgaggtga gccccacgtt     60
ctgcttcact ctccccatct ccccccctc cccaccccca attttgtatt tatttatttt    120
ttaattattt tgtgcagcga tgggggcggg gggggggggg gggcgcgcgc caggcggggc    180
ggggcggggc gaggggcggg gcggggcgag gcggagaggt gcggcggcag ccaatcagag    240
cggcgcgctc cgaaagtttc cttttatggc gaggcggcgg cggcggcggc cctataaaaa    300
gcgaagcgcg cggcgggcgg gagtcgctgc gcgctgcctt cgccccgtgc cccgctccgc    360
cgccgcctcg cgccgcccgc cccggctctg actgaccgcg ttactcccac aggtgagcgg    420
gcgggacggc ccttctcctc cgggctgtaa ttagcgcttg gaattcgcca ccatggctgc    480
cgccagcagt tctgattctg atgcctgtgg cgccgagagc aacgaggcca attctaaatg    540
gctggacgcc cactacgacc ccatggccaa tatccacacc tttagcgcct gtctggccct    600
ggctgatctt catggcgacg gcgagtataa gctggttgtg ggagatcttg gacctggcgg    660
acagcagcct agactgaagg tgctgaaggg ccctctcgtg atgacagagt ctcctcttcc    720
tgctctgcct gccgccgctg ccacatttct gatggaacag cacgagccca gaacacccgc    780
tctggctctt gcttctggcc cttgcgtgta cgtgtacaag aacctgcggc cttacttcaa    840
gttcagcctg cctcagctgc ctcctaatcc tctggaacag gacctgtgga accaggccaa    900
agaggacaga atcgaccctc tgacactgaa agagatgctg gaatccatca gagagacagc    960
cgaggaaccc ctgtctatcc agagcctgag attcctgcag ctggaactga gcgagatgga   1020
agccttcgtg aaccagcaca agagcaacag catcaagcgg cagaccgtga tcaccaccat   1080
gaccacactg aagaagaacc tggccgacga ggatgccgtg tcttgtctgg tgctgggcac   1140
cgagaacaaa gagctgctgg ttctggatcc cgaggccttc acaatcctgg ccaagatgtc   1200
tctgcctagc gtgcccgtgt ttctggaagt gtccggccag ttcgacgtgg aatttcggct   1260
ggccgctgcc tgcagaaacg gcaacatcta catcctgcgg agggacagca agcaccccaa   1320
gtactgtatc gagctgtctg cccagcctgt gggcctgatt agagtgcaca aggtgctggt   1380
cgtgggcagc acacaggata gcctgcacgg ctttacccac aagggcaaga aactgtggac   1440
cgtgcagatg ccagccgcca tcctgaccat gaatctgctc gaacagcaca gcagaggact   1500
gcaggctgtt atggcaggac tggctaatgg cgaagtgcgg atctacagag acaaggccct   1560
gctgaacgtg atccacacac ctgatgccgt gacaagcctg tgcttcggca gatacggcag   1620
agaggacaac accctgatca tgacaacaag aggcggcgga ctgatcatca agatcctgaa   1680
gagaaccgcc gtgttcgtgg aaggcggatc tgaagttgga cctcctccag ctcaggccat   1740
gaagctgaat gtgcccagaa agacccggct gtacgtggac cagacactga gagaaagaga   1800
agccggcaca gccatgcaca gagccttcca gactgacctg tacctgctga gactgagagc   1860
cgccagagcc tatctgcagg ccctggaatc tagcctgtct cctctgagca caaccgccag   1920
agagcctctg aaactgcacg ctgtggttca aggcctggga cctaccttca agctgaccct   1980
gcatctgcag aacaccagca ccacaagacc agtgctgggc ctgctcgtgt gcttcctgta   2040
caatgaggcc ctgtacagcc tgccacgggc ctttttttaag gtgccactgc tggtgcccgg   2100
cctgaactac cctctggaaa cctttgtgga aagcctgagc aacaagggca tcagcgacat   2160
```

-continued catcaaagtg ctggtgctga gagagggcca gtctgctcct ctgctcagcg cccatgtgaa 2220
tatgcctggc tctgaaggcc tggcagccgc ttaagcgccg tcgac 2265

<210> SEQ ID NO 26
<211> LENGTH: 2268
<212> TYPE: DNA
<213> ORGANISM: Artificial sequence
<220> FEATURE:
<223> OTHER INFORMATION: Construct comprising CBA promoter and COSEQ2-
BBS1 nucleotide sequence (referred to as CBA-COSEQ2-BBS1)

<400> SEQUENCE: 26
actagtgtac atctacgtat tagtcatcgc tattaccatg gtcgaggtga gccccacgtt 60
ctgcttcact ctccccatct cccccccctc cccaccccca attttgtatt tatttatttt 120
ttaattattt tgtgcagcga tgggggcggg gggggggggg gggcgcgcgc caggcggggc 180
ggggcggggc gaggggcggg gcggggcgag gcggagaggt gcggcggcag ccaatcagag 240
cggcgcgctc cgaaagtttc cttttatggc gaggcggcgg cggcggcggc cctataaaaa 300
gcgaagcgcg cggcgggcgg gagtcgctgc gcgctgcctt cgccccgtgc cccgctccgc 360
cgccgcctcg cgccgcccgc cccggctctg actgaccgcg ttactcccac aggtgagcgg 420
gcgggacggc ccttctcctc cgggctgtaa ttagcgcttg gaattcgcca ccatggctgc 480
cgcctctagc tctgactctg atgcatgtgg agcagagtct aacgaggcca atagcaagtg 540
gctggacgcc cactacgatc ctatggccaa catccacaca ttctctgcct gcctggccct 600
ggcagacctg cacggcgatg gagagtataa gctggtggtg ggcgacctgg gacctggcgg 660
ccagcagcca cggctgaagg tgctgaaggg ccctctggtc atgacagagt ccccactgcc 720
cgccctgcca gccgccgccg ccaccttcct gatggagcag cacgagccta gaaccccagc 780
cctggccctg gcctctggcc cctgcgtgta cgtgtataag aacctgcggc cctacttcaa 840
gtttagcctg ccacagctgc cccctaaccc tctggagcag gatctgtgga atcaggccaa 900
ggaggacagg atcgatcctc tgacactgaa ggagatgctg gagagcatcc gggagacagc 960
cgaggagcca ctgagcatcc agtccctgag attcctgcag ctggagctgt ccgagatgga 1020
ggcctttgtg aaccagcaca agtctaatag catcaagcgc cagaccgtga tcaccacaat 1080
gaccacactg aagaagaacc tggccgacga ggatgccgtg tcttgtctgg tgctgggcac 1140
agagaataag gagctgctgg tgctggaccc agaggccttc accatcctgg ccaagatgtc 1200
tctgccctct gtgcccgtgt tcctggaggt gagcggacag ttcgacgtgg agtttcggct 1260
ggctgccgcc tgcagaaacg gcaatatcta catcctgcgg agagatagca agcacccaaa 1320
gtattgtatt gagctgtccg cccagcctgt gggcctgatc agagtgcaca aggtgctggt 1380
ggtgggcagc acccaggact ccctgcacgg cttcacacac aagggcaaga agctgtggac 1440
cgtgcagatg cccgccgcca tcctgaccat gaacctgctg gagcagcaca gcagaggcct 1500
gcaggccgtg atggcaggcc tggcaaatgg agaggtgagg atctaccgcg acaaggccct 1560
gctgaatgtg atccacaccc ctgatgccgt gacatccctg tgcttcggcc ggtatggcag 1620
agaggataac acactgatca tgaccacacg gggcggcggc ctgatcatca agatcctgaa 1680
gagaacagcc gtgtttgtgg agggcggctc tgaagtgggc ccacccccctg cccaggccat 1740 gaagctgaat gtgcccagga agacccgcct gtacgtggac cagacactga gggaaagaga 1800
ggcaggaaca gcaatgcaca gggccttcca gaccgatctg tacctgctga gactgagagc 1860
agcaagagcc tatctgcagg ccctggagag ctccctgtcc ccactgtcta ccacagcaag 1920
agaacccctg aagctgcacg cagtggtgca gggcctggga cccaccttca agctgacact 1980
gcacctgcag aacacatcca ccacaaggcc tgtgctgggc ctgctggtgt gcttcctgta 2040
caatgaggcc ctgtattctc tgccacgcgc cttctttaag gtgccactgc tggtgcccgg 2100
cctgaactat cccctggaga cattcgtgga gtccctgtct aataagggca tctctgatat 2160
catcaaggtg ctggtgctga gagaaggaca gtccgcccct ctgctgtctg cccacgtgaa 2220
tatgccaggc agcgagggcc tggctgccgc ctgagcggcc gcgtcgac 2268

<210> SEQ ID NO 27
<211> LENGTH: 2504
<212> TYPE: DNA
<213> ORGANISM: Artificial sequence
<220> FEATURE:
<223> OTHER INFORMATION: Construct comprising CAG promoter and wild type BBS1 nucleotide sequence (referred to as CAG-WTBBS1)

<400> SEQUENCE: 27
actagttcct ggaggggtgg agtcgtgacc taggccattg acgtcaataa tgacgtatgt 60
tcccatagta acgccaatag ggactttcca ttgacgtcaa tgggtggagt atttacggta 120
aactgcccac ttggcagtac atcaagtgta tcatatgcca agtacgcccc ctattgacgt 180
caatgacggt aaatggcccg cctggcatta tgcccagtac atgaccttat gggactttcc 240
tacttggcag tacatctacg tattagtcat cgctattacc atggtcgagg tgagccccac 300
gttctgcttc actctcccca tctccccccc ctccccaccc ccaattttgt atttatttat 360
tttttaatta ttttgtgcag cgatgggggc gggggggggg ggggggcgcg cgccaggcgg 420
ggcggggcgg ggcgaggggc ggggcggggc gaggcggaga ggtgcggcgg cagccaatca 480
gagcggcgcg ctccgaaagt ttccttttat ggcgaggcgg cggcggcggc ggccctataa 540
aaagcgaagc gcgcggcggg cgggagtcgc tgcgcgctgc cttcgccccg tgccccgctc 600
cgccgccgcc tcgcgccgcc cgccccggct ctgactgacc gcgttactcc cacaggtgag 660
cgggcgggac ggcccttctc ctccgggctg taattagcgc ttggaattcc gatggccgct 720
gcgtcctcat cggattccga cgcctgcgga gctgagagca atgaggccaa ttcgaagtgg 780
ttggatgcgc actacgaccc aatggccaat atccacacct tttctgcctg cctagcgctg 840
gcagatttac atggggatgg ggaatacaag ctggtggtag gggaccttgg ccctggtggg 900
cagcagcccc gcctgaaggt gctcaaagga ccactggtga tgaccgaaag cccgctacct 960
gctctgccag ctgctgctgc caccttcctc atggagcaac atgagccccg gaccccagct 1020
ctggcacttg cttcaggccc ttgtgtctat gtgtataaga atctcagacc ctacttcaag 1080
ttcagcctgc cccaattgcc tccaaatcct ctggaacaag acctttggaa ccaggccaaa 1140
gaggaccgaa tcgacccctt aaccctgaag gagatgctgg agagcatccg ggagacggca 1200
gaggagcctt tgtccatcca gtcactcagg tttctgcagc tggagctaag tgaaatggag 1260
gcatttgtaa accaacacaa gtccaactcc atcaagcggc agacagtcat caccaccatg 1320
accaccttga agaagaacct ggctgacgag gatgctgtgt cttgcctggt gctgggcacc 1380
gagaacaagg agctcctggt gcttgacccc gaggccttca ccattttagc caagatgagc 1440
cttcccagcg tccccgtctt cctagaggtt tctggccagt ttgatgttga gttccggctt 1500
gccgcggcct gccgcaatgg aaacatctat attctgagaa gagactccaa gcaccccaag 1560
tactgcatcg agctgagcgc ccagcctgtg ggacttatcc gggtacacaa ggtcctagtg 1620
gtgggcagca cccaagacag cctgcatggc ttcacccaca aggggaagaa gctgtggaca 1680

```
gtgcagatgc ccgcagccat cctgaccatg aacctcctgg agcagcattc ccggggcctg   1740

caggccgtca tggctgggct ggccaatgga gaggtccgca tttatcgtga caaggccctg   1800

ctcaatgtca tccacacccc ggatgcagtg accagccttt gctttggccg gtacgggcgg   1860

gaggacaaca ccctcatcat gaccactcga ggtggtggcc tgatcatcaa gatcctgaag   1920

cgtacagcag tgtttgtaga gggaggaagt gaggtgggtc cccccaccagc ccaggccatg  1980

aaactcaatg tgccccgaaa gacccggctt tacgtggatc agacactgcg agagcgggag   2040

gctggcaccg ccatgcaccg ggccttccag acagacctat acctgctgcg cctacgtgct   2100

gcccgcgcct acctgcaggc cctcgagtcc agcctgagcc ccctgtccac gacagcccga   2160

gagccactca agctgcacgc cgtggttcag ggccttggcc ccacctttaa gctcacactt   2220

cacctgcaga acacctcaac aacccgtcct gtcctggggc tgctggtctg cttcctgtac   2280

aacgaggcgc tctattccct gccccgggcc ttcttcaagg taccccttgct ggtgccaggg  2340

ctcaactacc ccctggagac ctttgtggag agtctcagta acaagggcat ctcagacatc   2400

atcaaggtgc tggtgcttcg agaaggccaa agtgcacccc tgctgagtgc ccacgtcaac   2460

atgcctggga gcgaggggct ggcggccgcc tgagacttgt cgac                    2504
```

<210> SEQ ID NO 28
<211> LENGTH: 2508
<212> TYPE: DNA
<213> ORGANISM: Artificial sequence
<220> FEATURE:
<223> OTHER INFORMATION: Construct comprising CAG promoter and COSEQ1-
      BBS1 nucleotide sequence (referred to as CAG-COSEQ1-BBS1)

<400> SEQUENCE: 28

```
actagttcct ggaggggtgg agtcgtgacc taggccattg acgtcaataa tgacgtatgt     60

tcccatagta acgccaatag ggactttcca ttgacgtcaa tgggtggagt atttacggta    120

aactgcccac ttggcagtac atcaagtgta tcatatgcca agtacgcccc ctattgacgt    180

caatgacggt aaatggcccg cctggcatta tgcccagtac atgaccttat gggactttcc    240

tacttggcag tacatctacg tattagtcat cgctattacc atggtcgagg tgagccccac    300

gttctgcttc actctcccca tctccccccc ctccccaccc ccaattttgt atttatttat    360

tttttaatta ttttgtgcag cgatgggggc gggggggggg ggggggcgcg cgccaggcgg    420

ggcggggcgg ggcgaggggc ggggcggggc gaggcggaga ggtgcggcgg cagccaatca    480

gagcggcgcg ctccgaaagt ttccttttat ggcgaggcgg cggcggcggc ggccctataa    540

aaagcgaagc gcgcggcggg cgggagtcgc tgcgcgctgc cttcgccccg tgccccgctc    600

cgccgccgcc tcgcgccgcc cgccccggct ctgactgacc gcgttactcc cacaggtgag    660

cgggcgggac ggcccttctc ctccgggctg taattagcgc ttggaattcg ccaccatggc    720

tgccgccagc agttctgatt ctgatgcctg tggcgccgag agcaacgagg ccaattctaa    780

atggctggac gcccactacg accccatggc caatatccac acctttagcg cctgtctggc    840

cctggctgat cttcatggcg acggcgagta taagctggtt gtgggagatc ttggacctgg    900

cggacagcag cctagactga aggtgctgaa gggccctctc gtgatgacag agtctcctct    960

tcctgctctg cctgccgccg ctgccacatt tctgatggaa cagcacgagc ccagaacacc   1020

cgctctggct cttgcttctg gcccttgcgt gtacgtgtac aagaacctgc ggccttactt   1080

caagttcagc ctgcctcagc tgcctcctaa tcctctggaa caggacctgt ggaaccaggc   1140

caaagaggac agaatcgacc ctctgacact gaaagagatg ctggaatcca tcagagagac   1200
```

agccgaggaa cccctgtcta tccagagcct gagattcctg cagctggaac tgagcgagat 1260
ggaagccttc gtgaaccagc acaagagcaa cagcatcaag cggcagaccg tgatcaccac 1320
catgaccaca ctgaagaaga acctggccga cgaggatgcc gtgtcttgtc tggtgctggg 1380
caccgagaac aaagagctgc tggttctgga tcccgaggcc ttcacaatcc tggccaagat 1440
gtctctgcct agcgtgcccg tgtttctgga agtgtccggc cagttcgacg tggaatttcg 1500
gctggccgct gcctgcagaa acggcaacat ctacatcctg cggagggaca gcaagcaccc 1560
caagtactgt atcgagctgt ctgcccagcc tgtgggcctg attagagtgc acaaggtgct 1620
ggtcgtgggc agcacacagg atagcctgca cggctttacc cacaagggca agaaactgtg 1680
gaccgtgcag atgccagccg ccatcctgac catgaatctg ctcgaacagc acagcagagg 1740
actgcaggct gttatggcag gactggctaa tggcgaagtg cggatctaca gagacaaggc 1800
cctgctgaac gtgatccaca cacctgatgc cgtgacaagc ctgtgcttcg gcagatacgg 1860
cagagaggac aacaccctga tcatgacaac aagaggcggc ggactgatca tcaagatcct 1920
gaagagaacc gccgtgttcg tggaaggcgg atctgaagtt ggacctcctc cagctcaggc 1980
catgaagctg aatgtgccca gaaagacccg gctgtacgtg gaccagacac tgagagaaag 2040
agaagccggc acagccatgc acagagcctt ccagactgac ctgtacctgc tgagactgag 2100
agccgccaga gcctatctgc aggccctgga atctagcctg tctcctctga gcacaaccgc 2160
cagagagcct ctgaaactgc acgctgtggt tcaaggcctg ggacctacct tcaagctgac 2220
cctgcatctg cagaacacca gcaccacaag accagtgctg ggcctgctcg tgtgcttcct 2280
gtacaatgag gccctgtaca gcctgccacg ggcctttttt aaggtgccac tgctggtgcc 2340
cggcctgaac taccctctgg aaacctttgt ggaaagcctg agcaacaagg gcatcagcga 2400
catcatcaaa gtgctggtgc tgagagaggg ccagtctgct cctctgctca gcgcccatgt 2460
gaatatgcct ggctctgaag gcctggcagc cgcttaagcg ccgtcgac 2508

<210> SEQ ID NO 29
<211> LENGTH: 2511
<212> TYPE: DNA
<213> ORGANISM: Artificial sequence
<220> FEATURE:
<223> OTHER INFORMATION: Construct comprising CAG promoter and COSEQ2-BBS1 nucleotide sequence (referred to as CAG-COSEQ2-BBS1)

<400> SEQUENCE: 29
actagttcct ggaggggtgg agtcgtgacc taggccattg acgtcaataa tgacgtatgt 60
tcccatagta acgccaatag ggactttcca ttgacgtcaa tgggtggagt atttacggta 120
aactgcccac ttggcagtac atcaagtgta tcatatgcca agtacgcccc ctattgacgt 180
caatgacggt aaatggcccg cctggcatta tgcccagtac atgaccttat gggactttcc 240
tacttggcag tacatctacg tattagtcat cgctattacc atggtcgagg tgagccccac 300
gttctgcttc actctcccca tctccccccc ctccccaccc ccaattttgt atttatttat 360
tttttaatta ttttgtgcag cgatgggggc gggggggggg ggggggcgcg cgccaggcgg 420
ggcggggcgg ggcgaggggc ggggcggggc gaggcggaga ggtgcggcgg cagccaatca 480
gagcggcgcg ctccgaaagt ttccttttat ggcgaggcgg cggcggcggc ggccctataa 540
aaagcgaagc gcgcggcggg cgggagtcgc tgcgcgctgc cttcgccccg tgccccgctc 600
cgccgccgcc tcgcgccgcc cgccccggct ctgactgacc gcgttactcc cacaggtgag 660
cgggcgggac ggcccttctc ctccgggctg taattagcgc ttggaattcg ccaccatggc 720

```
tgccgcctct agctctgact ctgatgcatg tggagcagag tctaacgagg ccaatagcaa    780
gtggctggac gcccactacg atcctatggc caacatccac acattctctg cctgcctggc    840
cctggcagac ctgcacggcg atggagagta taagctggtg gtgggcgacc tgggacctgg    900
cggccagcag ccacggctga aggtgctgaa gggccctctg gtcatgacag agtccccact    960
gcccgccctg ccagccgccg ccgccacctt cctgatggag cagcacgagc ctagaacccc   1020
agccctggcc ctggcctctg gcccctgcgt gtacgtgtat aagaacctgc ggccctactt   1080
caagtttagc ctgccacagc tgccccctaa ccctctggag caggatctgt ggaatcaggc   1140
caaggaggac aggatcgatc ctctgacact gaaggagatg ctggagagca tccgggagac   1200
agccgaggag ccactgagca tccagtccct gagattcctg cagctggagc tgtccgagat   1260
ggaggccttt gtgaaccagc acaagtctaa tagcatcaag cgccagaccg tgatcaccac   1320
aatgaccaca ctgaagaaga acctggccga cgaggatgcc gtgtcttgtc tggtgctggg   1380
cacagagaat aaggagctgc tggtgctgga cccagaggcc ttcaccatcc tggccaagat   1440
gtctctgccc tctgtgcccg tgttcctgga ggtgagcgga cagttcgacg tggagtttcg   1500
gctggctgcc gcctgcagaa acggcaatat ctacatcctg cggagagata gcaagcaccc   1560
aaagtattgt attgagctgt ccgcccagcc tgtgggcctg atcagagtgc acaaggtgct   1620
ggtggtgggc agcacccagg actccctgca cggcttcaca cacaagggca agaagctgtg   1680
gaccgtgcag atgcccgccg ccatcctgac catgaacctg ctggagcagc acagcagagg   1740
cctgcaggcc gtgatggcag gcctggcaaa tggagaggtg aggatctacc gcgacaaggc   1800
cctgctgaat gtgatccaca cccctgatgc cgtgacatcc ctgtgcttcg gccggtatgg   1860
cagagaggat aacacactga tcatgaccac acggggcggc ggcctgatca tcaagatcct   1920
gaagagaaca gccgtgtttg tggagggcgg ctctgaagtg ggcccacccc ctgcccaggc   1980
catgaagctg aatgtgccca ggaagacccg cctgtacgtg gaccagacac tgagggaaag   2040
agaggcagga acagcaatgc acagggcctt ccagaccgat ctgtacctgc tgagactgag   2100
agcagcaaga gcctatctgc aggccctgga gagctccctg tccccactgt ctaccacagc   2160
aagagaaccc ctgaagctgc acgcagtggt gcagggcctg ggacccacct tcaagctgac   2220
actgcacctg cagaacacat ccaccacaag gcctgtgctg ggcctgctgg tgtgcttcct   2280
gtacaatgag gccctgtatt ctctgccacg cgccttcttt aaggtgccac tgctggtgcc   2340
cggcctgaac tatcccctgg agacattcgt ggagtccctg tctaataagg gcatctctga   2400
tatcatcaag gtgctggtgc tgagagaagg acagtccgcc cctctgctgt ctgcccacgt   2460
gaatatgcca ggcagcgagg gcctggctgc cgcctgagcg gccgcgtcga c            2511
```

```
<210> SEQ ID NO 30
<211> LENGTH: 3428
<212> TYPE: DNA
<213> ORGANISM: Artificial sequence
<220> FEATURE:
<223> OTHER INFORMATION: Construct comprising EFS promoter and wild type
      BBS10 nucleotide sequence (referred to as EFS-WTBBS10)

<400> SEQUENCE: 30

actagtgggc agatctcgat cgagttgggc cccagagctt ggctccggtg cccgtcagtg     60
ggcagagcgc acatcgccca cagtccccga gaagttgtgg ggaggggtcg gcaattgaac    120
cggtgcctag agaaggtggc gcggggtaaa ctgggaaagt gatgtcgtgt actggctccg    180
cctttttccc gagggtgggg gagaaccgta tataagtgca gtagtcgccg tgaacgttct    240
```

-continued

```
ttttcgcaac gggtttgccg ccagaacaca ggtaagtgcc gtgtgtggtt cccgcgggcc    300
tggcctcttt acgggttatg gcccttgcgt gccttgaatt acttccacct ggctgcagta    360
cgtgattctt gatcccgagc ttcgggttgg aagtgggtgg gagagttcga ggccttgcgc    420
ttaaggagcc ccttcgcctc gtgcttgagt tgaggcctgg cctgggcgct ggggccgccg    480
cgtgcgaatc tggtggcacc ttcgcgcctg tctcgctgct ttcgataagt ctctagccat    540
ttaaaatttt tgatgacctg ctgcgacgct ttttttctgg caagatagtc ttgtaaatgc    600
gggccaagat ctgcacactg gtatttcggt ttttggggcc gcgggcggcg acggggcccg    660
tgcgtcccag cgcacatgtt cggcgaggcg gggcctgcga gcgcggccac cgagaatcgg    720
acgggggtag tctcaagctg gccggcctgc tctggtgcct ggcctcgcgc cgccgtgtat    780
cgccccgccc tgggcggcaa ggctggcccg gtcggcacca gttgcgtgag cggaaagatg    840
gccgcttccc ggccctgctg cagggagctc aaaatggagg acgcggcgct cgggagagcg    900
ggcgggtgag tcacccacac aaaggaaaag ggcctttccg tcctcagccg tcgcttcatg    960
tgactccacg gagtaccggg cgccgtccag gcacctcgat tagttctcga gcttttggag   1020
tacgtcgtct ttaggttggg gggaggggtt ttatgcgatg gagtttcccc acactgagtg   1080
ggtggagact gaagttaggc cagcttggca cttgatgtaa ttctccttgg aatttgccct   1140
ttttgagttt ggatcttggt tcattctcaa gcctcagaca gtggttcaaa gtttttttct   1200
tccatttcag gtgtcgtgac catgagcttc gaattcgcca ccatgttaag ttctatggcc   1260
gctgcagggt ctgtgaaggc ggcgttgcag gtggccgagg tgctggaagc catcgtgagc   1320
tgctgcgtgg ggcccgaggg acggcaagtt ttgtgtacga agcccactgg cgaggtgctt   1380
ctcagccgga atggaggccg cctcctggag gcgctacact tagagcatcc catagccagg   1440
atgatagtgg actgtgtttc cagtcatctc aaaaaaacag gagatggtgc aaaaacattt   1500
attatctttc tttgccattt gcttagagga cttcatgcaa tcacagacag agaaaaggat   1560
cctttgatgt gtgaaaacat tcaaacccat ggaaggcatt ggaaaaattg ttctcggtgg   1620
aaatttattt cccaggctct cctaacgttt cagacacaaa tattagacgg tattatggac   1680
cagtacctaa gtagacactt tttgtctatc ttttcgtctg ctaaagagag aacattgtgt   1740
aggagctctt tagagttgct cttagaagca tacttttgtg gaagagtggg aagaaataat   1800
cataaattta tttcacagtt gatgtgtgac tacttttca agtgtatgac ttgtaaaagt   1860
gggattggtg tatttgagtt agtggatgac cattttgtag agttgaatgt tggtgtcact   1920
ggccttcctg tttcagattc caggatcata gctggtcttg tgcttcagaa agatttttct   1980
gtgtaccgcc cagcagatgg tgacatgcga atggtgatag taacagaaac cattcagcct   2040
ctttttcca cttctggatc agagtttatt ctaaattcag aagcacagtt tcagacatct   2100
caattttgga ttatggaaaa gacaaaagca ataatgaaac atctacatag tcagaatgta   2160
aaattgctca tatctagtgt gaaacaacca gatttagtta gttattatgc aggggtgaat   2220
ggcatatcag tggttgagtg tttatcatca gaagaagttt ctcttatccg gaggatcatt   2280
ggtctttctc catttgtacc accacaggcc ttttcgcagt gtgaaatacc taacactgct   2340
ttggtgaaat tttgtaaacc tcttatcctt agatccaaaa gatatgttca tctaggcttg   2400
ataagcacat gtgcatttat accacactct atagttcttt gtggaccagt gcatggtctc   2460
attgaacaac atgaggatgc tttacatgga gcacttaaaa tgcttcggca attatttaaa   2520
gaccttgatc taaattacat gacacaaacc aatgaccaaa atggcacttc aagtcttttt   2580
atttataaga acagtggaga aagttatcaa gcaccagatc ctggtaatgg ctcaatacaa   2640
```

aggccttatc aggacacagt tgcagagaac aaagatgcat tggaaaaaac tcaaacatat 2700
ttaaaagtac attctaattt ggtaattcca gatgtagaat tagaaacata tattccgtat 2760
tcaaccccca cactgacacc aacagataca ttccaaacag ttgaaacgct gacatgtttg 2820
tctttggaaa gaaacaggct aactgattat tatgaaccat tactcaagaa caattccact 2880
gcttattcaa caaggggaaa tagaatagaa atttcttacg aaaatttaca ggtcacaaat 2940
attactagaa agggaagcat gttaccagtg agctgtaagt taccgaatat gggtacttcc 3000
cagagttacc tttcctcatc tatgccagct ggttgtgttt tgccagtagg tggtaatttt 3060
gagatcttgt tacattacta tcttctcaat tatgccaaaa aatgccatca atcagaagaa 3120
accatggtta gtatgataat agctaatgca cttttaggca ttcccaaagt cctttataaa 3180
tctaaaacag gaaagtacag ctttccacat acatatataa gagctgtcca tgcactgcaa 3240
accaatcaac ccttggtaag cagtcagaca ggtttggaat cagtaatggg taaataccag 3300
ctactaactt cagttcttca gtgtttgaca aaaatattaa ccattgacat ggtaatcact 3360
gttaagagac accctcagaa agttcacaat caagattcag aagatgaact ataagcggcc 3420
gcgtcgac 3428

<210> SEQ ID NO 31
<211> LENGTH: 3425
<212> TYPE: DNA
<213> ORGANISM: Artificial sequence
<220> FEATURE:
<223> OTHER INFORMATION: Construct comprising EFS promoter and COSEQ1-
BBS10 nucleotide sequence (referred to as EFS-COSEQ1-BBS10)

<400> SEQUENCE: 31
actagtgggc agatctcgat cgagttgggc cccagagctt ggctccggtg cccgtcagtg 60
ggcagagcgc acatcgccca cagtccccga gaagttgtgg ggaggggtcg gcaattgaac 120
cggtgcctag agaaggtggc gcggggtaaa ctgggaaagt gatgtcgtgt actggctccg 180
cctttttccc gagggtgggg gagaaccgta tataagtgca gtagtcgccg tgaacgttct 240
ttttcgcaac gggtttgccg ccagaacaca ggtaagtgcc gtgtgtggtt cccgcgggcc 300
tggcctcttt acgggttatg gcccttgcgt gccttgaatt acttccacct ggctgcagta 360
cgtgattctt gatcccgagc ttcgggttgg aagtgggtgg gagagttcga ggccttgcgc 420
ttaaggagcc ccttcgcctc gtgcttgagt tgaggcctgg cctgggcgct ggggccgccg 480
cgtgcgaatc tggtggcacc ttcgcgcctg tctcgctgct ttcgataagt ctctagccat 540
ttaaaatttt tgatgacctg ctgcgacgct ttttttctgg caagatagtc ttgtaaatgc 600
gggccaagat ctgcacactg gtatttcggt ttttggggcc gcgggcggcg acggggcccg 660
tgcgtcccag cgcacatgtt cggcgaggcg gggcctgcga gcgcggccac cgagaatcgg 720
acgggggtag tctcaagctg gccggcctgc tctggtgcct ggcctcgcgc cgccgtgtat 780
cgccccgccc tgggcggcaa ggctggcccg gtcggcacca gttgcgtgag cggaaagatg 840
gccgcttccc ggccctgctg cagggagctc aaaatggagg acgcggcgct cgggagagcg 900
ggcgggtgag tcacccacac aaaggaaaag ggcctttccg tcctcagccg tcgcttcatg 960
tgactccacg gagtaccggg cgccgtccag gcacctcgat tagttctcga gcttttggag 1020
tacgtcgtct ttaggttggg gggaggggtt ttatgcgatg gagtttcccc acactgagtg 1080
ggtggagact gaagttaggc cagcttggca cttgatgtaa ttctccttgg aatttgccct 1140
ttttgagttt ggatcttggt tcattctcaa gcctcagaca gtggttcaaa gtttttttct 1200

-continued

```
tccatttcag gtgtcgtgac catgagcttc gaattcgcca ccatgctgtc tagcatggct   1260
gccgctggat ctgtgaaagc tgctctgcag gttgccgagg tgctggaagc catcgtgtct   1320
tgttgtgtgg gacctgaggg cagacaggtg ctgtgtacaa agcctacagg cgaagtgctg   1380
ctgagcagaa atggcggcag actgctcgaa gccctgcacc tggaacaccc tatcgccaga   1440
atgatcgtgg actgcgtgtc cagccacctg aagaaaacag gcgacggcgc caagaccttc   1500
atcatctttc tgtgccatct gctgcggggc ctgcacgcca tcaccgatag agaaaaggac   1560
cctctgatgt gcgagaacat ccagacacac ggccggcact ggaagaactg ctcccggtgg   1620
aagtttatca gccaggctct gctgaccttt cagacccaga tcctggacgg catcatggac   1680
cagtacctga gcagacactt cctgagcatc ttcagcagcg ccaaagaacg gaccctgtgc   1740
agaagctctc tggaactgct gctcgaggcc tacttttgcg gcagagtggg cagaaacaac   1800
cacaagttca tctcccagct gatgtgtgac tacttcttca agtgcatgac ctgcaagagc   1860
ggcatcggcg tgttcgagct ggtggacgat cacttcgtgg aactgaatgt gggcgtgacc   1920
ggcctgcctg tgtccgatag cagaattatt gccggcctgg tgctgcagaa agacttcagc   1980
gtgtacagac ccgccgacgg cgacatgaga atggtcatcg tgaccgagac aatccagcct   2040
ctgttcagca caagcggcag cgagttcatc ctgaacagcg aggcccagtt tcagaccagc   2100
cagttctgga tcatggaaaa gaccaaggcc atcatgaagc acctccacag ccagaacgtg   2160
aagctgctga tctccagcgt gaagcagccc gacctggtgt cttattatgc cggcgtgaac   2220
ggcatcagcg tggtggaatg tctgagcagc gaagaggtgt ccctgatcag acggatcatc   2280
ggactgagcc cctttgtgcc tcctcaagcc tttagccagt gcgagatccc taacacagcc   2340
ctggtcaagt tctgcaagcc cctgatcctg cggagcaaga gatatgtgca cctgggcctg   2400
atcagcacat gcgccttcat tcctcactcc atcgtgctgt gtggacctgt gcacggactg   2460
attgagcagc acgaagatgc actgcacggc gccctgaaaa tgctgagaca gctgttcaag   2520
gacctggacc tgaactacat gacccagacc aacgaccaga acggcaccag cagcctgttc   2580
atctacaaga acagcggcga gagctatcag gccccagatc caggcaatgg cagcatccag   2640
aggccttacc aggataccgt ggccgagaac aaggacgccc tggaaaaaac ccagacctac   2700
ctgaaggtgc acagcaacct ggtcatcccc gatgtggaac tggaaaccta cattccctac   2760
agcaccccta cactgacccc taccgatacc ttccagaccg tggaaaccct gacctgtctg   2820
agcctggaac ggaacagact gaccgactac tacgagcccc tgctgaaaaa caacagcacc   2880
gcctatagca cccggggcaa cagaatcgag atcagctacg agaacctgca agtgaccaac   2940
atcacccgga agggctccat gctgccagtg tcctgcaagc tgcctaatat gggcaccagc   3000
cagagctacc tgtcctcttc tatgcctgcc ggatgtgtgc tgcctgtcgg cggcaatttt   3060
gagatcctgc tgcactacta cctgctgaac tacgccaaga agtgccacca gagcgaagag   3120
acaatggtgt ccatgattat cgccaacgct ctgctgggca tccccaaggt gctgtacaag   3180
agcaagaccg gcaagtacag cttccctcac acctacatta gagccgtgca cgccctgcag   3240
accaatcagc cactggtttc tagccagaca ggcctggaaa gcgtgatggg aaagtaccag   3300
ctgctgacca gcgtgctgca gtgcctgacc aagatcctga ccatcgacat ggtcatcacc   3360
gtgaagcggc accctcagaa agtgcacaac caggacagcg aggacgagct gtaggcgccg   3420
tcgac                                                               3425
```

<210> SEQ ID NO 32

<211> LENGTH: 3428
<212> TYPE: DNA
<213> ORGANISM: Artificial sequence
<220> FEATURE:
<223> OTHER INFORMATION: Construct comprising EFS promoter and COSEQ2-
      BBS10 nucleotide sequence (referred to as EFS-COSEQ2-BBS10)

<400> SEQUENCE: 32

```
actagtgggc agatctcgat cgagttgggc cccagagctt ggctccggtg cccgtcagtg     60

ggcagagcgc acatcgccca cagtccccga gaagttgtgg ggaggggtcg gcaattgaac    120

cggtgcctag agaaggtggc gcggggtaaa ctgggaaagt gatgtcgtgt actggctccg    180

cctttttccc gagggtgggg gagaaccgta tataagtgca gtagtcgccg tgaacgttct    240

ttttcgcaac gggtttgccg ccagaacaca ggtaagtgcc gtgtgtggtt cccgcgggcc    300

tggcctcttt acgggttatg gcccttgcgt gccttgaatt acttccacct ggctgcagta    360

cgtgattctt gatcccgagc ttcgggttgg aagtgggtgg gagagttcga ggccttgcgc    420

ttaaggagcc ccttcgcctc gtgcttgagt tgaggcctgg cctgggcgct ggggccgccg    480

cgtgcgaatc tggtggcacc ttcgcgcctg tctcgctgct ttcgataagt ctctagccat    540

ttaaaatttt tgatgacctg ctgcgacgct ttttttctgg caagatagtc ttgtaaatgc    600

gggccaagat ctgcacactg gtatttcggt ttttggggcc gcgggcggcg acggggcccg    660

tgcgtcccag cgcacatgtt cggcgaggcg gggcctgcga gcgcggccac cgagaatcgg    720

acgggggtag tctcaagctg gccggcctgc tctggtgcct ggcctcgcgc cgccgtgtat    780

cgccccgccc tgggcggcaa ggctggcccg gtcggcacca gttgcgtgag cggaaagatg    840

gccgcttccc ggccctgctg cagggagctc aaaatggagg acgcggcgct cgggagagcg    900

ggcgggtgag tcacccacac aaaggaaaag ggcctttccg tcctcagccg tcgcttcatg    960

tgactccacg gagtaccggg cgccgtccag gcacctcgat tagttctcga gcttttggag   1020

tacgtcgtct ttaggttggg gggaggggtt ttatgcgatg gagtttcccc acactgagtg   1080

ggtggagact gaagttaggc cagcttggca cttgatgtaa ttctccttgg aatttgccct   1140

ttttgagttt ggatcttggt tcattctcaa gcctcagaca gtggttcaaa gtttttttct   1200

tccatttcag gtgtcgtgac catgagcttc gaattcgcca ccatgctgag ctccatggct   1260

gccgccggat ctgtgaaagc cgccctgcag gtggcagagg tgctggaggc aatcgtgagc   1320

tgttgcgtgg gacctgaggg ccggcaggtg ctgtgcacaa agccaaccgg cgaggtgctg   1380

ctgtctagaa atggcggccg gctgctggag gccctgcacc tggagcaccc aattgcaaga   1440

atgatcgtgg actgcgtgtc tagccacctg aagaagacag gcgatggcgc caagaccttc   1500

atcatcttcc tgtgccacct gctgaggggc ctgcacgcca tcacagaccg cgagaaggat   1560

cctctgatgt gcgagaacat ccagacccac ggcaggcact ggaagaattg ttcccgctgg   1620

aagttcatct ctcaggccct gctgacattt cagacccaga tcctggacgg catcatggat   1680

cagtatctga gcaggcactt cctgtccatc ttttcctctg ccaaggagcg gaccctgtgc   1740

agaagctccc tggagctgct gctggaggcc tacttctgtg gccgggtggg cagaaacaat   1800

cacaagttta tcagccagct gatgtgcgac tatttcttta agtgcatgac ctgtaagtcc   1860

ggcatcggcg tgttcgagct ggtggacgat cactttgtgg agctgaacgt gggagtgaca   1920

ggcctgcccg tgtccgactc tcgcatcatc gccggcctgg tgctgcagaa ggatttctcc   1980

gtgtaccggc ctgccgacgg cgatatgaga atggtcatcg tgaccgagac aatccagcca   2040

ctgttcagca cctccggctc tgagttcatc ctgaacagcg aggcccagtt ccagacatct   2100
```

-continued

```
cagttttgga tcatggagaa gaccaaggcc atcatgaagc acctgcacag ccagaacgtg   2160

aagctgctga tctctagcgt gaagcagcca gacctggtgt cttactatgc cggcgtgaat   2220

ggcatcagcg tggtggagtg tctgtcctct gaggaggtgt ccctgatccg gagaatcatt   2280

ggcctgtctc ccttcgtgcc ccctcaggcc tttagccagt gcgagatccc caacacagcc   2340

ctggtgaagt tctgtaagcc tctgatcctg aggtccaagc ggtacgtgca cctgggcctg   2400

atcagcacct gcgcctttat cccacactct atcgtgctgt gcggacctgt gcacggcctg   2460

attgagcagc acgaggatgc actgcacggc gccctgaaga tgctgaggca gctgttcaag   2520

gacctggatc tgaattacat gacccagaca aacgaccaga atggcacaag ctccctgttt   2580

atctacaaga actctggcga gagctatcag gccccagatc ccggcaatgg cagcattcag   2640

cgcccctacc aggacacagt ggcagagaac aaggatgccc tggagaagac ccagacatat   2700

ctgaaggtgc actccaacct ggtcatccct gacgtggagc tggagacata catcccttat   2760

tctaccccaa cactgacccc cacagatacc ttccagacag tggagacact gacctgcctg   2820

tccctggaga ggaaccgcct gaccgactac tatgagcccc tgctgaagaa caattccaca   2880

gcctactcta cccggggcaa tagaatcgag atcagctatg agaacctgca ggtgacaaat   2940

atcaccagaa agggctctat gctgcctgtg agctgcaagc tgccaaacat gggcaccagc   3000

cagtcctacc tgtctagctc catgcctgca ggatgcgtgc tgcctgtggg cggcaacttc   3060

gagatcctgc tgcactacta tctgctgaat tatgccaaga agtgccacca gagcgaggag   3120

acaatggtgt ccatgatcat cgccaacgcc ctgctgggca tcccaaaggt gctgtacaag   3180

tctaagaccg gcaagtacag ctttccccac acctatatcc gggccgtgca cgccctgcag   3240

acaaatcagc ctctggtgtc tagccagacc ggcctggagt ccgtgatggg caagtaccag   3300

ctgctgacat ctgtgctgca gtgtctgaca aagatcctga ccatcgatat ggtcatcacc   3360

gtgaagagac acccacagaa ggtgcacaat caggacagcg aggatgagct gtaagcggcc   3420

gcgtcgac                                                            3428
```

<210> SEQ ID NO 33
<211> LENGTH: 3470
<212> TYPE: DNA
<213> ORGANISM: Artificial sequence
<220> FEATURE:
<223> OTHER INFORMATION: Construct comprising UBC promoter and wild type BBS10 nucleotide sequence (referred to as UBC-WTBBS10)

<400> SEQUENCE: 33

```
actagtaacc cgtgtcggct ccagatctgg cctccgcgcc gggttttggc gcctcccgcg     60

ggcgcccccc tcctcacggc gagcgctgcc acgtcagacg aagggcgcag cgagcgtcct    120

gatccttccg cccggacgct caggacagcg gcccgctgct cataagactc ggccttagaa    180

ccccagtatc agcagaagga cattttagga cgggacttgg gtgactctag ggcactggtt    240

ttctttccag agagcggaac aggcgaggaa aagtagtccc ttctcggcga ttctgcggag    300

ggatctccgt ggggcggtga acgccgatga ttatataagg acgcgccggg tgtggcacag    360

ctagttccgt cgcagccggg atttgggtcg cggttcttgt ttgtggatcg ctgtgatcgt    420

cacttggtga gtagcgggct gctgggctgg ccggggcttt cgtggccgcc gggccgctcg    480

gtgggacgga agcgtgtgga gagaccgcca agggctgtag tctgggtccg cgagcaaggt    540

tgccctgaac tgggggttgg ggggagcgca gcaaaatggc ggctgttccc gagtcttgaa    600

tggaagacgc ttgtgaggcg ggctgtgagg tcgttgaaac aaggtggggg gcatggtggg    660
```

-continued

```
cggcaagaac ccaaggtctt gaggccttcg ctaatgcggg aaagctctta ttcgggtgag    720
atgggctggg gcaccatctg gggaccctga cgtgaagttt gtcactgact ggagaactcg    780
gtttgtcgtc tgttgcgggg gcggcagtta tggcggtgcc gttgggcagt gcacccgtac    840
ctttgggagc gcgcgccctc gtcgtgtcgt gacgtcaccc gttctgttgg cttataatgc    900
agggtggggc cacctgccgg taggtgtgcg gtaggctttt ctccgtcgca ggacgcaggg    960
ttcgggccta gggtaggctc tcctgaatcg acaggcgccg gacctctggt gaggggaggg   1020
ataagtgagg cgtcagtttc tttggtcggt tttatgtacc tatcttctta agtagctgaa   1080
gctccggttt tgaactatgc gctcggggtt ggcgagtgtg ttttgtgaag tttttttaggc   1140
accttttgaa atgtaatcat ttgggtcaat atgtaatttt cagtgttaga ctagtaaatt   1200
gtccgctaaa ttctggccgt ttttggcttt tttgttagac gaagcttggg ctgcaggtcg   1260
agctcaagct tcgaattcgc caccatgtta agttctatgg ccgctgcagg gtctgtgaag   1320
gcggcgttgc aggtggccga ggtgctggaa gccatcgtga gctgctgcgt ggggcccgag   1380
ggacggcaag ttttgtgtac gaagcccact ggcgaggtgc ttctcagccg gaatggaggc   1440
cgcctcctgg aggcgctaca cttagagcat cccatagcca ggatgatagt ggactgtgtt   1500
tccagtcatc tcaaaaaaac aggagatggt gcaaaaacat ttattatctt tctttgccat   1560
ttgcttagag gacttcatgc aatcacagac agagaaaagg atcctttgat gtgtgaaaac   1620
attcaaaccc atggaaggca ttggaaaaat tgttctcggt ggaaatttat ttcccaggct   1680
ctcctaacgt ttcagacaca aatattagac ggtattatgg accagtacct aagtagacac   1740
tttttgtcta tcttttcgtc tgctaaagag agaacattgt gtaggagctc tttagagttg   1800
ctcttagaag catacttttg tggaagagtg ggaagaaata atcataaatt tatttcacag   1860
ttgatgtgtg actacttttt caagtgtatg acttgtaaaa gtgggattgg tgtatttgag   1920
ttagtggatg accattttgt agagttgaat gttggtgtca ctggccttcc tgtttcagat   1980
tccaggatca tagctggtct tgtgcttcag aaagattttt ctgtgtaccg cccagcagat   2040
ggtgacatgc gaatggtgat agtaacagaa accattcagc ctctttttc cacttctgga    2100
tcagagttta ttctaaattc agaagcacag tttcagacat ctcaattttg gattatggaa   2160
aagacaaaag caataatgaa acatctacat agtcagaatg taaaattgct catatctagt   2220
gtgaaacaac cagatttagt tagttattat gcaggggtga atggcatatc agtggttgag   2280
tgtttatcat cagaagaagt ttctcttatc cggaggatca ttggtctttc tccatttgta   2340
ccaccacagg cctttttcgca gtgtgaaata cctaacactg ctttggtgaa attttgtaaa  2400
cctcttatcc ttagatccaa aagatatgtt catctaggct tgataagcac atgtgcattt   2460
ataccacact ctatagttct ttgtggacca gtgcatggtc tcattgaaca acatgaggat   2520
gctttacatg gagcacttaa aatgcttcgg caattattta aagaccttga tctaaattac   2580
atgacacaaa ccaatgacca aaatggcact tcaagtcttt ttatttataa gaacagtgga   2640
gaaagttatc aagcaccaga tcctggtaat ggctcaatac aaaggcctta tcaggacaca   2700
gttgcagaga acaaagatgc attggaaaaa actcaaacat atttaaaagt acattctaat   2760
ttggtaattc cagatgtaga attagaaaca tatattccgt attcaacccc cacactgaca   2820
ccaacagata cattccaaac agttgaaacg ctgacatgtt tgtctttgga aagaaacagg   2880
ctaactgatt attatgaacc attactcaag aacaattcca ctgcttattc aacaagggga   2940
aatagaatag aaatttctta cgaaaattta caggtcacaa atattactag aaagggaagc   3000
atgttaccag tgagctgtaa gttaccgaat atgggtactt cccagagtta cctttcctca   3060
```

tctatgccag ctggttgtgt tttgccagta ggtggtaatt ttgagatctt gttacattac 3120
tatcttctca attatgccaa aaaatgccat caatcagaag aaaccatggt tagtatgata 3180
atagctaatg cacttttagg cattcccaaa gtcctttata aatctaaaac aggaaagtac 3240
agctttccac atacatatat aagagctgtc catgcactgc aaaccaatca acccttggta 3300
agcagtcaga caggtttgga atcagtaatg ggtaaatacc agctactaac ttcagttctt 3360
cagtgtttga caaaaatatt aaccattgac atggtaatca ctgttaagag acaccctcag 3420
aaagttcaca atcaagattc agaagatgaa ctataagcgg ccgcgtcgac 3470

<210> SEQ ID NO 34
<211> LENGTH: 3467
<212> TYPE: DNA
<213> ORGANISM: Artificial sequence
<220> FEATURE:
<223> OTHER INFORMATION: Construct comprising UBC promoter and COSEQ1-BBS10 nucleotide sequence (referred to as UBC-COSEQ1BBS10)

<400> SEQUENCE: 34
actagtaacc cgtgtcggct ccagatctgg cctccgcgcc gggttttggc gcctcccgcg 60
ggcgcccccc tcctcacggc gagcgctgcc acgtcagacg aagggcgcag cgagcgtcct 120
gatccttccg cccggacgct caggacagcg gcccgctgct cataagactc ggccttagaa 180
ccccagtatc agcagaagga cattttagga cgggacttgg gtgactctag ggcactggtt 240
ttctttccag agagcggaac aggcgaggaa aagtagtccc ttctcggcga ttctgcggag 300
ggatctccgt ggggcggtga acgccgatga ttatataagg acgcgccggg tgtggcacag 360
ctagttccgt cgcagccggg atttgggtcg cggttcttgt ttgtggatcg ctgtgatcgt 420
cacttggtga gtagcgggct gctgggctgg ccggggcttt cgtggccgcc gggccgctcg 480
gtgggacgga agcgtgtgga gagaccgcca agggctgtag tctgggtccg cgagcaaggt 540
tgccctgaac tgggggttgg ggggagcgca gcaaaatggc ggctgttccc gagtcttgaa 600
tggaagacgc ttgtgaggcg ggctgtgagg tcgttgaaac aaggtggggg gcatggtggg 660
cggcaagaac ccaaggtctt gaggccttcg ctaatgcggg aaagctctta ttcgggtgag 720
atgggctggg gcaccatctg ggaccctga cgtgaagttt gtcactgact ggagaactcg 780
gtttgtcgtc tgttgcgggg gcggcagtta tggcggtgcc gttgggcagt gcacccgtac 840
ctttgggagc gcgcgccctc gtcgtgtcgt gacgtcaccc gttctgttgg cttataatgc 900
agggtggggc cacctgccgg taggtgtgcg gtaggctttt ctccgtcgca ggacgcaggg 960
ttcgggccta gggtaggctc tcctgaatcg acaggcgccg gacctctggt gaggggaggg 1020
ataagtgagg cgtcagtttc tttggtcggt tttatgtacc tatcttctta agtagctgaa 1080
gctccggttt tgaactatgc gctcggggtt ggcgagtgtg ttttgtgaag ttttttaggc 1140
accttttgaa atgtaatcat ttgggtcaat atgtaatttt cagtgttaga ctagtaaatt 1200
gtccgctaaa ttctggccgt ttttggcttt tttgttagac gaagcttggg ctgcaggtcg 1260
agctcaagct tcgaattcgc caccatgctg tctagcatgg ctgccgctgg atctgtgaaa 1320
gctgctctgc aggttgccga ggtgctggaa gccatcgtgt cttgttgtgt gggacctgag 1380
ggcagacagg tgctgtgtac aaagcctaca ggcgaagtgc tgctgagcag aaatggcggc 1440
agactgctcg aagccctgca cctggaacac cctatcgcca gaatgatcgt ggactgcgtg 1500
tccagccacc tgaagaaaac aggcgacggc gccaagacct tcatcatctt tctgtgccat 1560
ctgctgcggg gcctgcacgc catcaccgat agagaaaagg accctctgat gtgcgagaac 1620

```
atccagacac acggccggca ctggaagaac tgctcccggt ggaagtttat cagccaggct   1680

ctgctgacct ttcagaccca gatcctggac ggcatcatgg accagtacct gagcagacac   1740

ttcctgagca tcttcagcag cgccaaagaa cggaccctgt gcagaagctc tctggaactg   1800

ctgctcgagg cctacttttg cggcagagtg ggcagaaaca accacaagtt catctcccag   1860

ctgatgtgtg actacttctt caagtgcatg acctgcaaga gcggcatcgg cgtgttcgag   1920

ctggtggacg atcacttcgt ggaactgaat gtgggcgtga ccggcctgcc tgtgtccgat   1980

agcagaatta ttgccggcct ggtgctgcag aaagacttca gcgtgtacag acccgccgac   2040

ggcgacatga gaatggtcat cgtgaccgag acaatccagc ctctgttcag cacaagcggc   2100

agcgagttca tcctgaacag cgaggcccag tttcagacca gccagttctg gatcatggaa   2160

aagaccaagg ccatcatgaa gcacctccac agccagaacg tgaagctgct gatctccagc   2220

gtgaagcagc ccgacctggt gtcttattat gccggcgtga acggcatcag cgtggtggaa   2280

tgtctgagca gcgaagaggt gtccctgatc agacggatca tcggactgag cccctttgtg   2340

cctcctcaag cctttagcca gtgcgagatc cctaacacag ccctggtcaa gttctgcaag   2400

cccctgatcc tgcggagcaa gagatatgtg cacctgggcc tgatcagcac atgcgccttc   2460

attcctcact ccatcgtgct gtgtggacct gtgcacggac tgattgagca gcacgaagat   2520

gcactgcacg gcgccctgaa aatgctgaga cagctgttca aggacctgga cctgaactac   2580

atgacccaga ccaacgacca gaacggcacc agcagcctgt tcatctacaa gaacagcggc   2640

gagagctatc aggccccaga tccaggcaat ggcagcatcc agaggcctta ccaggatacc   2700

gtggccgaga acaaggacgc cctggaaaaa acccagacct acctgaaggt gcacagcaac   2760

ctggtcatcc ccgatgtgga actggaaacc tacattccct acagcacccc tacactgacc   2820

cctaccgata ccttccagac cgtggaaacc ctgacctgtc tgagcctgga acggaacaga   2880

ctgaccgact actacgagcc cctgctgaaa aacaacagca ccgcctatag cacccggggc   2940

aacagaatcg agatcagcta cgagaacctg caagtgacca acatcacccg gaagggctcc   3000

atgctgccag tgtcctgcaa gctgcctaat atgggcacca gccagagcta cctgtcctct   3060

tctatgcctg ccggatgtgt gctgcctgtc ggcggcaatt ttgagatcct gctgcactac   3120

tacctgctga actacgccaa gaagtgccac cagagcgaag agacaatggt gtccatgatt   3180

atcgccaacg ctctgctggg catccccaag gtgctgtaca agagcaagac cggcaagtac   3240

agcttccctc acacctacat tagagccgtg cacgccctgc agaccaatca gccactggtt   3300

tctagccaga caggcctgga aagcgtgatg ggaaagtacc agctgctgac cagcgtgctg   3360

cagtgcctga ccaagatcct gaccatcgac atggtcatca ccgtgaagcg gcaccctcag   3420

aaagtgcaca accaggacag cgaggacgag ctgtaggcgc cgtcgac               3467
```

<210> SEQ ID NO 35
<211> LENGTH: 3470
<212> TYPE: DNA
<213> ORGANISM: Artificial sequence
<220> FEATURE:
<223> OTHER INFORMATION: Construct comprising UBC promoter and COSEQ2-BBS10 nucleotide sequence (referred to as UBC-COSEQ2-BBS10)

<400> SEQUENCE: 35

```
actagtaacc cgtgtcggct ccagatctgg cctccgcgcc gggttttggc gcctcccgcg     60

ggcgcccccc tcctcacggc gagcgctgcc acgtcagacg aagggcgcag cgagcgtcct    120

gatccttccg cccggacgct caggacagcg gcccgctgct cataagactc ggccttagaa    180
```

```
ccccagtatc agcagaagga cattttagga cgggacttgg gtgactctag ggcactggtt    240
ttctttccag agagcggaac aggcgaggaa aagtagtccc ttctcggcga ttctgcggag    300
ggatctccgt ggggcggtga acgccgatga ttatataagg acgcgccggg tgtggcacag    360
ctagttccgt cgcagccggg atttgggtcg cggttcttgt ttgtggatcg ctgtgatcgt    420
cacttggtga gtagcgggct gctgggctgg ccggggcttt cgtggccgcc gggccgctcg    480
gtgggacgga agcgtgtgga gagaccgcca agggctgtag tctgggtccg cgagcaaggt    540
tgccctgaac tgggggttgg ggggagcgca gcaaaatggc ggctgttccc gagtcttgaa    600
tggaagacgc ttgtgaggcg ggctgtgagg tcgttgaaac aaggtggggg gcatggtggg    660
cggcaagaac ccaaggtctt gaggccttcg ctaatgcggg aaagctctta ttcgggtgag    720
atgggctggg gcaccatctg ggaccctga cgtgaagttt gtcactgact ggagaactcg    780
gtttgtcgtc tgttgcgggg gcggcagtta tggcggtgcc gttgggcagt gcacccgtac    840
ctttgggagc gcgcgccctc gtcgtgtcgt gacgtcaccc gttctgttgg cttataatgc    900
agggtggggc cacctgccgg taggtgtgcg gtaggctttt ctccgtcgca ggacgcaggg    960
ttcgggccta gggtaggctc tcctgaatcg acaggcgccg gacctctggt gaggggaggg   1020
ataagtgagg cgtcagtttc tttggtcggt tttatgtacc tatcttctta agtagctgaa   1080
gctccggttt tgaactatgc gctcggggtt ggcgagtgtg ttttgtgaag ttttttaggc   1140
accttttgaa atgtaatcat ttgggtcaat atgtaatttt cagtgttaga ctagtaaatt   1200
gtccgctaaa ttctggccgt ttttggcttt tttgttagac gaagcttggg ctgcaggtcg   1260
agctcaagct tcgaattcgc caccatgctg agctccatgg ctgccgccgg atctgtgaaa   1320
gccgccctgc aggtggcaga ggtgctggag gcaatcgtga gctgttgcgt gggacctgag   1380
ggccggcagg tgctgtgcac aaagccaacc ggcgaggtgc tgctgtctag aaatggcggc   1440
cggctgctgg aggccctgca cctggagcac ccaattgcaa gaatgatcgt ggactgcgtg   1500
tctagccacc tgaagaagac aggcgatggc gccaagacct tcatcatctt cctgtgccac   1560
ctgctgaggg gcctgcacgc catcacagac cgcgagaagg atcctctgat gtgcgagaac   1620
atccagaccc acggcaggca ctggaagaat tgttcccgct ggaagttcat ctctcaggcc   1680
ctgctgacat ttcagaccca gatcctggac ggcatcatgg atcagtatct gagcaggcac   1740
ttcctgtcca tcttttcctc tgccaaggag cggaccctgt gcagaagctc cctggagctg   1800
ctgctggagg cctacttctg tggccgggtg ggcagaaaca atcacaagtt tatcagccag   1860
ctgatgtgcg actatttctt taagtgcatg acctgtaagt ccggcatcgg cgtgttcgag   1920
ctggtggacg atcactttgt ggagctgaac gtgggagtga caggcctgcc cgtgtccgac   1980
tctcgcatca tcgccggcct ggtgctgcag aaggatttct ccgtgtaccg gcctgccgac   2040
ggcgatatga gaatggtcat cgtgaccgag acaatccagc cactgttcag cacctccggc   2100
tctgagttca tcctgaacag cgaggcccag ttccagacat ctcagttttg gatcatggag   2160
aagaccaagg ccatcatgaa gcacctgcac agccagaacg tgaagctgct gatctctagc   2220
gtgaagcagc cagacctggt gtcttactat gccggcgtga atggcatcag cgtggtggag   2280
tgtctgtcct ctgaggaggt gtccctgatc cggagaatca ttggcctgtc tcccttcgtg   2340
ccccctcagg cctttagcca gtgcgagatc cccaacacag ccctggtgaa gttctgtaag   2400
cctctgatcc tgaggtccaa gcggtacgtg cacctgggcc tgatcagcac ctgcgccttt   2460
atcccacact ctatcgtgct gtgcggacct gtgcacggcc tgattgagca gcacgaggat   2520
```

-continued

```
gcactgcacg gcgccctgaa gatgctgagg cagctgttca aggacctgga tctgaattac   2580

atgacccaga caaacgacca gaatggcaca agctccctgt ttatctacaa gaactctggc   2640

gagagctatc aggccccaga tcccggcaat ggcagcattc agcgccccta ccaggacaca   2700

gtggcagaga acaaggatgc cctggagaag acccagacat atctgaaggt gcactccaac   2760

ctggtcatcc ctgacgtgga gctggagaca tacatccctt attctacccc aacactgacc   2820

cccacagata ccttccagac agtggagaca ctgacctgcc tgtccctgga gaggaaccgc   2880

ctgaccgact actatgagcc cctgctgaag aacaattcca cagcctactc tacccggggc   2940

aatagaatcg agatcagcta tgagaacctg caggtgacaa atatcaccag aaagggctct   3000

atgctgcctg tgagctgcaa gctgccaaac atgggcacca gccagtccta cctgtctagc   3060

tccatgcctg caggatgcgt gctgcctgtg ggcggcaact tcgagatcct gctgcactac   3120

tatctgctga attatgccaa gaagtgccac cagagcgagg agacaatggt gtccatgatc   3180

atcgccaacg ccctgctggg catcccaaag gtgctgtaca agtctaagac cggcaagtac   3240

agctttcccc acacctatat ccgggccgtg cacgccctgc agacaaatca gcctctggtg   3300

tctagccaga ccggcctgga gtccgtgatg ggcaagtacc agctgctgac atctgtgctg   3360

cagtgtctga caaagatcct gaccatcgat atggtcatca ccgtgaagag acacccacag   3420

aaggtgcaca atcaggacag cgaggatgag ctgtaagcgg ccgcgtcgac              3470
```

```
<210> SEQ ID NO 36
<211> LENGTH: 2815
<212> TYPE: DNA
<213> ORGANISM: Artificial sequence
<220> FEATURE:
<223> OTHER INFORMATION: Construct comprising CMV promoter and wild type
      BBS10 nucleotide sequence (referred to as CMV-WTBBS10)

<400> SEQUENCE: 36

actagttatt aatagtaatc aattacgggg tcattagttc atagcccata tatggagttc     60

cgcgttacat aacttacggt aaatggcccg cctggctgac cgcccaacga cccccgccca    120

ttgacgtcaa taatgacgta tgttcccata gtaacgccaa tagggacttt ccattgacgt    180

caatgggtgg agtatttacg gtaaactgcc cacttggcag tacatcaagt gtatcatatg    240

ccaagtacgc cccctattga cgtcaatgac ggtaaatggc ccgcctggca ttatgcccag    300

tacatgacct tatgggactt tcctacttgg cagtacatct acgtattagt catcgctatt    360

accatggtga tgcggttttg gcagtacatc aatgggcgtg gatagcggtt tgactcacgg    420

ggatttccaa gtctccaccc cattgacgtc aatgggagtt tgttttggca ccaaaatcaa    480

cgggactttc caaaatgtcg taacaactcc gccccattga cgcaaatggg cggtaggcgt    540

gtacggtggg aggtctatat aagcagagct ggtttagtga accgtcagat ccgctagcgc    600

taccggactc agatctcgaa ttcgccacca tgttaagttc tatggccgct gcagggtctg    660

tgaaggcggc gttgcaggtg gccgaggtgc tggaagccat cgtgagctgc tgcgtggggc    720

ccgagggacg gcaagttttg tgtacgaagc ccactggcga ggtgcttctc agccggaatg    780

gaggccgcct cctggaggcg ctacacttag agcatcccat agccaggatg atagtggact    840

gtgtttccag tcatctcaaa aaaacaggag atggtgcaaa aacatttatt atctttcttt    900

gccatttgct tagaggactt catgcaatca cagacagaga aaaggatcct ttgatgtgtg    960

aaaacattca aacccatgga aggcattgga aaaattgttc tcggtggaaa tttatttccc   1020

aggctctcct aacgtttcag acacaaatat tagacggtat tatggaccag tacctaagta   1080
```

-continued gacacttttt gtctatcttt tcgtctgcta aagagagaac attgtgtagg agctctttag 1140
agttgctctt agaagcatac ttttgtggaa gagtgggaag aaataatcat aaatttattt 1200
cacagttgat gtgtgactac tttttcaagt gtatgacttg taaaagtggg attggtgtat 1260
ttgagttagt ggatgaccat tttgtagagt tgaatgttgg tgtcactggc cttcctgttt 1320
cagattccag gatcatagct ggtcttgtgc ttcagaaaga tttttctgtg taccgcccag 1380
cagatggtga catgcgaatg gtgatagtaa cagaaaccat tcagcctctt ttttccactt 1440
ctggatcaga gtttattcta aattcagaag cacagtttca gacatctcaa ttttggatta 1500
tggaaaagac aaaagcaata atgaaacatc tacatagtca gaatgtaaaa ttgctcatat 1560
ctagtgtgaa acaaccagat ttagttagtt attatgcagg ggtgaatggc atatcagtgg 1620
ttgagtgttt atcatcagaa gaagtttctc ttatccggag gatcattggt ctttctccat 1680
ttgtaccacc acaggccttt tcgcagtgtg aaatacctaa cactgctttg gtgaaatttt 1740
gtaaacctct tatccttaga tccaaaagat atgttcatct aggcttgata agcacatgtg 1800
catttatacc acactctata gttctttgtg gaccagtgca tggtctcatt gaacaacatg 1860
aggatgcttt acatggagca cttaaaatgc ttcggcaatt atttaaagac cttgatctaa 1920
attacatgac acaaaccaat gaccaaaatg gcacttcaag tctttttatt tataagaaca 1980
gtggagaaag ttatcaagca ccagatcctg gtaatggctc aatacaaagg ccttatcagg 2040
acacagttgc agagaacaaa gatgcattgg aaaaaactca aacatattta aaagtacatt 2100
ctaatttggt aattccagat gtagaattag aaacatatat tccgtattca acccccacac 2160
tgacaccaac agatacattc caaacagttg aaacgctgac atgtttgtct ttggaaagaa 2220
acaggctaac tgattattat gaaccattac tcaagaacaa ttccactgct tattcaacaa 2280
ggggaaatag aatagaaatt tcttacgaaa atttacaggt cacaaatatt actagaaagg 2340
gaagcatgtt accagtgagc tgtaagttac cgaatatggg tacttcccag agttaccttt 2400
cctcatctat gccagctggt tgtgttttgc cagtaggtgg taattttgag atcttgttac 2460
attactatct tctcaattat gccaaaaaat gccatcaatc agaagaaacc atggttagta 2520
tgataatagc taatgcactt ttaggcattc ccaaagtcct ttataaatct aaaacaggaa 2580
agtacagctt tccacataca tatataagag ctgtccatgc actgcaaacc aatcaaccct 2640
tggtaagcag tcagacaggt ttggaatcag taatgggtaa ataccagcta ctaacttcag 2700
ttcttcagtg tttgacaaaa atattaacca ttgacatggt aatcactgtt aagagacacc 2760
ctcagaaagt tcacaatcaa gattcagaag atgaactata agcggccgcg tcgac 2815

<210> SEQ ID NO 37
<211> LENGTH: 2812
<212> TYPE: DNA
<213> ORGANISM: Artificial sequence
<220> FEATURE:
<223> OTHER INFORMATION: Construct comprising CMV promoter and COSEQ1-
BBS10 nucleotide sequence (referred to as CMV-COSEQ1-BBS10)

<400> SEQUENCE: 37
actagttatt aatagtaatc aattacgggg tcattagttc atagcccata tatggagttc 60
cgcgttacat aacttacggt aaatggcccg cctggctgac cgcccaacga cccccgccca 120
ttgacgtcaa taatgacgta tgttcccata gtaacgccaa tagggacttt ccattgacgt 180
caatgggtgg agtatttacg gtaaactgcc cacttggcag tacatcaagt gtatcatatg 240
ccaagtacgc cccctattga cgtcaatgac ggtaaatggc ccgcctggca ttatgcccag 300

-continued

```
tacatgacct tatgggactt tcctacttgg cagtacatct acgtattagt catcgctatt    360
accatggtga tgcggttttg gcagtacatc aatgggcgtg gatagcggtt tgactcacgg    420
ggatttccaa gtctccaccc cattgacgtc aatgggagtt tgttttggca ccaaaatcaa    480
cgggactttc caaaatgtcg taacaactcc gccccattga cgcaaatggg cggtaggcgt    540
gtacggtggg aggtctatat aagcagagct ggtttagtga accgtcagat ccgctagcgc    600
taccggactc agatctcgaa ttcgccacca tgctgtctag catggctgcc gctggatctg    660
tgaaagctgc tctgcaggtt gccgaggtgc tggaagccat cgtgtcttgt tgtgtgggac    720
ctgagggcag acaggtgctg tgtacaaagc ctacaggcga agtgctgctg agcagaaatg    780
gcggcagact gctcgaagcc ctgcacctgg aacaccctat cgccagaatg atcgtggact    840
gcgtgtccag ccacctgaag aaaacaggcg acggcgccaa gaccttcatc atctttctgt    900
gccatctgct gcggggcctg cacgccatca ccgatagaga aaaggaccct ctgatgtgcg    960
agaacatcca gacacacggc cggcactgga agaactgctc ccggtggaag tttatcagcc   1020
aggctctgct gacctttcag acccagatcc tggacggcat catggaccag tacctgagca   1080
gacacttcct gagcatcttc agcagcgcca aagaacggac cctgtgcaga agctctctgg   1140
aactgctgct cgaggcctac ttttgcggca gagtgggcag aaacaaccac aagttcatct   1200
cccagctgat gtgtgactac ttcttcaagt gcatgacctg caagagcggc atcggcgtgt   1260
tcgagctggt ggacgatcac ttcgtggaac tgaatgtggg cgtgaccggc ctgcctgtgt   1320
ccgatagcag aattattgcc ggcctggtgc tgcagaaaga cttcagcgtg tacagacccg   1380
ccgacggcga catgagaatg gtcatcgtga ccgagacaat ccagcctctg ttcagcacaa   1440
gcggcagcga gttcatcctg aacagcgagg cccagtttca gaccagccag ttctggatca   1500
tggaaaagac caaggccatc atgaagcacc tccacagcca gaacgtgaag ctgctgatct   1560
ccagcgtgaa gcagcccgac ctggtgtctt attatgccgg cgtgaacggc atcagcgtgg   1620
tggaatgtct gagcagcgaa gaggtgtccc tgatcagacg gatcatcgga ctgagcccct   1680
ttgtgcctcc tcaagccttt agccagtgcg agatccctaa cacagccctg gtcaagttct   1740
gcaagcccct gatcctgcgg agcaagagat atgtgcacct gggcctgatc agcacatgcg   1800
ccttcattcc tcactccatc gtgctgtgtg gacctgtgca cggactgatt gagcagcacg   1860
aagatgcact gcacggcgcc ctgaaaatgc tgagacagct gttcaaggac ctggacctga   1920
actacatgac ccagaccaac gaccagaacg gcaccagcag cctgttcatc tacaagaaca   1980
gcggcgagag ctatcaggcc ccagatccag gcaatggcag catccagagg ccttaccagg   2040
ataccgtggc cgagaacaag gacgccctgg aaaaaaccca gacctacctg aaggtgcaca   2100
gcaacctggt catccccgat gtggaactgg aaacctacat tccctacagc accccctacac  2160
tgacccctac cgataccttc cagaccgtgg aaaccctgac ctgtctgagc ctggaacgga   2220
acagactgac cgactactac gagcccctgc tgaaaaacaa cagcaccgcc tatagcaccc   2280
ggggcaacag aatcgagatc agctacgaga acctgcaagt gaccaacatc acccggaagg   2340
gctccatgct gccagtgtcc tgcaagctgc ctaatatggg caccagccag agctacctgt   2400
cctcttctat gcctgccgga tgtgtgctgc ctgtcggcgg caattttgag atcctgctgc   2460
actactacct gctgaactac gccaagaagt gccaccagag cgaagagaca atggtgtcca   2520
tgattatcgc caacgctctg ctgggcatcc ccaaggtgct gtacaagagc aagaccggca   2580
agtacagctt ccctcacacc tacattagag ccgtgcacgc cctgcagacc aatcagccac   2640
tggtttctag ccagacaggc ctggaaagcg tgatgggaaa gtaccagctg ctgaccagcg   2700
```

tgctgcagtg cctgaccaag atcctgacca tcgacatggt catcaccgtg aagcggcacc 2760
ctcagaaagt gcacaaccag gacagcgagg acgagctgta ggcgccgtcg ac 2812

<210> SEQ ID NO 38
<211> LENGTH: 2815
<212> TYPE: DNA
<213> ORGANISM: Artificial sequence
<220> FEATURE:
<223> OTHER INFORMATION: Construct comprising CMV promoter and COSEQ2-BBS10 nucleotide sequence (referred to as CMV-COSEQ2-BBS10)

<400> SEQUENCE: 38
actagttatt aatagtaatc aattacgggg tcattagttc atagcccata tatggagttc 60
cgcgttacat aacttacggt aaatggcccg cctggctgac cgcccaacga cccccgccca 120
ttgacgtcaa taatgacgta tgttcccata gtaacgccaa tagggacttt ccattgacgt 180
caatgggtgg agtatttacg gtaaactgcc cacttggcag tacatcaagt gtatcatatg 240
ccaagtacgc cccctattga cgtcaatgac ggtaaatggc ccgcctggca ttatgcccag 300
tacatgacct tatgggactt tcctacttgg cagtacatct acgtattagt catcgctatt 360
accatggtga tgcggttttg gcagtacatc aatgggcgtg gatagcggtt tgactcacgg 420
ggatttccaa gtctccaccc cattgacgtc aatgggagtt tgttttggca ccaaaatcaa 480
cgggactttc caaaatgtcg taacaactcc gccccattga cgcaaatggg cggtaggcgt 540
gtacggtggg aggtctatat aagcagagct ggtttagtga accgtcagat ccgctagcgc 600
taccggactc agatctcgaa ttcgccacca tgctgagctc catggctgcc gccggatctg 660
tgaaagccgc cctgcaggtg gcagaggtgc tggaggcaat cgtgagctgt tgcgtgggac 720
ctgagggccg gcaggtgctg tgcacaaagc caaccggcga ggtgctgctg tctagaaatg 780
gcggccggct gctggaggcc ctgcacctgg agcacccaat tgcaagaatg atcgtggact 840
gcgtgtctag ccacctgaag aagacaggcg atggcgccaa gaccttcatc atcttcctgt 900
gccacctgct gaggggcctg cacgccatca cagaccgcga gaaggatcct ctgatgtgcg 960
agaacatcca gacccacggc aggcactgga agaattgttc ccgctggaag ttcatctctc 1020
aggccctgct gacatttcag acccagatcc tggacggcat catggatcag tatctgagca 1080
ggcacttcct gtccatcttt tcctctgcca aggagcggac cctgtgcaga agctccctgg 1140
agctgctgct ggaggcctac ttctgtggcc gggtgggcag aaacaatcac aagtttatca 1200
gccagctgat gtgcgactat ttctttaagt gcatgacctg taagtccggc atcggcgtgt 1260
tcgagctggt ggacgatcac tttgtggagc tgaacgtggg agtgacaggc ctgcccgtgt 1320
ccgactctcg catcatcgcc ggcctggtgc tgcagaagga tttctccgtg taccggcctg 1380
ccgacggcga tatgagaatg gtcatcgtga ccgagacaat ccagccactg ttcagcacct 1440
ccggctctga gttcatcctg aacagcgagg cccagttcca gacatctcag ttttggatca 1500
tggagaagac caaggccatc atgaagcacc tgcacagcca gaacgtgaag ctgctgatct 1560
ctagcgtgaa gcagccagac ctggtgtctt actatgccgg cgtgaatggc atcagcgtgg 1620
tggagtgtct gtcctctgag gaggtgtccc tgatccggag aatcattggc ctgtctccct 1680
tcgtgccccc tcaggccttt agccagtgcg agatccccaa cacagccctg gtgaagttct 1740
gtaagcctct gatcctgagg tccaagcggt acgtgcacct gggcctgatc agcacctgcg 1800
cctttatccc acactctatc gtgctgtgcg gacctgtgca cggcctgatt gagcagcacg 1860
aggatgcact gcacggcgcc ctgaagatgc tgaggcagct gttcaaggac ctggatctga 1920
attacatgac ccagacaaac gaccagaatg gcacaagctc cctgtttatc tacaagaact 1980
ctggcgagag ctatcaggcc ccagatcccg gcaatggcag cattcagcgc ccctaccagg 2040
acacagtggc agagaacaag gatgccctgg agaagaccca gacatatctg aaggtgcact 2100
ccaacctggt catccctgac gtggagctgg agacatacat cccttattct accccaacac 2160
tgacccccac agataccttc cagacagtgg agacactgac ctgcctgtcc ctggagagga 2220
accgcctgac cgactactat gagcccctgc tgaagaacaa ttccacagcc tactctaccc 2280
ggggcaatag aatcgagatc agctatgaga acctgcaggt gacaaatatc accagaaagg 2340
gctctatgct gcctgtgagc tgcaagctgc caaacatggg caccagccag tcctacctgt 2400
ctagctccat gcctgcagga tgcgtgctgc ctgtgggcgg caacttcgag atcctgctgc 2460
actactatct gctgaattat gccaagaagt gccaccagag cgaggagaca atggtgtcca 2520
tgatcatcgc caacgccctg ctgggcatcc caaaggtgct gtacaagtct aagaccggca 2580
agtacagctt tccccacacc tatatccggg ccgtgcacgc cctgcagaca aatcagcctc 2640
tggtgtctag ccagaccggc ctggagtccg tgatgggcaa gtaccagctg ctgacatctg 2700
tgctgcagtg tctgacaaag atcctgacca tcgatatggt catcaccgtg aagagacacc 2760
cacagaaggt gcacaatcag gacagcgagg atgagctgta agcggccgcg tcgac 2815

<210> SEQ ID NO 39
<211> LENGTH: 2658
<212> TYPE: DNA
<213> ORGANISM: Artificial sequence
<220> FEATURE:
<223> OTHER INFORMATION: Construct comprising CBA promoter and wild type BBS10 nucleotide sequence (referred to as CBA-WTBBS10)

<400> SEQUENCE: 39
actagtgtac atctacgtat tagtcatcgc tattaccatg gtcgaggtga gccccacgtt 60
ctgcttcact ctccccatct ccccccccctc cccaccccca attttgtatt tatttatttt 120
ttaattattt tgtgcagcga tgggggcggg gggggggggg gggcgcgcgc caggcggggc 180
ggggcggggc gaggggcggg gcggggcgag gcggagaggt gcggcggcag ccaatcagag 240
cggcgcgctc cgaaagtttc cttttatggc gaggcggcgg cggcggcggc cctataaaaa 300
gcgaagcgcg cggcgggcgg gagtcgctgc gcgctgcctt cgccccgtgc cccgctccgc 360
cgccgcctcg cgccgcccgc cccggctctg actgaccgcg ttactcccac aggtgagcgg 420
gcgggacggc ccttctcctc cgggctgtaa ttagcgcttg gaattcgcca ccatgttaag 480
ttctatggcc gctgcagggt ctgtgaaggc ggcgttgcag gtggccgagg tgctggaagc 540
catcgtgagc tgctgcgtgg ggcccgaggg acggcaagtt ttgtgtacga agcccactgg 600
cgaggtgctt ctcagccgga atggaggccg cctcctggag gcgctacact tagagcatcc 660
catagccagg atgatagtgg actgtgtttc cagtcatctc aaaaaaacag gagatggtgc 720
aaaaacattt attatctttc tttgccattt gcttagagga cttcatgcaa tcacagacag 780
agaaaaggat cctttgatgt gtgaaaacat tcaaacccat ggaaggcatt ggaaaaattg 840
ttctcggtgg aaatttattt cccaggctct cctaacgttt cagacacaaa tattagacgg 900
tattatggac cagtacctaa gtagacactt tttgtctatc ttttcgtctg ctaaagagag 960
aacattgtgt aggagctctt tagagttgct cttagaagca tacttttgtg gaagagtggg 1020
aagaaataat cataaattta tttcacagtt gatgtgtgac tactttttca agtgtatgac 1080
ttgtaaaagt gggattggtg tatttgagtt agtggatgac cattttgtag agttgaatgt 1140

```
tggtgtcact ggccttcctg tttcagattc caggatcata gctggtcttg tgcttcagaa   1200

agatttttct gtgtaccgcc cagcagatgg tgacatgcga atggtgatag taacagaaac   1260

cattcagcct ctttttttcca cttctggatc agagtttatt ctaaattcag aagcacagtt   1320

tcagacatct caattttgga ttatggaaaa gacaaaagca ataatgaaac atctacatag   1380

tcagaatgta aaattgctca tatctagtgt gaaacaacca gatttagtta gttattatgc   1440

aggggtgaat ggcatatcag tggttgagtg tttatcatca gaagaagttt ctcttatccg   1500

gaggatcatt ggtctttctc catttgtacc accacaggcc ttttcgcagt gtgaaatacc   1560

taacactgct ttggtgaaat tttgtaaacc tcttatcctt agatccaaaa gatatgttca   1620

tctaggcttg ataagcacat gtgcatttat accacactct atagttcttt gtggaccagt   1680

gcatggtctc attgaacaac atgaggatgc tttacatgga gcacttaaaa tgcttcggca   1740

attatttaaa gaccttgatc taaattacat gacacaaacc aatgaccaaa atggcacttc   1800

aagtcttttt atttataaga acagtggaga aagttatcaa gcaccagatc ctggtaatgg   1860

ctcaatacaa aggccttatc aggacacagt tgcagagaac aaagatgcat tggaaaaaac   1920

tcaaacatat ttaaaagtac attctaattt ggtaattcca gatgtagaat tagaaacata   1980

tattccgtat tcaaccccca cactgacacc aacagataca ttccaaacag ttgaaacgct   2040

gacatgtttg tctttggaaa gaaacaggct aactgattat tatgaaccat tactcaagaa   2100

caattccact gcttattcaa caaggggaaa tagaatagaa atttcttacg aaaatttaca   2160

ggtcacaaat attactagaa agggaagcat gttaccagtg agctgtaagt taccgaatat   2220

gggtacttcc cagagttacc tttcctcatc tatgccagct ggttgtgttt tgccagtagg   2280

tggtaatttt gagatcttgt tacattacta tcttctcaat tatgccaaaa aatgccatca   2340

atcagaagaa accatggtta gtatgataat agctaatgca cttttaggca ttcccaaagt   2400

cctttataaa tctaaaacag gaaagtacag ctttccacat acatatataa gagctgtcca   2460

tgcactgcaa accaatcaac ccttggtaag cagtcagaca ggtttggaat cagtaatggg   2520

taaataccag ctactaactt cagttcttca gtgtttgaca aaaatattaa ccattgacat   2580

ggtaatcact gttaagagac accctcagaa agttcacaat caagattcag aagatgaact   2640

ataagcggcc gcgtcgac                                                 2658
```

<210> SEQ ID NO 40
<211> LENGTH: 2655
<212> TYPE: DNA
<213> ORGANISM: Artificial sequence
<220> FEATURE:
<223> OTHER INFORMATION: Construct comprising CBA promoter and COSEQ1-BBS10 nucleotide sequence (referred to as CBA-COSEQ1-BBS10)

<400> SEQUENCE: 40

```
actagtgtac atctacgtat tagtcatcgc tattaccatg gtcgaggtga gccccacgtt     60

ctgcttcact ctccccatct ccccccccctc cccaccccca attttgtatt tatttatttt    120

ttaattattt tgtgcagcga tgggggcggg gggggggggg gggcgcgcgc caggcggggc    180

ggggcggggc gaggggcggg gcggggcgag gcggagaggt gcggcggcag ccaatcagag    240

cggcgcgctc cgaaagtttc cttttatggc gaggcggcgg cggcggcggc cctataaaaa    300

gcgaagcgcg cggcgggcgg gagtcgctgc gcgctgcctt cgccccgtgc cccgctccgc    360

cgccgcctcg cgccgcccgc cccggctctg actgaccgcg ttactcccac aggtgagcgg    420

gcgggacggc ccttctcctc cgggctgtaa ttagcgcttg gaattcgcca ccatgctgtc    480
```

-continued

```
tagcatggct gccgctggat ctgtgaaagc tgctctgcag gttgccgagg tgctggaagc    540
catcgtgtct tgttgtgtgg gacctgaggg cagacaggtg ctgtgtacaa agcctacagg    600
cgaagtgctg ctgagcagaa atggcggcag actgctcgaa gccctgcacc tggaacaccc    660
tatcgccaga atgatcgtgg actgcgtgtc cagccacctg aagaaaacag gcgacggcgc    720
caagaccttc atcatctttc tgtgccatct gctgcggggc ctgcacgcca tcaccgatag    780
agaaaaggac cctctgatgt gcgagaacat ccagacacac ggccggcact ggaagaactg    840
ctcccggtgg aagtttatca gccaggctct gctgaccttt cagacccaga tcctggacgg    900
catcatggac cagtacctga gcagacactt cctgagcatc ttcagcagcg ccaaagaacg    960
gaccctgtgc agaagctctc tggaactgct gctcgaggcc tacttttgcg gcagagtggg   1020
cagaaacaac cacaagttca tctcccagct gatgtgtgac tacttcttca agtgcatgac   1080
ctgcaagagc ggcatcggcg tgttcgagct ggtggacgat cacttcgtgg aactgaatgt   1140
gggcgtgacc ggcctgcctg tgtccgatag cagaattatt gccggcctgg tgctgcagaa   1200
agacttcagc gtgtacagac ccgccgacgg cgacatgaga atggtcatcg tgaccgagac   1260
aatccagcct ctgttcagca caagcggcag cgagttcatc ctgaacagcg aggcccagtt   1320
tcagaccagc cagttctgga tcatggaaaa gaccaaggcc atcatgaagc acctccacag   1380
ccagaacgtg aagctgctga tctccagcgt gaagcagccc gacctggtgt cttattatgc   1440
cggcgtgaac ggcatcagcg tggtggaatg tctgagcagc gaagaggtgt ccctgatcag   1500
acggatcatc ggactgagcc cctttgtgcc tcctcaagcc tttagccagt gcgagatccc   1560
taacacagcc ctggtcaagt tctgcaagcc cctgatcctg cggagcaaga gatatgtgca   1620
cctgggcctg atcagcacat gcgccttcat tcctcactcc atcgtgctgt gtggacctgt   1680
gcacggactg attgagcagc acgaagatgc actgcacggc gccctgaaaa tgctgagaca   1740
gctgttcaag gacctggacc tgaactacat gacccagacc aacgaccaga acggcaccag   1800
cagcctgttc atctacaaga acagcggcga gagctatcag gccccagatc caggcaatgg   1860
cagcatccag aggccttacc aggataccgt ggccgagaac aaggacgccc tggaaaaaac   1920
ccagacctac ctgaaggtgc acagcaacct ggtcatcccc gatgtggaac tggaaaccta   1980
cattccctac agcaccccta cactgacccc taccgatacc ttccagaccg tggaaaccct   2040
gacctgtctg agcctggaac ggaacagact gaccgactac tacgagcccc tgctgaaaaa   2100
caacagcacc gcctatagca cccggggcaa cagaatcgag atcagctacg agaacctgca   2160
agtgaccaac atcacccgga agggctccat gctgccagtg tcctgcaagc tgcctaatat   2220
gggcaccagc cagagctacc tgtcctcttc tatgcctgcc ggatgtgtgc tgcctgtcgg   2280
cggcaatttt gagatcctgc tgcactacta cctgctgaac tacgccaaga agtgccacca   2340
gagcgaagag acaatggtgt ccatgattat cgccaacgct ctgctgggca tccccaaggt   2400
gctgtacaag agcaagaccg gcaagtacag cttccctcac acctacatta gagccgtgca   2460
cgccctgcag accaatcagc cactggtttc tagccagaca ggcctggaaa gcgtgatggg   2520
aaagtaccag ctgctgacca gcgtgctgca gtgcctgacc aagatcctga ccatcgacat   2580
ggtcatcacc gtgaagcggc accctcagaa agtgcacaac caggacagcg aggacgagct   2640
gtaggcgccg tcgac                                                    2655
```

<210> SEQ ID NO 41
<211> LENGTH: 2658
<212> TYPE: DNA

-continued

<213> ORGANISM: Artificial sequence
<220> FEATURE:
<223> OTHER INFORMATION: Construct comprising CBA promoter and COSEQ2-
BBS10 nucleotide sequence (referred to as CBA-COSEQ2-BBS10)

<400> SEQUENCE: 41
actagtgtac atctacgtat tagtcatcgc tattaccatg gtcgaggtga gccccacgtt 60
ctgcttcact ctccccatct cccccccctc cccaccccca attttgtatt tatttatttt 120
ttaattattt tgtgcagcga tgggggcggg gggggggggg gggcgcgcgc caggcggggc 180
ggggcggggc gaggggcggg gcggggcgag gcggagaggt gcggcggcag ccaatcagag 240
cggcgcgctc cgaaagtttc cttttatggc gaggcggcgg cggcggcggc cctataaaaa 300
gcgaagcgcg cggcgggcgg gagtcgctgc gcgctgcctt cgccccgtgc cccgctccgc 360
cgccgcctcg cgccgcccgc cccggctctg actgaccgcg ttactcccac aggtgagcgg 420
gcgggacggc ccttctcctc cgggctgtaa ttagcgcttg gaattcgcca ccatgctgag 480
ctccatggct gccgccggat ctgtgaaagc cgccctgcag gtggcagagg tgctggaggc 540
aatcgtgagc tgttgcgtgg gacctgaggg ccggcaggtg ctgtgcacaa agccaaccgg 600
cgaggtgctg ctgtctagaa atggcggccg gctgctggag gccctgcacc tggagcaccc 660
aattgcaaga atgatcgtgg actgcgtgtc tagccacctg aagaagacag gcgatggcgc 720
caagaccttc atcatcttcc tgtgccacct gctgaggggc ctgcacgcca tcacagaccg 780
cgagaaggat cctctgatgt gcgagaacat ccagacccac ggcaggcact ggaagaattg 840
ttcccgctgg aagttcatct ctcaggccct gctgacattt cagacccaga tcctggacgg 900
catcatggat cagtatctga gcaggcactt cctgtccatc ttttcctctg ccaaggagcg 960
gaccctgtgc agaagctccc tggagctgct gctggaggcc tacttctgtg gccgggtggg 1020
cagaaacaat cacaagttta tcagccagct gatgtgcgac tatttcttta agtgcatgac 1080
ctgtaagtcc ggcatcggcg tgttcgagct ggtggacgat cactttgtgg agctgaacgt 1140
gggagtgaca ggcctgcccg tgtccgactc tcgcatcatc gccggcctgg tgctgcagaa 1200
ggatttctcc gtgtaccggc ctgccgacgg cgatatgaga atggtcatcg tgaccgagac 1260
aatccagcca ctgttcagca cctccggctc tgagttcatc ctgaacagcg aggcccagtt 1320
ccagacatct cagttttgga tcatggagaa gaccaaggcc atcatgaagc acctgcacag 1380
ccagaacgtg aagctgctga tctctagcgt gaagcagcca gacctggtgt cttactatgc 1440
cggcgtgaat ggcatcagcg tggtggagtg tctgtcctct gaggaggtgt ccctgatccg 1500
gagaatcatt ggcctgtctc ccttcgtgcc ccctcaggcc tttagccagt gcgagatccc 1560
caacacagcc ctggtgaagt tctgtaagcc tctgatcctg aggtccaagc ggtacgtgca 1620
cctgggcctg atcagcacct gcgcctttat cccacactct atcgtgctgt gcggacctgt 1680
gcacggcctg attgagcagc acgaggatgc actgcacggc gccctgaaga tgctgaggca 1740
gctgttcaag gacctggatc tgaattacat gacccagaca aacgaccaga atggcacaag 1800
ctccctgttt atctacaaga actctggcga gagctatcag gccccagatc ccggcaatgg 1860
cagcattcag cgcccctacc aggacacagt ggcagagaac aaggatgccc tggagaagac 1920
ccagacatat ctgaaggtgc actccaacct ggtcatccct gacgtggagc tggagacata 1980
catcccttat tctaccccaa cactgacccc cacagatacc ttccagacag tggagacact 2040
gacctgcctg tccctggaga ggaaccgcct gaccgactac tatgagcccc tgctgaagaa 2100
caattccaca gcctactcta cccggggcaa tagaatcgag atcagctatg agaacctgca 2160

-continued ggtgacaaat atcaccagaa agggctctat gctgcctgtg agctgcaagc tgccaaacat 2220
gggcaccagc cagtcctacc tgtctagctc catgcctgca ggatgcgtgc tgcctgtggg 2280
cggcaacttc gagatcctgc tgcactacta tctgctgaat tatgccaaga agtgccacca 2340
gagcgaggag acaatggtgt ccatgatcat cgccaacgcc ctgctgggca tcccaaaggt 2400
gctgtacaag tctaagaccg gcaagtacag ctttccccac acctatatcc gggccgtgca 2460
cgccctgcag acaaatcagc ctctggtgtc tagccagacc ggcctggagt ccgtgatggg 2520
caagtaccag ctgctgacat ctgtgctgca gtgtctgaca aagatcctga ccatcgatat 2580
ggtcatcacc gtgaagagac acccacagaa ggtgcacaat caggacagcg aggatgagct 2640
gtaagcggcc gcgtcgac 2658

<210> SEQ ID NO 42
<211> LENGTH: 2901
<212> TYPE: DNA
<213> ORGANISM: Artificial sequence
<220> FEATURE:
<223> OTHER INFORMATION: Construct comprising CAG promoter and wild type BBS10 nucleotide sequence (referred to as CAG-WTBBS10)

<400> SEQUENCE: 42
actagttcct ggaggggtgg agtcgtgacc taggccattg acgtcaataa tgacgtatgt 60
tcccatagta acgccaatag ggactttcca ttgacgtcaa tgggtggagt atttacggta 120
aactgcccac ttggcagtac atcaagtgta tcatatgcca agtacgcccc ctattgacgt 180
caatgacggt aaatggcccg cctggcatta tgcccagtac atgaccttat gggactttcc 240
tacttggcag tacatctacg tattagtcat cgctattacc atggtcgagg tgagccccac 300
gttctgcttc actctcccca tctccccccc ctccccaccc ccaattttgt atttatttat 360
tttttaatta ttttgtgcag cgatgggggc gggggggggg ggggggcgcg cgccaggcgg 420
ggcggggcgg ggcgaggggc ggggcggggc gaggcggaga ggtgcggcgg cagccaatca 480
gagcggcgcg ctccgaaagt ttccttttat ggcgaggcgg cggcggcggc ggccctataa 540
aaagcgaagc gcgcggcggg cgggagtcgc tgcgcgctgc cttcgccccg tgccccgctc 600
cgccgccgcc tcgcgccgcc cgccccggct ctgactgacc gcgttactcc cacaggtgag 660
cgggcgggac ggcccttctc ctccgggctg taattagcgc ttggaattcg ccaccatgtt 720
aagttctatg gccgctgcag ggtctgtgaa ggcggcgttg caggtggccg aggtgctgga 780
agccatcgtg agctgctgcg tggggcccga gggacggcaa gttttgtgta cgaagcccac 840
tggcgaggtg cttctcagcc ggaatggagg ccgcctcctg gaggcgctac acttagagca 900
tcccatagcc aggatgatag tggactgtgt ttccagtcat ctcaaaaaaa caggagatgg 960
tgcaaaaaca tttattatct ttctttgcca tttgcttaga ggacttcatg caatcacaga 1020
cagagaaaag gatcctttga tgtgtgaaaa cattcaaacc catggaaggc attggaaaaa 1080
ttgttctcgg tggaaattta tttcccaggc tctcctaacg tttcagacac aaatattaga 1140
cggtattatg gaccagtacc taagtagaca ctttttgtct atcttttcgt ctgctaaaga 1200
gagaacattg tgtaggagct ctttagagtt gctcttagaa gcatactttt gtggaagagt 1260
gggaagaaat aatcataaat ttatttcaca gttgatgtgt gactactttt tcaagtgtat 1320
gacttgtaaa agtgggattg gtgtatttga gttagtggat gaccattttg tagagttgaa 1380
tgttggtgtc actggccttc ctgtttcaga ttccaggatc atagctggtc ttgtgcttca 1440
gaaagatttt tctgtgtacc gcccagcaga tggtgacatg cgaatggtga tagtaacaga 1500

-continued aaccattcag cctctttttt ccacttctgg atcagagttt attctaaatt cagaagcaca 1560
gtttcagaca tctcaatttt ggattatgga aaagacaaaa gcaataatga aacatctaca 1620
tagtcagaat gtaaaattgc tcatatctag tgtgaaacaa ccagatttag ttagttatta 1680
tgcaggggtg aatggcatat cagtggttga gtgtttatca tcagaagaag tttctcttat 1740
ccggaggatc attggtcttt ctccatttgt accaccacag gccttttcgc agtgtgaaat 1800
acctaacact gctttggtga aattttgtaa acctcttatc cttagatcca aaagatatgt 1860
tcatctaggc ttgataagca catgtgcatt tataccacac tctatagttc tttgtggacc 1920
agtgcatggt ctcattgaac aacatgagga tgctttacat ggagcactta aaatgcttcg 1980
gcaattattt aaagaccttg atctaaatta catgacacaa accaatgacc aaaatggcac 2040
ttcaagtctt tttatttata agaacagtgg agaaagttat caagcaccag atcctggtaa 2100
tggctcaata caaaggcctt atcaggacac agttgcagag aacaaagatg cattggaaaa 2160
aactcaaaca tatttaaaag tacattctaa tttggtaatt ccagatgtag aattagaaac 2220
atatattccg tattcaaccc ccacactgac accaacagat acattccaaa cagttgaaac 2280
gctgacatgt ttgtctttgg aaagaaacag gctaactgat tattatgaac cattactcaa 2340
gaacaattcc actgcttatt caacaagggg aaatagaata gaaatttctt acgaaaattt 2400
acaggtcaca aatattacta gaaagggaag catgttacca gtgagctgta agttaccgaa 2460
tatgggtact tcccagagtt acctttcctc atctatgcca gctggttgtg ttttgccagt 2520
aggtggtaat tttgagatct tgttacatta ctatcttctc aattatgcca aaaaatgcca 2580
tcaatcagaa gaaaccatgg ttagtatgat aatagctaat gcacttttag gcattcccaa 2640
agtcctttat aaatctaaaa caggaaagta cagctttcca catacatata taagagctgt 2700
ccatgcactg caaaccaatc aacccttggt aagcagtcag acaggtttgg aatcagtaat 2760
gggtaaatac cagctactaa cttcagttct tcagtgtttg acaaaaaatat taaccattga 2820 catggtaatc actgttaaga gacaccctca gaaagttcac aatcaagatt cagaagatga 2880
actataagcg gccgcgtcga c 2901

<210> SEQ ID NO 43
<211> LENGTH: 2898
<212> TYPE: DNA
<213> ORGANISM: Artificial sequence
<220> FEATURE:
<223> OTHER INFORMATION: Construct comprising CAG promoter and COSEQ1-
BBS10 nucleotide sequence (referred to as CAG-COSEQ1-BBS10)

<400> SEQUENCE: 43
actagttcct ggaggggtgg agtcgtgacc taggccattg acgtcaataa tgacgtatgt 60
tcccatagta acgccaatag ggactttcca ttgacgtcaa tgggtggagt atttacggta 120
aactgcccac ttggcagtac atcaagtgta tcatatgcca agtacgcccc ctattgacgt 180
caatgacggt aaatggcccg cctggcatta tgcccagtac atgaccttat gggactttcc 240
tacttggcag tacatctacg tattagtcat cgctattacc atggtcgagg tgagccccac 300
gttctgcttc actctcccca tctccccccc ctccccaccc ccaattttgt atttatttat 360
tttttaatta ttttgtgcag cgatgggggc gggggggggg ggggggcgcg cgccaggcgg 420
ggcggggcgg ggcgaggggc ggggcggggc gaggcggaga ggtgcggcgg cagccaatca 480
gagcggcgcg ctccgaaagt ttccttttat ggcgaggcgg cggcggcggc ggccctataa 540
aaagcgaagc gcgcggcggg cgggagtcgc tgcgcgctgc cttcgccccg tgccccgctc 600

-continued

```
cgccgccgcc tcgcgccgcc cgccccggct ctgactgacc gcgttactcc cacaggtgag    660
cgggcgggac ggcccttctc ctccgggctg taattagcgc ttggaattcg ccaccatgct    720
gtctagcatg gctgccgctg gatctgtgaa agctgctctg caggttgccg aggtgctgga    780
agccatcgtg tcttgttgtg tgggacctga gggcagacag gtgctgtgta caaagcctac    840
aggcgaagtg ctgctgagca gaaatggcgg cagactgctc gaagccctgc acctggaaca    900
ccctatcgcc agaatgatcg tggactgcgt gtccagccac ctgaagaaaa caggcgacgg    960
cgccaagacc ttcatcatct ttctgtgcca tctgctgcgg ggcctgcacg ccatcaccga   1020
tagagaaaag gaccctctga tgtgcgagaa catccagaca cacggccggc actggaagaa   1080
ctgctcccgg tggaagttta tcagccaggc tctgctgacc tttcagaccc agatcctgga   1140
cggcatcatg gaccagtacc tgagcagaca cttcctgagc atcttcagca gcgccaaaga   1200
acggaccctg tgcagaagct ctctggaact gctgctcgag gcctactttt gcggcagagt   1260
gggcagaaac aaccacaagt tcatctccca gctgatgtgt gactacttct tcaagtgcat   1320
gacctgcaag agcggcatcg gcgtgttcga gctggtggac gatcacttcg tggaactgaa   1380
tgtgggcgtg accggcctgc ctgtgtccga tagcagaatt attgccggcc tggtgctgca   1440
gaaagacttc agcgtgtaca gacccgccga cggcgacatg agaatggtca tcgtgaccga   1500
gacaatccag cctctgttca gcacaagcgg cagcgagttc atcctgaaca gcgaggccca   1560
gtttcagacc agccagttct ggatcatgga aaagaccaag gccatcatga agcacctcca   1620
cagccagaac gtgaagctgc tgatctccag cgtgaagcag cccgacctgg tgtcttatta   1680
tgccggcgtg aacggcatca gcgtggtgga atgtctgagc agcgaagagg tgtccctgat   1740
cagacggatc atcggactga gcccctttgt gcctcctcaa gcctttagcc agtgcgagat   1800
ccctaacaca gccctggtca agttctgcaa gcccctgatc ctgcggagca agagatatgt   1860
gcacctgggc ctgatcagca catgcgcctt cattcctcac tccatcgtgc tgtgtggacc   1920
tgtgcacgga ctgattgagc agcacgaaga tgcactgcac ggcgccctga aaatgctgag   1980
acagctgttc aaggacctgg acctgaacta catgacccag accaacgacc agaacggcac   2040
cagcagcctg ttcatctaca agaacagcgg cgagagctat caggccccag atccaggcaa   2100
tggcagcatc cagaggcctt accaggatac cgtggccgag aacaaggacg ccctggaaaa   2160
aacccagacc tacctgaagg tgcacagcaa cctggtcatc cccgatgtgg aactggaaac   2220
ctacattccc tacagcaccc ctacactgac ccctaccgat accttccaga ccgtggaaac   2280
cctgacctgt ctgagcctgg aacggaacag actgaccgac tactacgagc ccctgctgaa   2340
aaacaacagc accgcctata gcacccgggg caacagaatc gagatcagct acgagaacct   2400
gcaagtgacc aacatcaccc ggaagggctc catgctgcca gtgtcctgca agctgcctaa   2460
tatgggcacc agccagagct acctgtcctc ttctatgcct gccggatgtg tgctgcctgt   2520
cggcggcaat tttgagatcc tgctgcacta ctacctgctg aactacgcca agaagtgcca   2580
ccagagcgaa gagacaatgg tgtccatgat tatcgccaac gctctgctgg gcatccccaa   2640
ggtgctgtac aagagcaaga ccggcaagta cagcttccct cacacctaca ttagagccgt   2700
gcacgccctg cagaccaatc agccactggt ttctagccag acaggcctgg aaagcgtgat   2760
gggaaagtac cagctgctga ccagcgtgct gcagtgcctg accaagatcc tgaccatcga   2820
catggtcatc accgtgaagc ggcaccctca gaaagtgcac aaccaggaca gcgaggacga   2880
gctgtaggcg ccgtcgac                                                2898
```

-continued

<210> SEQ ID NO 44
<211> LENGTH: 2901
<212> TYPE: DNA
<213> ORGANISM: Artificial sequence
<220> FEATURE:
<223> OTHER INFORMATION: Construct comprising CAG promoter and COSEQ2-BBS10 nucleotide sequence (referred to as CAG-COSEQ2-BBS10)

<400> SEQUENCE: 44
actagttcct ggaggggtgg agtcgtgacc taggccattg acgtcaataa tgacgtatgt 60
tcccatagta acgccaatag ggactttcca ttgacgtcaa tgggtggagt atttacggta 120
aactgcccac ttggcagtac atcaagtgta tcatatgcca agtacgcccc ctattgacgt 180
caatgacggt aaatggcccg cctggcatta tgcccagtac atgaccttat gggactttcc 240
tacttggcag tacatctacg tattagtcat cgctattacc atggtcgagg tgagccccac 300
gttctgcttc actctcccca tctccccccc ctccccaccc ccaattttgt atttatttat 360
tttttaatta ttttgtgcag cgatgggggc gggggggggg ggggggcgcg cgccaggcgg 420
ggcggggcgg ggcgaggggc ggggcggggc gaggcggaga ggtgcggcgg cagccaatca 480
gagcggcgcg ctccgaaagt ttccttttat ggcgaggcgg cggcggcggc ggccctataa 540
aaagcgaagc gcgcggcggg cgggagtcgc tgcgcgctgc cttcgccccg tgccccgctc 600
cgccgccgcc tcgcgccgcc cgccccggct ctgactgacc gcgttactcc cacaggtgag 660
cgggcgggac ggcccttctc ctccgggctg taattagcgc ttggaattcg ccaccatgct 720
gagctccatg gctgccgccg gatctgtgaa agccgccctg caggtggcag aggtgctgga 780
ggcaatcgtg agctgttgcg tgggacctga gggccggcag gtgctgtgca caaagccaac 840
cggcgaggtg ctgctgtcta gaaatggcgg ccggctgctg gaggccctgc acctggagca 900
cccaattgca agaatgatcg tggactgcgt gtctagccac ctgaagaaga caggcgatgg 960
cgccaagacc ttcatcatct tcctgtgcca cctgctgagg ggcctgcacg ccatcacaga 1020
ccgcgagaag gatcctctga tgtgcgagaa catccagacc cacggcaggc actggaagaa 1080
ttgttcccgc tggaagttca tctctcaggc cctgctgaca tttcagaccc agatcctgga 1140
cggcatcatg gatcagtatc tgagcaggca cttcctgtcc atcttttcct ctgccaagga 1200
gcggaccctg tgcagaagct ccctggagct gctgctggag gcctacttct gtggccgggt 1260
gggcagaaac aatcacaagt ttatcagcca gctgatgtgc gactatttct ttaagtgcat 1320
gacctgtaag tccggcatcg gcgtgttcga gctggtggac gatcactttg tggagctgaa 1380
cgtgggagtg acaggcctgc ccgtgtccga ctctcgcatc atcgccggcc tggtgctgca 1440
gaaggatttc tccgtgtacc ggcctgccga cggcgatatg agaatggtca tcgtgaccga 1500
gacaatccag ccactgttca gcacctccgg ctctgagttc atcctgaaca gcgaggccca 1560
gttccagaca tctcagtttt ggatcatgga gaagaccaag gccatcatga agcacctgca 1620
cagccagaac gtgaagctgc tgatctctag cgtgaagcag ccagacctgg tgtcttacta 1680
tgccggcgtg aatggcatca gcgtggtgga gtgtctgtcc tctgaggagg tgtccctgat 1740
ccggagaatc attggcctgt ctcccttcgt gccccctcag gcctttagcc agtgcgagat 1800
ccccaacaca gccctggtga agttctgtaa gcctctgatc ctgaggtcca agcggtacgt 1860
gcacctgggc ctgatcagca cctgcgcctt tatcccacac tctatcgtgc tgtgcggacc 1920
tgtgcacggc ctgattgagc agcacgagga tgcactgcac ggcgccctga agatgctgag 1980
gcagctgttc aaggacctgg atctgaatta catgacccag acaaacgacc agaatggcac 2040
aagctccctg tttatctaca agaactctgg cgagagctat caggccccag atcccggcaa 2100

-continued

```
tggcagcatt cagcgcccct accaggacac agtggcagag aacaaggatg ccctggagaa   2160

gacccagaca tatctgaagg tgcactccaa cctggtcatc cctgacgtgg agctggagac   2220

atacatccct tattctaccc caacactgac ccccacagat accttccaga cagtggagac   2280

actgacctgc ctgtccctgg agaggaaccg cctgaccgac tactatgagc ccctgctgaa   2340

gaacaattcc acagcctact ctacccgggg caatagaatc gagatcagct atgagaacct   2400

gcaggtgaca aatatcacca gaaagggctc tatgctgcct gtgagctgca agctgccaaa   2460

catgggcacc agccagtcct acctgtctag ctccatgcct gcaggatgcg tgctgcctgt   2520

gggcggcaac ttcgagatcc tgctgcacta ctatctgctg aattatgcca agaagtgcca   2580

ccagagcgag gagacaatgg tgtccatgat catcgccaac gccctgctgg gcatcccaaa   2640

ggtgctgtac aagtctaaga ccggcaagta cagctttccc cacacctata tccgggccgt   2700

gcacgccctg cagacaaatc agcctctggt gtctagccag accggcctgg agtccgtgat   2760

gggcaagtac cagctgctga catctgtgct gcagtgtctg acaaagatcc tgaccatcga   2820

tatggtcatc accgtgaaga gacacccaca gaaggtgcac aatcaggaca gcgaggatga   2880

gctgtaagcg gccgcgtcga c                                              2901
```

<210> SEQ ID NO 45
<211> LENGTH: 204
<212> TYPE: DNA
<213> ORGANISM: Human cytomegalovirus

<400> SEQUENCE: 45

```
gtgatgcggt tttggcagta catcaatggg cgtggatagc ggtttgactc acggggattt     60

ccaagtctcc accccattga cgtcaatggg agtttgtttt ggcaccaaaa tcaacgggac    120

tttccaaaat gtcgtaacaa ctccgcccca ttgacgcaaa tgggcggtag gcgtgtacgg    180

tgggaggtct atataagcag agct                                           204
```

<210> SEQ ID NO 46
<211> LENGTH: 232
<212> TYPE: DNA
<213> ORGANISM: Homo sapiens

<400> SEQUENCE: 46

```
ggctccggtg cccgtcagtg ggcagagcgc acatcgccca cagtccccga gaagttgtgg     60

ggaggggtcg gcaattgaac cggtgcctag agaaggtggc gcggggtaaa ctgggaaagt    120

gatgtcgtgt actggctccg cctttttccc gagggtgggg gagaaccgta tataagtgca    180

gtagtcgccg tgaacgttct ttttcgcaac gggtttgccg ccagaacaca gg            232
```

<210> SEQ ID NO 47
<211> LENGTH: 528
<212> TYPE: DNA
<213> ORGANISM: Artificial sequence
<220> FEATURE:
<223> OTHER INFORMATION: CAG promoter sequence

<400> SEQUENCE: 47

```
ccattgacgt caataatgac gtatgttccc atagtaacgc caatagggac tttccattga     60

cgtcaatggg tggagtattt acggtaaact gcccacttgg cagtacatca agtgtatcat    120

atgccaagta cgccccctat tgacgtcaat gacggtaaat ggcccgcctg gcattatgcc    180

cagtacatga ccttatggga ctttcctact tggcagtaca tctacgtatt agtcatcgct    240
```

-continued

```
attaccatgg tcgaggtgag ccccacgttc tgcttcactc tccccatctc cccccccctcc    300

ccaccccaa ttttgtattt atttattttt taattatttt gtgcagcgat gggggcgggg    360

gggggggggg ggcgcgcgcc aggcggggcg gggcggggcg aggggcgggg cggggcgagg    420

cggagaggtg cggcggcagc caatcagagc ggcgcgctcc gaaagtttcc ttttatggcg    480

aggcggcggc ggcggcggcc ctataaaaag cgaagcgcgc ggcgggcg                  528
```

<210> SEQ ID NO 48
<211> LENGTH: 1170
<212> TYPE: DNA
<213> ORGANISM: Homo sapiens

<400> SEQUENCE: 48

```
ggcctccgcg ccgggttttg gcgcctcccg cgggcgcccc cctcctcacg gcgagcgctg     60

ccacgtcaga cgaagggcgc agcgagcgtc ctgatccttc cgcccggacg ctcaggacag    120

cggcccgctg ctcataagac tcggccttag aaccccagta tcagcagaag gacattttag    180

gacgggactt gggtgactct agggcactgg ttttctttcc agagagcgga acaggcgagg    240

aaaagtagtc ccttctcggc gattctgcgg agggatctcc gtggggcggt gaacgccgat    300

gattatataa ggacgcgccg ggtgtggcac agctagttcc gtcgcagccg ggatttgggt    360

cgcggttctt gtttgtggat cgctgtgatc gtcacttggt gagtagcggg ctgctgggct    420

ggccggggct ttcgtggccg ccgggccgct cggtgggacg gaagcgtgtg gagagaccgc    480

caagggctgt agtctgggtc cgcgagcaag gttgccctga actgggggtt ggggggagcg    540

cagcaaaatg gcggctgttc ccgagtcttg aatggaagac gcttgtgagg cgggctgtga    600

ggtcgttgaa acaaggtggg gggcatggtg ggcggcaaga acccaaggtc ttgaggcctt    660

cgctaatgcg ggaaagctct tattcgggtg agatgggctg ggcaccatc tggggaccct    720

gacgtgaagt ttgtcactga ctggagaact cggtttgtcg tctgttgcgg gggcggcagt    780

tatggcggtg ccgttgggca gtgcacccgt acctttggga gcgcgcgccc tcgtcgtgtc    840

gtgacgtcac ccgttctgtt ggcttataat gcagggtggg gccacctgcc ggtaggtgtg    900

cggtaggctt ttctccgtcg caggacgcag ggttcgggcc tagggtaggc tctcctgaat    960

cgacaggcgc cggacctctg gtgaggggag ggataagtga ggcgtcagtt tctttggtcg   1020

gttttatgta cctatcttct taagtagctg aagctccggt tttgaactat gcgctcgggg   1080

ttggcgagtg tgttttgtga agttttttag gcaccttttg aaatgtaatc atttgggtca   1140

atatgtaatt ttcagtgtta gactagtaaa                                     1170
```

<210> SEQ ID NO 49
<211> LENGTH: 278
<212> TYPE: DNA
<213> ORGANISM: Gallus gallus

<400> SEQUENCE: 49

```
tcgaggtgag ccccacgttc tgcttcactc tccccatctc cccccccctcc ccaccccaa     60

ttttgtattt atttattttt taattatttt gtgcagcgat gggggcgggg gggggggggg    120

ggcgcgcgcc aggcggggcg gggcggggcg aggggcgggg cggggcgagg cggagaggtg    180

cggcggcagc caatcagagc ggcgcgctcc gaaagtttcc ttttatggcg aggcggcggc    240

ggcggcggcc ctataaaaag cgaagcgcgc ggcgggcg                            278
```